(12) United States Patent
Merriman et al.

(10) Patent No.: US 11,371,955 B2
(45) Date of Patent: *Jun. 28, 2022

(54) PROCESSIVE ENZYME MOLECULAR ELECTRONIC SENSORS FOR DNA DATA STORAGE

(71) Applicant: Roswell Biotechnologies, Inc., San Diego, CA (US)

(72) Inventors: Barry Merriman, San Diego, CA (US); Tim Geiser, San Diego, CA (US); Paul Mola, San Diego, CA (US); Gina Costa, San Diego, CA (US)

(73) Assignee: ROSWELL BIOTECHNOLOGIES, INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/639,716

(22) PCT Filed: Aug. 30, 2018

(86) PCT No.: PCT/US2018/048873
§ 371 (c)(1),
(2) Date: Feb. 17, 2020

(87) PCT Pub. No.: WO2019/046589
PCT Pub. Date: Mar. 7, 2019

(65) Prior Publication Data
US 2020/0217813 A1 Jul. 9, 2020

Related U.S. Application Data

(60) Provisional application No. 62/551,977, filed on Aug. 30, 2017.

(51) Int. Cl.
*C12M 1/34* (2006.01)
*G01N 27/30* (2006.01)
(Continued)

(52) U.S. Cl.
CPC ......... *G01N 27/30* (2013.01); *G01N 27/4145* (2013.01); *G01N 33/48721* (2013.01)

(58) Field of Classification Search
CPC ......... H01L 27/14609; H01L 27/14634; H01L 27/14636; H01L 27/14643;
(Continued)

(56) References Cited

U.S. PATENT DOCUMENTS 4,923,586 A * 5/1990 Katayama ............... C12Q 1/001
204/403.05
5,082,627 A  1/1992 Stanbro
(Continued)

FOREIGN PATENT DOCUMENTS

CN  1795376  6/2006
CN  102706940  10/2012
(Continued)

OTHER PUBLICATIONS

Argarana et al "molecular cloning and nucleotide sequence of the streptavidin gene" Nucleic Acids Research, 1986, 14 (4): 1871-1882. (Year: 1986).*
(Continued)

*Primary Examiner* — Frank W Lu
(74) *Attorney, Agent, or Firm* — Spectrum IP Law Group LLC

(57) ABSTRACT

A processive enzyme molecular sensor for use in a DNA data storage system is disclosed that can extract digital information suitably encoded into a synthetic DNA molecule. In various aspects, such sensors are provided in a high-density chip-based format that can provide the high throughput, low-cost and fast data extraction capability required for large scale DNA data storage systems. The sensor for reading the digital data stored in DNA molecules processes individual encoded DNA molecules directly,
(Continued)

eliminating the need for complicated sample preparation such as making copies of DNA or clonal populations of such molecules.

10 Claims, 38 Drawing Sheets

(51) Int. Cl.
    *G01N 27/414*     (2006.01)
    *G01N 33/487*     (2006.01)

(58) Field of Classification Search
    CPC ........ H01L 27/14881; H01L 29/76808; C12Q 1/001; C12Q 2565/607; C12Q 1/6825; C12Q 2563/116; C12Q 2521/101; G01N 27/4145; G01N 27/30; G01N 33/48721; G01N 27/3275; G01N 27/3278; H03F 3/345; H03G 1/0029; C12N 15/11
    See application file for complete search history.

(56) References Cited

U.S. PATENT DOCUMENTS

| | | |
|---|---|---|
| 5,194,133 A | 3/1993 | Clark et al. |
| 5,366,140 A | 11/1994 | Koskenmaki et al. |
| 5,414,588 A | 5/1995 | Barbee, Jr. |
| 5,486,449 A | 1/1996 | Honso et al. |
| 5,532,128 A | 7/1996 | Eggers et al. |
| 5,583,359 A | 12/1996 | Ng et al. |
| 5,639,507 A | 6/1997 | Galvagni et al. |
| 5,646,420 A | 7/1997 | Yamashita |
| 5,767,687 A | 6/1998 | Geist |
| 5,871,918 A | 2/1999 | Thorp et al. |
| 5,881,184 A | 3/1999 | Guidash |
| 5,965,452 A | 10/1999 | Kovacs |
| 5,982,018 A | 11/1999 | Wark |
| 6,051,380 A | 4/2000 | Sosnowski et al. |
| 6,060,023 A | 5/2000 | Maracas |
| 6,094,335 A | 7/2000 | Early |
| 6,110,354 A | 8/2000 | Saban |
| 6,123,819 A | 9/2000 | Peeters |
| 6,144,023 A | 11/2000 | Clerc |
| 6,238,927 B1 | 5/2001 | Abrams et al. |
| 6,440,662 B1 | 8/2002 | Gerwen et al. |
| 6,464,889 B1 | 10/2002 | Lee et al. |
| 6,506,564 B1 | 1/2003 | Mirkin et al. |
| 6,537,747 B1 | 3/2003 | Mills, Jr. et al. |
| 6,670,131 B2 | 12/2003 | Hashimoto |
| 6,673,533 B1 | 1/2004 | Wohlstadter et al. |
| 6,716,620 B2 | 4/2004 | Bashir et al. |
| 6,749,731 B2 | 6/2004 | Kobori |
| 6,762,050 B2 | 7/2004 | Fukushima et al. |
| 6,764,745 B1 | 7/2004 | Karasawa et al. |
| 6,790,341 B1 | 9/2004 | Saban |
| 6,824,974 B2 | 11/2004 | Pisharody et al. |
| 6,861,224 B2 | 3/2005 | Fujita et al. |
| 6,916,614 B1 | 7/2005 | Takenaka et al. |
| 6,958,216 B2 | 10/2005 | Kelley |
| 7,015,046 B2 | 3/2006 | Wohlstadter et al. |
| 7,075,428 B1 | 7/2006 | Oleynik |
| 7,169,272 B2 | 1/2007 | Fritsch et al. |
| 7,183,055 B2 | 2/2007 | Van Der Weide |
| 7,189,435 B2 | 3/2007 | Tuominen et al. |
| 7,202,480 B2 | 4/2007 | Yokoi et al. |
| 7,208,077 B1 | 4/2007 | Albers et al. |
| 7,276,206 B2 | 10/2007 | Augustine et al. |
| 7,399,585 B2 | 7/2008 | Gau |
| 7,432,120 B2 | 10/2008 | Mascolo et al. |
| 7,470,533 B2 | 12/2008 | Xu et al. |
| 7,507,320 B2 | 3/2009 | Hwang et al. |
| 7,531,120 B2 | 5/2009 | Van Rijn et al. |
| 7,579,823 B1 | 8/2009 | Ayliffe |
| 7,691,433 B2 | 4/2010 | Kronholz et al. |
| 7,785,785 B2 | 8/2010 | Pourmand et al. |
| 7,834,344 B2 | 11/2010 | Mascolo et al. |
| 7,851,045 B2 | 12/2010 | Gandon et al. |
| 7,886,601 B2 | 2/2011 | Merassi et al. |
| 7,901,629 B2 | 3/2011 | Calatzis et al. |
| 7,943,394 B2 | 5/2011 | Flandre et al. |
| 8,241,508 B2 | 8/2012 | D'Urso |
| 8,313,633 B2 | 11/2012 | Li et al. |
| 8,351,181 B1 | 1/2013 | Ahn |
| 8,591,816 B2 | 11/2013 | Calatzis et al. |
| 8,652,768 B1 | 2/2014 | Huber et al. |
| 8,753,893 B2 | 6/2014 | Liu et al. |
| 8,927,464 B2 | 1/2015 | Aizenberg et al. |
| 8,940,663 B2 | 1/2015 | Iqbal et al. |
| 9,070,733 B2 | 6/2015 | Rajagopal et al. |
| 9,108,880 B2 | 8/2015 | Jin et al. |
| 9,139,614 B2 | 9/2015 | Medintz |
| 9,306,164 B1 | 4/2016 | Chang et al. |
| 9,829,456 B1 | 11/2017 | Merriman et al. |
| 9,956,743 B2 | 5/2018 | Jin et al. |
| 10,036,064 B2 | 7/2018 | Merriman et al. |
| 10,125,420 B2 | 11/2018 | Jin et al. |
| 10,151,722 B2 | 12/2018 | Jin et al. |
| 10,508,296 B2 | 12/2019 | Merriman et al. |
| 10,526,696 B2 | 1/2020 | Jin et al. |
| 10,584,410 B2 | 3/2020 | Jin et al. |
| 10,597,767 B2 | 3/2020 | Merriman et al. |
| 10,712,334 B2 | 7/2020 | Choi et al. |
| 2002/0022223 A1 | 2/2002 | Connolly |
| 2002/0090649 A1 | 7/2002 | Chan et al. |
| 2002/0137083 A1 | 9/2002 | Kobori et al. |
| 2002/0138049 A1 | 9/2002 | Allen et al. |
| 2002/0142150 A1 | 10/2002 | Baumann et al. |
| 2002/0142477 A1 | 10/2002 | Lewis et al. |
| 2002/0172963 A1 | 11/2002 | Kelley et al. |
| 2002/0184939 A1 | 12/2002 | Yadav |
| 2003/0025133 A1 | 2/2003 | Brousseau |
| 2003/0040000 A1 | 2/2003 | Connolly et al. |
| 2003/0040173 A1 | 2/2003 | Fonash |
| 2003/0064390 A1 | 4/2003 | Schülein et al. |
| 2003/0087296 A1 | 5/2003 | Fujita et al. |
| 2003/0109031 A1 | 6/2003 | Chafin et al. |
| 2003/0141189 A1 | 7/2003 | Lee et al. |
| 2003/0141276 A1 | 7/2003 | Lee et al. |
| 2003/0186263 A1 | 10/2003 | Frey et al. |
| 2003/0224387 A1 | 12/2003 | Kunwar et al. |
| 2004/0014106 A1 | 1/2004 | Patno et al. |
| 2004/0023253 A1 | 2/2004 | Kunwar et al. |
| 2004/0038090 A1 | 2/2004 | Faris |
| 2004/0048241 A1 | 3/2004 | Freeman et al. |
| 2004/0063100 A1 | 4/2004 | Wang |
| 2004/0086929 A1 | 5/2004 | Weide et al. |
| 2004/0096866 A1 | 5/2004 | Hoffman et al. |
| 2004/0012161 A1 | 6/2004 | Chiu |
| 2004/0146863 A1 | 7/2004 | Pisharody et al. |
| 2004/0209355 A1 | 10/2004 | Edman et al. |
| 2004/0209435 A1 | 10/2004 | Patridge et al. |
| 2004/0229247 A1 | 11/2004 | DeBoer et al. |
| 2004/0235016 A1 | 11/2004 | Hamers |
| 2004/0248282 A1 | 12/2004 | Sobha |
| 2005/0029227 A1 | 2/2005 | Chapman |
| 2005/0067086 A1 | 3/2005 | Ito et al. |
| 2005/0074911 A1 | 4/2005 | Kornilovich et al. |
| 2005/0151541 A1 | 7/2005 | Brinz et al. |
| 2005/0156157 A1 | 7/2005 | Parsons et al. |
| 2005/0164371 A1 | 7/2005 | Arinaga |
| 2005/0172199 A1 | 8/2005 | Miller et al. |
| 2005/0181195 A1 | 8/2005 | Dubrow |
| 2005/0221473 A1 | 10/2005 | Dubin et al. |
| 2005/0227373 A1 | 10/2005 | Flandre et al. |
| 2005/0247573 A1 | 11/2005 | Nakamura et al. |
| 2005/0285275 A1 | 12/2005 | Son |
| 2005/0287548 A1 | 12/2005 | Bao et al. |
| 2005/0287589 A1 | 12/2005 | Connolly |
| 2006/0003482 A1 | 1/2006 | Chinthakindi et al. |
| 2006/0019273 A1 | 1/2006 | Connolly et al. |
| 2006/0024504 A1 | 2/2006 | Nelson et al. |
| 2006/0024508 A1 | 2/2006 | D'Urso et al. |
| 2006/0029808 A1 | 2/2006 | Zhai et al. |
| 2006/0051919 A1 | 3/2006 | Mascolo et al. |

(56) References Cited

U.S. PATENT DOCUMENTS

| | | |
|---|---|---|
| 2006/0051946 A1 | 3/2006 | Mascolo et al. |
| 2006/0105449 A1 | 5/2006 | Larmer et al. |
| 2006/0105467 A1 | 5/2006 | Niksa et al. |
| 2006/0128239 A1 | 5/2006 | Nun et al. |
| 2006/0147983 A1 | 7/2006 | O'uchi |
| 2006/0154489 A1 | 7/2006 | Tornow |
| 2006/0275853 A1 | 12/2006 | Matthew et al. |
| 2007/0026193 A1 | 2/2007 | Luzinov et al. |
| 2007/0048748 A1 | 3/2007 | Williams et al. |
| 2007/0140902 A1 | 6/2007 | Calatzis et al. |
| 2007/0148815 A1 | 6/2007 | Chao et al. |
| 2007/0186628 A1 | 8/2007 | Curry et al. |
| 2007/0184247 A1 | 9/2007 | Simpson et al. |
| 2007/0207487 A1 | 9/2007 | Emig et al. |
| 2007/0231542 A1 | 10/2007 | Deng |
| 2008/0012007 A1 | 1/2008 | Li et al. |
| 2008/0098815 A1 | 5/2008 | Merassi et al. |
| 2008/0149479 A1 | 6/2008 | Olofsson et al. |
| 2008/0199657 A1 | 8/2008 | Capron et al. |
| 2008/0199659 A1 | 8/2008 | Zhao |
| 2009/0011222 A1 | 1/2009 | Xin et al. |
| 2009/0017571 A1 | 1/2009 | Nuckolls |
| 2009/0020428 A1 | 1/2009 | Levitan |
| 2009/0027036 A1 | 1/2009 | Nuckolls et al. |
| 2009/0062684 A1 | 3/2009 | Gregersen et al. |
| 2009/0152109 A1 | 6/2009 | Whitehead et al. |
| 2009/0162927 A1 | 6/2009 | Naaman et al. |
| 2009/0170716 A1 | 7/2009 | Su et al. |
| 2009/0178935 A1 | 7/2009 | Reymond et al. |
| 2009/0295372 A1 | 12/2009 | Krstic et al. |
| 2009/0297913 A1 | 12/2009 | Zhang et al. |
| 2009/0306578 A1 | 12/2009 | Sivan et al. |
| 2009/0324308 A1 | 12/2009 | Law et al. |
| 2010/0035254 A1* | 2/2010 | Williams ............. C12Q 1/6869 435/6.11 |
| 2010/0038342 A1 | 2/2010 | Lim et al. |
| 2010/0044212 A1 | 2/2010 | Kim et al. |
| 2010/0055397 A1 | 3/2010 | Kurihara et al. |
| 2010/0132771 A1 | 6/2010 | Lu |
| 2010/0142259 A1 | 6/2010 | Drndic et al. |
| 2010/0149530 A1 | 6/2010 | Tomaru |
| 2010/0167938 A1 | 7/2010 | Su et al. |
| 2010/0184062 A1 | 7/2010 | Steinmueller-Nethl et al. |
| 2010/0188109 A1 | 7/2010 | Edel et al. |
| 2010/0194409 A1 | 8/2010 | Gao et al. |
| 2010/0201381 A1 | 8/2010 | Iqbal et al. |
| 2010/0206367 A1 | 8/2010 | Jeong et al. |
| 2010/0227416 A1 | 9/2010 | Koh et al. |
| 2010/0280397 A1 | 11/2010 | Feldman et al. |
| 2010/0285275 A1 | 11/2010 | Baca et al. |
| 2010/0285601 A1 | 11/2010 | Kong et al. |
| 2010/0288543 A1 | 11/2010 | Hung et al. |
| 2010/0300899 A1 | 12/2010 | Levine et al. |
| 2011/0056845 A1 | 3/2011 | Stellacci |
| 2011/0065588 A1 | 3/2011 | Su et al. |
| 2011/0076783 A1 | 3/2011 | Liu et al. |
| 2011/0091787 A1 | 4/2011 | McGrath et al. |
| 2011/0160077 A1 | 6/2011 | Chaisson et al. |
| 2011/0166034 A1 | 7/2011 | Kwong et al. |
| 2011/0217763 A1 | 9/2011 | Rasooly et al. |
| 2011/0227558 A1 | 9/2011 | Mannion et al. |
| 2011/0229667 A1 | 9/2011 | Jin et al. |
| 2011/0233075 A1 | 9/2011 | Soleymani et al. |
| 2011/0248315 A1 | 10/2011 | Nam et al. |
| 2011/0287956 A1 | 11/2011 | Iqbal et al. |
| 2011/0291673 A1 | 12/2011 | Shibata et al. |
| 2011/0311853 A1 | 12/2011 | Fratti |
| 2011/0312529 A1 | 12/2011 | He et al. |
| 2012/0060905 A1 | 3/2012 | Fogel et al. |
| 2012/0122715 A1 | 5/2012 | Gao et al. |
| 2012/0220046 A1 | 8/2012 | Chao |
| 2012/0258870 A1 | 10/2012 | Schwartz et al. |
| 2012/0286332 A1 | 11/2012 | Rothberg et al. |
| 2012/0309106 A1 | 12/2012 | Eichen et al. |
| 2013/0049158 A1 | 2/2013 | Hong et al. |
| 2013/0071289 A1 | 3/2013 | Knoll |
| 2013/0108956 A1 | 5/2013 | Lu et al. |
| 2013/0109577 A1 | 5/2013 | Korlach et al. |
| 2013/0162276 A1 | 6/2013 | Lee et al. |
| 2013/0183492 A1 | 7/2013 | Lee et al. |
| 2013/0214875 A1 | 8/2013 | Duncan et al. |
| 2013/0239349 A1 | 9/2013 | Knights et al. |
| 2013/0245416 A1 | 9/2013 | Yarmush et al. |
| 2013/0273340 A1 | 10/2013 | Neretina et al. |
| 2013/0281325 A1 | 10/2013 | Elibol et al. |
| 2013/0331299 A1 | 12/2013 | Reda et al. |
| 2014/0001055 A1 | 1/2014 | Elibol et al. |
| 2014/0011013 A1 | 1/2014 | Jin |
| 2014/0018262 A1 | 1/2014 | Reda et al. |
| 2014/0048776 A1 | 2/2014 | Huang et al. |
| 2014/0054788 A1 | 2/2014 | Majima et al. |
| 2014/0057283 A1 | 2/2014 | Wang et al. |
| 2014/0061049 A1 | 3/2014 | Lo et al. |
| 2014/0079592 A1 | 3/2014 | Chang et al. |
| 2014/0027775 A1 | 6/2014 | Quick et al. |
| 2014/0170567 A1 | 6/2014 | Sakamoto et al. |
| 2014/0174927 A1 | 6/2014 | Bashir et al. |
| 2014/0197459 A1 | 7/2014 | Kis et al. |
| 2014/0218637 A1 | 8/2014 | Gao et al. |
| 2014/0235493 A1 | 8/2014 | Zang et al. |
| 2014/0253827 A1 | 9/2014 | Gao et al. |
| 2014/0284667 A1 | 9/2014 | Basker et al. |
| 2014/0320849 A1 | 10/2014 | Chou et al. |
| 2014/0367749 A1 | 12/2014 | Bai et al. |
| 2014/0377900 A1 | 12/2014 | Yann et al. |
| 2015/0005188 A1 | 1/2015 | Levner et al. |
| 2015/0017655 A1 | 1/2015 | Huang et al. |
| 2015/0049332 A1 | 2/2015 | Sun et al. |
| 2015/0057182 A1 | 2/2015 | Merriman et al. |
| 2015/0065353 A1 | 3/2015 | Turner et al. |
| 2015/0068892 A1 | 3/2015 | Ueno et al. |
| 2015/0077183 A1* | 3/2015 | Ciubotaru ........... H03F 3/45179 330/254 |
| 2015/0148264 A1 | 5/2015 | Esfandyarpour et al. |
| 2015/0177150 A1 | 6/2015 | Rothberg et al. |
| 2015/0191709 A1 | 7/2015 | Heron et al. |
| 2015/0263203 A1 | 9/2015 | Lewis et al. |
| 2015/0293025 A1 | 10/2015 | Ninomiya et al. |
| 2015/0294875 A1 | 10/2015 | Khondaker et al. |
| 2015/0344945 A1 | 12/2015 | Mandell et al. |
| 2016/0017416 A1 | 1/2016 | Boyanov et al. |
| 2016/0045378 A1 | 2/2016 | Geloen |
| 2016/0155971 A1 | 6/2016 | Strachan et al. |
| 2016/0187282 A1 | 6/2016 | Gardner et al. |
| 2016/0265047 A1 | 9/2016 | van Rooyen et al. |
| 2016/0284811 A1 | 9/2016 | Yu et al. |
| 2016/0290957 A1 | 10/2016 | Ram |
| 2016/0319342 A1 | 11/2016 | Kawai et al. |
| 2016/0377564 A1 | 12/2016 | Carmignani et al. |
| 2017/0023512 A1 | 1/2017 | Cummins et al. |
| 2017/0037462 A1 | 2/2017 | Turner et al. |
| 2017/0038333 A1* | 2/2017 | Turner .................. G11C 19/28 |
| 2017/0043355 A1 | 2/2017 | Fischer |
| 2017/0044605 A1 | 2/2017 | Merriman |
| 2017/0131237 A1 | 5/2017 | Ikeda |
| 2017/0184542 A1 | 6/2017 | Chatelier et al. |
| 2017/0234825 A1 | 8/2017 | Elibol et al. |
| 2017/0240962 A1 | 8/2017 | Merriman |
| 2017/0288017 A1 | 10/2017 | Majima et al. |
| 2017/0332918 A1 | 11/2017 | Keane |
| 2018/0014786 A1 | 1/2018 | Keane |
| 2018/0031508 A1 | 2/2018 | Jin |
| 2018/0031509 A1 | 2/2018 | Jin |
| 2018/0045665 A1 | 2/2018 | Jin |
| 2018/0259474 A1 | 9/2018 | Jin |
| 2018/0297321 A1 | 10/2018 | Jin et al. |
| 2018/0305727 A1 | 10/2018 | Merriman |
| 2018/0340220 A1 | 11/2018 | Merriman |
| 2019/0004003 A1 | 1/2019 | Merriman |
| 2019/0033244 A1 | 1/2019 | Jin |
| 2019/0039065 A1 | 2/2019 | Choi |
| 2019/0041355 A1 | 2/2019 | Merriman |
| 2019/0041378 A1 | 2/2019 | Choi |
| 2019/0094175 A1 | 3/2019 | Merriman |

(56) References Cited

U.S. PATENT DOCUMENTS

| | | |
|---|---|---|
| 2019/0194801 A1 | 6/2019 | Jin et al. |
| 2019/0355442 A1 | 11/2019 | Merriman et al. |
| 2019/0376925 A1 | 12/2019 | Choi et al. |
| 2019/0383770 A1 | 12/2019 | Choi et al. |
| 2020/0157595 A1 | 5/2020 | Merriman et al. |
| 2020/0217813 A1 | 7/2020 | Merriman et al. |
| 2020/0242482 A1 | 7/2020 | Merriman et al. |
| 2020/0277645 A1 | 9/2020 | Merriman et al. |
| 2020/0385850 A1 | 12/2020 | Merriman et al. |
| 2020/0385855 A1 | 12/2020 | Jin et al. |
| 2020/0393440 A1 | 12/2020 | Jin et al. |

FOREIGN PATENT DOCUMENTS

| | | |
|---|---|---|
| CN | 104685066 | 6/2015 |
| CN | 104703700 | 6/2015 |
| CN | 108027335 | 5/2018 |
| DE | 102012008375 | 10/2012 |
| EP | 2053383 | 4/2009 |
| EP | 3403079 | 11/2018 |
| EP | 3408219 | 12/2018 |
| EP | 3408220 | 12/2018 |
| EP | 3414784 | 12/2018 |
| EP | 3420580 | 1/2019 |
| GB | 2485559 | 5/2012 |
| JP | 0233981 | 7/1990 |
| JP | 2008-258594 | 10/2008 |
| JP | 2018-522236 | 8/2018 |
| KR | 20070059880 | 6/2007 |
| KR | 20110104245 | 9/2011 |
| WO | 2001044501 | 6/2001 |
| WO | 2002049980 | 6/2002 |
| WO | 2002074985 | 9/2002 |
| WO | 2003042396 | 5/2003 |
| WO | 2004096986 | 11/2004 |
| WO | 2004099307 | 11/2004 |
| WO | 2005108612 | 11/2005 |
| WO | 2007054649 | 5/2007 |
| WO | 2007102960 | 9/2007 |
| WO | 2007126432 | 11/2007 |
| WO | 2007128965 | 11/2007 |
| WO | 2009003208 | 1/2009 |
| WO | 2009035647 | 3/2009 |
| WO | 2010022107 | 2/2010 |
| WO | 2012083249 | 6/2012 |
| WO | 2012087352 | 6/2012 |
| WO | 2012152056 | 11/2012 |
| WO | 2013096851 | 6/2013 |
| WO | 2014182630 | 7/2014 |
| WO | 2015167019 | 11/2015 |
| WO | 2015176990 | 11/2015 |
| WO | 2015188197 | 12/2015 |
| WO | 2016016635 | 2/2016 |
| WO | 2016100635 | 6/2016 |
| WO | 2016100637 | 6/2016 |
| WO | 2016196755 | 12/2016 |
| WO | 2016210386 | 12/2016 |
| WO | 2017027518 | 2/2017 |
| WO | 2017041056 | 3/2017 |
| WO | 2017042038 | 3/2017 |
| WO | 2017061129 | 4/2017 |
| WO | 2017123416 | 7/2017 |
| WO | 2017132567 | 8/2017 |
| WO | 2017132586 | 8/2017 |
| WO | 2017139493 | 8/2017 |
| WO | 2017147187 | 8/2017 |
| WO | 2017151680 | 9/2017 |
| WO | 2017184677 | 10/2017 |
| WO | 2018022799 | 2/2018 |
| WO | 2018026855 | 2/2018 |
| WO | 2018098286 | 5/2018 |
| WO | 2018132457 | 7/2018 |
| WO | 2018136148 | 7/2018 |
| WO | 2018200687 | 11/2018 |
| WO | 2018208505 | 11/2018 |
| WO | 2003091458 | 1/2019 |

OTHER PUBLICATIONS

USPTO; Requirement for Restriction dated Nov. 2, 2011 in U.S. Appl. No. 12/667,583.
USPTO; Non-Final Office Action dated Sep. 28, 2018 in U.S. Appl. No. 12/667,583.
USPTO; Final Office Action dated Feb. 19, 2019 in U.S. Appl. No. 12/667,583.
USPTO; Non-Final Office Action dated Aug. 19, 2019 in U.S. Appl. No. 12/667,583.
USPTO; Requirement for Restriction dated Dec. 1, 2016 in U.S. Appl. No. 13/996,477.
USPTO; Non-Final Office Action dated May 5, 2017 in U.S. Appl. No. 13/996,477.
USPTO; Final Office Action dated Oct. 4, 2017 in U.S. Appl. No. 13/996,477.
USPTO; Notice of Allowance dated Jan. 3, 2018 in U.S. Appl. No. 13/996,477.
USPTO; Final Office Action dated Dec. 30, 2016 in U.S. Appl. No. 15/050,270.
USPTO; Advisory Action dated Mar. 14, 2017 in U.S. Appl. No. 15/050,270.
USPTO; Non-Final Office Action dated Sep. 29, 2017 in U.S. Appl. No. 15/050,270.
USPTO; Final Office Action dated Jul. 10, 2018 in U.S. Appl. No. 15/050,270.
USPTO; Advisory Action dated Sep. 26, 2018 in U.S. Appl. No. 15/050,270.
USPTO; Non-Final Office Action dated Feb. 26, 2019 in U.S. Appl. No. 15/050,270.
USPTO; Final Office Action dated Jul. 10, 2019 in U.S. Appl. No. 15/050,270.
USPTO; Notice of Allowance dated Jan. 6, 2020 in U.S. Appl. No. 15/050,270.
USPTO; Non-Final Office Action dated Oct. 19, 2016 in U.S. Appl. No. 15/220,307.
USPTO; Notice of Allowance dated Jul. 28, 2017 in U.S. Appl. No. 15/220,307.
USPTO; Requirement for Restriction dated Jan. 17, 2017 in U.S. Appl. No. 15/336,557.
USPTO; Non-Final Office Action dated May 16, 2017 in U.S. Appl. No. 15/336,557.
USPTO; Final Office Action dated Mar. 8, 2018 in U.S. Appl. No. 15/336,557.
USPTO; Notice of Allowance dated May 25, 2018 in U.S. Appl. No. 15/336,557.
USPTO; Non-Final Office Action dated Feb. 9, 2018 in U.S. Appl. No. 15/728,400.
USPTO; Final Office Action dated Jul. 10, 2018 in U.S. Appl. No. 15/728,400.
USPTO; Advisory Action dated Oct. 12, 2018 in U.S. Appl. No. 15/728,400.
USPTO; Advisory Action dated Nov. 14, 2018 in U.S. Appl. No. 15/728,400.
USPTO; Notice of Allowance dated Dec. 6, 2018 in U.S. Appl. No. 15/728,400.
USPTO; Non-Final Office Action dated Feb. 23, 2018 in U.S. Appl. No. 15/728,412.
USPTO; Notice of Allowance dated Sep. 12, 2018 in U.S. Appl. No. 15/728,412.
USPTO; Final Office Action dated Jun. 13, 2018 in U.S. Appl. No. 15/728,412.
USPTO; Non-Final Office Action dated Feb. 23, 2018 in U.S. Appl. No. 15/796,080.
USPTO; Final Office Action dated Jun. 14, 2018 in U.S. Appl. No. 15/796,080.
USPTO; Advisory Action dated Sep. 4, 2018 in U.S. Appl. No. 15/796,080.

(56) References Cited

OTHER PUBLICATIONS

USPTO; Notice of Allowance dated Oct. 11, 2018 in U.S. Appl. No. 15/796,080.
USPTO; Non-Final Office Action dated March 7, 2019 in U.S. Appl. No. 15/944,356.
USPTO; Non-Final Office Action dated Sep. 4, 2018 in U.S. Appl. No. 15/979,135.
USPTO; Non-Final Office Action dated Nov. 30, 2018 in U.S. Appl. No. 15/979,135.
USPTO; Final Office Action dated Mar. 1, 2019 in U.S. Appl. No. 15/979,135.
USPTO; Advisory Action dated May 22, 2019 in U.S. Appl. No. 15/979,135.
USPTO; Non-Final Office Action dated Jun. 25, 2019 in U.S. Appl. No. 15/979,135.
USPTO; Notice of Allowance dated Dec. 11, 2019 in U.S. Appl. No. 15/979,135.
USPTO; Non-Final Office Action dated Aug. 22, 2019 in the U.S. Appl. No. 16/011,065.
USPTO; Final Office Action dated Mar. 6, 2020 in U.S. Appl. No. 16/011,065.
USPTO; Requirement for Restriction dated Oct. 15, 2018 in U.S. Appl. No. 16/015,028.
USPTO; Non-Final Office Action dated Dec. 26, 2018 in U.S. Appl. No. 16/015,028.
USPTO; Final Office Action dated Apr. 15, 2019 in U.S. Appl. No. 16/015,028.
USPTO; Non-Final Office Action dated Jul. 30, 2019 in the U.S. Appl. No. 16/015,028.
USPTO; Notice of Allowance dated Nov. 8, 2019 in U.S. Appl. No. 16/015,028.
USPTO; Requirement for Restriction dated Dec. 17, 2018 in U.S. Appl. No. 16/015,049.
USPTO; Non-Final Office Action dated Mar. 6, 2019 in U.S. Appl. No. 16/015,049.
USPTO; Final Office Action dated Jun. 19, 2019 in U.S. Appl. No. 16/015,049.
USPTO; Non-Final Office Action dated Nov. 5, 2019 in U.S. Appl. No. 16/015,049.
USPTO; Notice of Allowance dated Feb. 20, 2020 in U.S. Appl. No. 16/015,049.
USPTO; Non-Final Office Action dated Apr. 13, 2020 in U.S. Appl. No. 16/070,133.
USPTO; Restriction Requirement dated Sep. 19, 2019 in U.S. Appl. No. 16/073,706.
USPTO; Non-Final Office Action dated Oct. 24, 2019 in U.S. Appl. No. 16/073,706.
USPTO; Non-Final Office Action dated Jan. 10, 2020 in U.S. Appl. No. 16/076,673.
USPTO; Non-Final Office Action dated Feb. 1, 2019 in U.S. Appl. No. 16/152,190.
USPTO; Notice of Allowance dated May 30, 2019, in U.S. Appl. No. 16/152,190.
USPTO; Restriction Requirement dated May 29, 2019 in U.S. Appl. No. 16/250,929.
USPTO; Notice of Allowance dated Oct. 23, 2019 in U.S. Appl. No. 16/250,929.
USPTO; Restriction Requirement dated Apr. 8, 2020 in U.S. Appl. No. 16/479,257.
PCT; International Search Report and Written Opinion dated Nov. 29, 2012 in Application No. PCT/US2011/001995.
PCT; International Search Report and Written Opinion dated Apr. 13, 2018 in Application No. PCT/US2018/013140.
PCT; International Search Report and Written Opinion dated Jan. 27, 2017 in Application No. PCT/US2017/015437.
PCT; International Search Report and Written Opinion dated Jan. 27, 2017 in Application No. PCT/US2017/015465.
PCT; International Search Report and Written Opinion dated Jul. 26, 2017 in Application No. PCT/US2017/017231.
PCT; International Search Report and Written Opinion dated May 25, 2017 in Application No. PCT/US2017/018950.
PCT; International Search Report and Written Opinion dated Jul. 20, 2018 in Application No. PCT/US2018/029382.
PCT; International Search Report and Written Opinion dated Jul. 20, 2018 in Application No. PCT/US2018/029393.
PCT; International Search Report and Written Opinion dated Sep. 27, 2016 in Application No. PCT/US2016/039446.
PCT; International Search Report and Written Opinion dated Nov. 22, 2017 in Application No. PCT/US2017/044023.
PCT; International Search Report and Written Opinion dated Dec. 26, 2017 in Application No. PCT/US2017/044965.
PCT; International Search Report and Written Opinion received Nov. 9, 2018 in Application No. PCT/US2018/048873.
PCT; International Search Report and Written Opinion dated Apr. 8, 2010 in Application No. PCT/US2009/054235.
PCT; International Search Report and Written Opinion dated Jan. 18, 2019 in Application No. PCT/US2018/055264.
PCT; International Search Report and Written Opinion dated Mar. 12, 2018 in Application No. PCT/US2017/063025.
PCT; International Search Report and Written Opinion dated Mar. 7, 2018 in Application No. PCT/US2017/063105.
PCT; International Search Report and Written Opinion dated Apr. 18, 2017 in Application No. PCT/US2016/068922.
CN; Notice of the First Office Action dated Sep. 2, 2019 in Chinese Application No. 201680049272.8.
CN; Notice of the First Office Action dated Sep. 30, 2019 in Chinese Application No. 201780020478.2.
EP; European Search Report dated Jan. 30, 2019 in Application No. 16815467.2.
EP; European Search Report dated Aug. 2, 2019 in Application No. 16885434.7.
EP; European Search Report dated Jan. 29, 2020 in Application No. 17745013.7.
EP; European Search Report dated Aug. 2, 2019 in Application No. 17745026.9.
EP; European Search Report dated Jan. 29, 2020 in Application No. 17750776.1.
EP; European Search Report dated Oct. 24, 2019 in Application No. 17757146.0.
EP; European Search Report dated Mar. 6, 2020 in Application No. 17835231.6.
EP; European Search Report dated Feb. 7, 2020 in Application No. 17837566.3.
Ahn et al., "Electrical Immunosensor Based on a Submicron-Gap Interdigitated Electrode and Gold Enhancement," Biosensors and Bioelectronics, vol. 26, pp. 4690-4696, (2011).
Alayo et al., "Gold Interdigitated Nanoelectrodes as a Sensitive Analytical Tool for Selective Detection of Electroactive Species via Redox Cycling," Microchim Acta, vol. 183, pp. 1633-1639, (2016).
Antibody Structure Downloaded from https://absoluteantibody.com/antibody-resources/antibody-overview/antibody-structure/ (Mar. 1, 2019).
Bai et al., "Review: Gas Sensors Based on Conducting Polymers," Sensors, vol. 7, pp. 267-307, (2007).
Bailey et al., "DNA-Encoded Antibody Libraries: A Unified Platform for Multiplexed Cell Sorting and Detection of Genes and Proteins," Journal of American Chemical Society, vol. 129, pp. 1959-1967, (2007).
Bechelany et al. "Synthesis Mechanisms of Organized Nanoparticles: Influence of Annealing Temperature and Atmosphere," Crystal Growth and Design, vol. 10, pp. 587-596 (Oct. 21, 2010).
Berdat et al., "Label-Free Detection of DNA with Interdigitated Micro-Electrodes in a Fluidic Cell," Lab on a Chip, vol. 8, pp. 302-308, (2008).
Bhura, "3D Interdigitated Electrode Array (IDEA) Biosensor for Detection of Serum Biomarker," Master Thesis, Portland State University, 68 Pages, (2011).
Blossey, R., "Self-Cleaning Surfaces—Virtual Realities," Nature Materials, vol. 2(5), pp. 301-306, (May 2006).
Bonilla et al., "Electrical Readout of Protein Microarrays on Regular Glass Slides," Analytical Chemistry, vol. 83, pp. 1726-1731, (2011).

(56) References Cited

OTHER PUBLICATIONS

Botsialas et al., "A Miniaturized Chemocapacitor System for the Detection of Volatile Organic Compounds," Sensors and Actuators B, Chemical, vol. 177, pp. 776-784, (2013).
Branagan et al., "Enhanced Mass Transport of Electroactive Species to Annular Nanoband Electrodes Embedded in Nanocapillary Array Membranes," Journal of the American Chemical Society, vol. 134, pp. 8617-8624, (2012).
Braun et al., "DNA-Templated Assembly and Electrode Attachment of a Conducting Silver Wire," Letters to Nature, vol. 391(6669), pp. 775-778, (Feb. 1998).
Briglin et al., "Exploitation of Spatiotemporal Information and Geometric Optimization of Signal/Noise Performance Using Arrays of Carbon Black-Polymer Composite Vapor Detectors," Sensors and Actuators B, vol. 82, pp. 54-74, (2002).
Cassie, A.B.D. et al., "Wettability of Porous Surfaces," Transitions of the Faraday Society, vol. 40, pp. 546-551, (Jan. 1944) (Abstract Only).
Cerofolini et al., "A Hybrid Approach to Nanoelectronics: A Hybrid Approach to Nanoelectrics," Nanotechnology, Institute of Physics Publishing, GB, vol. 16, No. 8, pp. 1040-1047 (2005).
Chen, X. et al., "Electrical Nanogap Devices for Biosensing," Materials Today, vol. 13, pp. 28-41, (Nov. 2010).
Chen et al., "Electrochemical Approach for Fabricating Nanogap Electrodes with Well Controllable Separation," Applied Physics Letters, vol. 86, pp. 123105.1-123105.3, (2005).
Chen et al., "Fabrication of Submicron-Gap Electrodes by Silicon Volume Expansion for DNA-Detection," Sensors and Actuators A, vol. 175, pp. 73-77, (2012).
Choi, J. E. et al., "Fabrication of Microchannel with 60 Electrodes and Resistance Measurement," Flow Measurement and Instrumentation, vol. 21, pp. 178-183, (Sep. 2010) (Abstract Only).
Choi Y.S. et al., "Hybridization by an Electroatomical Genome on Detection on Using an Indicator-Free DNA on a Microelectrode-Array DNA Chip," Bulletin of the Korean Chemistry Society, vol. 26, pp. 379-383, (2005).
Choi, C. et al., "Strongly Superhydrophobic Silicon Nanowires by Supercritical CO2 Drying," Electronic Materials Letters, vol. 6 (2), pp. 59-64, (Jun. 2010).
Church et al., "Next-Generation Digital Information Storage in DNA," Science, vol. 337(6102), p. 6102, (Sep. 28, 2012).
Cosofret et al., "Microfabricated Sensor Arrays Sensitive to pH and K+ for Ionic Distribution Measurements in the Beating Heart," Analytical Chemistry, vol. 67, pp. 1647-1653, (1995).
Coulson S.R. et al., "Super-Repellent Composite Fluoropolymer Surfaces," The Journal of Physical Chemistry B., vol. 104(37), pp. 8836-8840, (Aug. 2000).
Dickey et al., "Electrically Addressable Parallel Nanowires with 30 NM Spacing from Micromolding and Nanoskiving," Nano Letters, vol. 8(12), pp. 4568-4573, (2008).
Fan et al., "Detection of MicroRNAs Using Target-Guided Formation of Conducting Polymer Nanowires in Nanogaps," Journal of the American Chemical Society, vol. 129, pp. 5437-5443, (2007).
Fink et al. "Electrical Conduction Through DNA Molecules," Nature, vol. 398, pp. 407-410 (Jan. 20, 1999).
Fuller et al., "Real-Time Single-Molecule Electronic DNA Sequencing by Synthesis Using Polymer-Tagged Nucleotides on a Nanopore Array," Proceedings of the National Academy of Sciences, vol. 113(19), pp. 5233-5523, (May 10, 2016).
Gapin, A.I. et al., "CoPt Patterned Media in Anodized Aluminum Oxide Templates," Journal of Applied Physics, vol. 99(8), pp. 08G902 (1-3), (Apr. 2006).
Ghindilis, A. et al., "Real Time Biosensor Platforms Fully Integrated Device for Impedimetric Assays," ECS Transactions, vol. 33, pp. 59-68, (2010).
Guo et al., "Conductivity of a single DNA duplex bridging a carbon nanotube gap," Nat. Nanotechnol., vol. 3, No. 3, pp. 1-12 (2008).
Han, "Energy Band Gap Engineering of Graphene Nanoribbons," Physical Review Letters, vol. 98, pp. 1-7, (May 16, 2007).
Han et al., "Redox Cycling in Nanopore-Confined Recessed Dual-Ring Electrode Arrays," Journal of Physical Chemistry C, vol. 120, pp. 20634-20641, (2016).
Hanief, Topic, Pineda-Vargas, "Solid State Dewetting of Continuous Thin Platinum Coatings," Nuclear Instruments and Methods in Physics Research, vol. 363, pp. 173-176, (2015).
Hashioka et al., "Deoxyribonucleic Acid Sensing Device with 40-NM-Gap-Electrodes Fabricated by Low-Cost Conventional Techniques," Applied Physics Letters, vol. 85(4), p. 687-688, (Jul. 2004).
He et al., "Electromechanical Fabrication of Atomically Thin Metallic Wires and Electrodes Separated with Molecular-Scale Gaps," Journal of Electroanalytical Chemistry, vol. 522, pp. 167-172, (Jan. 2002).
Heerema et al., "Graphene Nanodevices for DNA Sequencing," Nature Nanotechnology, vol. 11, pp. 127-136, (Feb. 3, 2016).
Henry et al., "Microcavities Containing Individually Addressable Recessed Microdisk and Tubular Nanoband Electrodes," Journal of the Electrochemical Society, vol. 146(9), pp. 3367-3373, (1999).
Hwang et al., "Electrical Transport Through 60 Base Pairs of Poly (dG)-Poly (dC) DNA Molecules," Applied Physics Letters, vol. 81(6), p. 1134-1136, (Aug. 2002).
Ino et al., "Addressable Electrode Array Device with IDA Electrodes for High-Throughput Detection," Lab on a Chip, vol. 11, p. 385-388, (2011).
Ino et al., "Local Redox-Cycling-Based Electrochemical Chip Device with Seep Microwells for Evaluation of Embryoid Bodies," Angewandte Chemie International Edition, vol. 51, pp. 6648-6652, (2012).
Iqbal et al., "Direct Current Electrical Characterization of ds-DNA in Nanogap Junctions," Applied Physics Letter, vol. 86, p. 153901-1-153901-3, (Apr. 2005).
Javey et al., "Layer-By-Layer Assembly of Nanowires for Three-Dimensional, Multifunctional Electronics," Nano Letters, vol. 7, pp. 773-777, (2007).
Khawli et al., "Charge Variants in IgG1-Isolation, Characterization, In Vitro Binding Properties and Pharmacokinetics in Rats," Landes Bioscience, vol. 2(6), pp. 613-623, (2010).
Kim, J. Y. et al., "Optically Transparent Glass with Vertically Aligned Surface Al2O3 Nanowires Having Superhydrophobic Characteristics," Nano: Brief Reports and Reviews, vol. 5(2), pp. 89-95, (Apr. 2010) (Abstract Only).
Kim et al., "Rapid Fabrication of Uniformly Sized Nanopores and Nanopore Arrays for Parallel DNA Analysis," Advances Materials, vol. 18, pp. 3149-3153, (Dec. 4, 2006).
Kitsara et al., "Single Chip Interdigitated Electrode Capacitive Chemical Sensor Arrays," Sensors and Actuators B, vol. 127, pp. 186-192, (2007).
Kitsara et al., "Small-Volume Multiparametric Electrochemical Detection at Low Cost Polymeric Devices Featuring Nanoelectrodes," SPIE, vol. 9518, 9 Pages, (2015).
Kraft, "Doped Diamond: A Compact Review on a New, Versatile Electrode Material," International Journal of Electrochemistry, vol. 2, pp. 355-385, (May 2007).
Kumar et al., "Terminal Phosphate Labeled Nucleotides: Synthesis, Applications and Linker Effect on Incorporation by DNA Polymerases," Nucleosides, Nucleotides and Nucleic Acids, Taylor and Francis, vol. 24, No. 5-7, pp. 401-408 (2005).
Lee, K. H. et al., "One-Chip Electronic Detection of DNA Hybridization using Precision Impedance-Based CMOS Array Sensor," Biosensors and Bioelectronics, vol. 26, pp. 1373-1379, (Dec. 15, 2010).
Lin et al., "An Addressable Microelectrode Array for Electrichemical Detection," Analytical Chemistry, vol. 80, pp. 6830-6833, (2008).
Liu et al., "Atomically Thin Molybdenum Disulfide Nanopores with High Sensitivity for DNA Translocation," ACS Nano, vol. 8, pp. 2504-2511, (Feb. 18, 2014).
Liu et al., "An Enzyme-Based E-DNA Sensor for Sequence-Specific Detection of Femtomolar DNA Targets," J. Am. Chem. Soc., vol. 130(21), pp. 6820-6825, (2008).
Liu et al., "Controllable Nanogap Fabrication on Microchip by Chronopotentiometry," Electrochimica Acta, vol. 50, pp. 3041-3047, (2005).

(56) References Cited

OTHER PUBLICATIONS

MacNaughton et al., "High-Throughput Heterogeneous Integration of Diverse Nanomaterials on a Single Chip for Sensing Applications," PLOS One, vol. 9(10), e111377, 7 Pages, (2014).

Mastrototaro et al., "Thin-Film Flexible Multielectrode Arrays for Voltage Measurements in the Heart," IEEE Engineering in Medicine & Biology Society 11th Annual International Conference, 1 Page, (1989).

Mastrototaro et al., "Rigid and Flexible Thin-Film Multielectrode Arrays for Transmural Cardiac Recording," IEEE Transactions on Biomedical Engineering, vol. 39, pp. 217-279, (1992).

Mirando-Castro et al., "Hairpin-DNA Probe for Enzyme-Amplified Electrochemical Detection of Legionella pnuemophila," Anal. Chem., vol. 79, pp. 4050-4055, (Jun. 1, 2007).

Nishida, et al. "Self-Oriented Immobilization of DNA Polymerase Tagged by Titanium-Binding Peptide Motif," Langmuir, vol. 31, pp. 732-740 (Dec. 17, 2014).

Niwa, O. et al., "Fabrication and Characteristics of Vertically Separated Interdigitated Array Electrodes," Journal of Electroanalytical Chemistry and Interfacial Electrochemistry, vol. 267 pp. 291-297, (Aug. 10, 1989) (Abstract Only).

Okinaka et al., ""Polymer" Inclusions in Cobalt-Hardened Electroplated Gold," Journal the of Electrochemical Society, vol. 125, p. 1745, (1978). (Abstract Only).

Park, S.J. et al., "Array-Based Electrical Detection of DNA with Nanoparticle Probes," Science, vol. 295, pp. 1503-1506, (Feb. 22, 2002).

Park, C.W. et al., "Fabrication of Poly-Si/ AU Nano-Gaps Using Atomic-Layer-Deposited $Al_2O_3$ as a Sacrificial Layer," Nanotechnology, vol. 16, pp. 361-364, (Feb. 1, 2005) (Abstract Only).

Parkin, I. P. et al., "Self-Cleaning Coatings," Journal of Materials Chemistry, vol. 15(17), pp. 1689-1695, (Dec. 2004).

Prins et al., "Room-Temperature Gating of Molecular Junctions Using Few-Layer Graphene Nanogap Electrodes," Nano Letters, vol. 11, pp. 4607-4611, (Oct. 21, 2011).

Pugliese et al., "Processive Inforporation of Deoxynucleoside Triphosphate Analogs by Single-Molecule DNA Polymerase I (Klenow Fragment) Nanocircuits," Journal of the American Chemical Society, vol. 137, No. 30, pp. 9587-9594 (2015).

Qing et al., "Finely Tuning Metallic Nanogap Size with Electrodeposition by Utilizing High-Frequency Impedance in Feedback," Angewandte Chemie Int ed, vol. 44, pp. 7771-7775, (2005).

Reed et al., "Conductance of a Molecular Junction Reports," Science, vol. 278, pp. 252-254, (Oct. 1997).

Reichert et al., "Driving Current Through Single Organic Molecules," Physical Review Letters, vol. 88(17), pp. 176804-1-176804-4, (Apr. 2002).

Roppert et al., "A New Approach for an Interdigitated Electrodes DNA-Sensor," XVIIIth International Symposium on Bioelectrochemistry and Bioenergetics, Bioelectrochemistry, p. 143, (2005).

Roy, S. et al., "Mass-Produced Nanogap Sensor Arrays for Ultra-Sensitive Detection of DNA," Journal of the American Chemical Society, vol. 131, pp. 12211-12217, (Aug. 5, 2009) (Abstract Only).

Ruttkowski, E. et al., "CMOS based Arrays of Nanogaps Devices for Molecular Devices," Proceedings of 2005 5th IEEE Conference on Nanotechnology, vol. 1, pp. 438-441, (Jul. 2005) (Abstract Only).

Sanguino et al., "Interdigitated Capacitive Immunosensors with PVDF Immobilization Layers," IEEE Sensors Journal, vol. 14(4), pp. 1260-1265, (Apr. 2014).

Santschi et al., "Interdigitated 50nm Ti Electrode Arrays Fabricated using $XeF_2$ Enhanced Focused Ion Beam Etching," Nanotechnology, vol. 17, pp. 2722-2729, (2006).

Schaefer et al., "Stability and Dewetting Kinetics of Thin Gold Films on Ti, TiOx, and ZnO Adhesion Layers," Acta Materialia, vol. 61, pp. 7841-7848, (2013).

Schrott, W. et al., "Metal Electrodes in Plastic Microfluidic Systems," Microelectronic Engineering, vol. 86, pp. 1340-1342, (Jun. 2009).

Shimanovsky et al., "Hiding Data in DNA," International Workshop on Information Hiding, Lecture Notes in Computer Science, pp. 373-386, (Dec. 18, 2012).

Shimoda, T. et al., "Solution-Processed Silicon Films and Transistors," Nature, vol. 440(7085), pp. 783-786, (Apr. 2006).

Sholders et al., "Distinct Conformations of a Putative Translocation Element in Poliovirus Polymerase," Journal of Molecular Biology, vol. 426(7), pp. 1407-1419, (Apr. 3, 2014).

Singh et al., "3D Nanogap Interdigitated Electrode Array Biosensors," Analytical and Bioanalytical Chemistry, vol. 397, pp. 1493-1502, (2010).

Singh et al., "Evaluation of Nanomaterials-Biomolecule Hybrids for Signals Enhancement of Impedimetric Biosensors," 11th IEEE International Conference on Nanotechnology, pp. 707-710, (2011).

Singh et al., "Nanoparticle-Enhanced Sensitivity of a Nanogap-Interdigitated Electrode Array Impedimetric Biosensor," Langmuir, vol. 27, pp. 13931-13939, (2011).

Stagni, C. et al., "CMOS DNA Sensor Array with Integrated A/D Conversation Based on Label-Free Capacitance Measurement," IEEE Journal of Solid-State Circuits, vol. 41, pp. 2956-2964, (Nov. 20, 2006).

Stenning, "The Investigation of Grain Boundary Development and Crystal Synthesis of Thin Gold Films on Silicon Wafers," http://www.ucl.ac.uk/~ucapikr/projects, (Mar. 31, 2009).

Su, Y., "Modeling and Characteristic Study of Thin Film Based Biosensor Based on COMSOL," Mathematical Problems in Engineering, Article 581063 (6 Pages), (Apr. 7, 2014).

Thompson, "Solid-State Dewetting of Thin Films," Department of Materials Science and Engineering, vol. 42, pp. 399-434, (2012).

Urban, M. et al., "A Paralleled Readout System for an Electrical DNA-Hybridization Assay Based on a Microstructured Electrode Array," Review of Scientific Instruments, vol. 74, pp. 1077-1081, (Jan. 2003) (Abstract Only).

Van Gerwin et al., "Nanoscaled Interdigitated Electrode Arrays for Biochemical Sensors," Sensors and Actuators B, vol. 49, pp. 73-80, (1998).

Van Megan et al., "Submicron Electrode Gaps Fabricated by Gold Electrodeposition at Interdigitated Electrodes," Key Engineering Materials, vol. 605, pp. 107-110, (2014).

Wang et al., "Electronics and Optoelectronics of Two-Dimensional Transition Metal Dichalcogenides," Nature Nanotechnology, vol. 7, pp. 699-712, (Nov. 6, 2012).

Xu et al., "Fabrication of Complex Metallic Nanostructures by Nanoskiving," American Chemical Society Nano, vol. 1(3), pp. 215-227, (2007).

Zafarani et al., "Electrochemical Redox Cycling in a New Nanogap Sensor: Design and Simulation," Journal of Electroanalytical Chemistry, vol. 760, pp. 42-47, (2015).

USPTO; Notice of Allowance dated May 11, 2020 in U.S. Appl. No. 16/073,706.

USPTO; Notice of Allowance dated Jun. 1, 2020 in U.S. Appl. No. 16/076,673.

USPTO; Non-Final Office Action dated Jun. 2, 2020 in U.S. Appl. No. 16/684,338.

USPTO; Non-Final Office Action dated Jun. 15, 2020 in U.S. Appl. No. 16/878,484.

USPTO; Non-Final Office Action dated Jun. 30, 2020 in U.S. Appl. No. 16/479,257.

USPTO; Non-Final Office Action dated Jun. 30, 2020 in U.S. Appl. No. 16/477,106.

EP; European Search Report dated Jun. 18, 2020 in Application No. 16815467.2.

CN; Office Action dated Jun. 5, 2020 in Chinese Patent Application No. 2017800204782.

EP; European Search Report dated Jun. 26, 2020 in Application No. 17874229.2.

Li et al., "Graphene Channel Liquid Container Field Effect Transistor as pH Sensor," Hindawi Publishing Corp., Journal of Nanomaterials 2014.

USPTO; Notice of Allowance dated Nov. 24, 2020 in U.S. Appl. No. 16/477,106.

USPTO; Notice of Allowance dated Dec. 7, 2020 in U.S. Appl. No. 16/878,484.

(56) References Cited

OTHER PUBLICATIONS

USPTO; Final Office Action dated Dec. 14, 2020 in U.S. Appl. No. 16/684,338.
USPTO; Final Office Action dated Jan. 6, 2021 in U.S. Appl. No. 16/070,133.
USPTO; Final Office Action dated Jan. 11, 2021 in U.S. Appl. No. 16/479,257.
USPTO; Non-Final Office Action dated Dec. 15, 2020 in U.S. Appl. No. 16/831,722.
USPTO; Non-Final Office Action dated Dec. 30, 2020 in U.S. Appl. No. 16/652,672.
EP; European Search Report dated Nov. 19, 2020 in Application No. 18739158.6.
JP; Office Action dated Dec. 2, 2020 in Japanese Patent Application No. 2018-536737.
EP; European Search Report dated Dec. 23, 2020 in Application No. 18790713.4.
EP; European Search Report dated Dec. 14, 2020 in Application No. 18799263.1.
Ali et al., "DNA hybridization detection using less than 10-nm gap silicon nanogap structure," Sensors and Actuators A. vol. 199, pp. 304-309 (2013).
Bornholt et al., "A DNA-Based Archival Storage System", Architectural Support for Programming Languages and Operating Systems, pp. 637-649 (2016).
Chen et al., "Silicon nanowire field-effect transistor-based biosensors for biomedical diagnosis and cellular recording investigation", Nano Today, Elsevier, Amsterdam, NL, vol. 6, No. 2, pp. 131-154 (2011).
Grass et al., "Robust Chemical Preservation of Digital Information on DNA in Silica with Error-Correcting Codes", Angewandte Chemie International Edition, vol. 54, No. 8, pp. 2552-2555 (2015).
Hatcher et al., "PNA versus DNA: Effects of Structural Fluctuations on Electronic Structure and Hole-Transport Mechanisms," J. Amer. Chem. Soc., 130, pp. 11752-11761 (2008).
Korlach et al., "Real-time DNA sequencing from single polymerase molecules," 11, Methods in Enzymology, Academy Press, vol. 472, pp. 431-455 (2010).
Paul et al., "Charge transfer through Single-Stranded Peptide Nucleic Acid Composed of Thymine Nucleotides," J. Phy. Chem. C 2008, 112, pp. 7233-7240 (2008).
Shin et al., "Distance Dependence of Electron Transfer Across Peptides with Different Secondary Structures: The Role of Peptide Energetics and Electronic Coupling," J. Amer. Chem. Soc. 2003, 125, pp. 3722-3732 (2003).
Venkatramani et al., "Nucleic Acid Charge Transfer: Black, White and Gray," Coard Chem Rev., 255(7-8): pp. 635-648 (2011).
USPTO; Non-Final Office Action dated Oct. 2, 2020 in U.S. Appl. No. 16/073,693.
USPTO; Non-Final Office Action dated Nov. 9, 2020 in U.S. Appl. No. 16/731,749.
PCT; International Search Report and Written Opinion dated Jun. 9, 2020 in Application No. PCT/US2020/13218.
PCT; International Search Report and Written Opinion dated Aug. 6, 2020 in Application No. PCT/US2020/25068.
PCT; International Search Report and Written Opinion dated Sep. 4, 2020 in Application No. PCT/US2020/28004.
EP; European Search Report dated Sep. 30, 2020 in Application No. 17893481.6.
JP; Office Action dated Aug. 13, 2020 in Japanese Application No. 2017-566864.
CN; Office Action dated Aug. 14, 2020 in Chinese Patent Application No. 201680083636.4.
Yang et al., "Two-Dimensional Graphene Nanoribbons," J. Am. Chem. Soc. vol. 130, Issue 13 (2008).

* cited by examiner

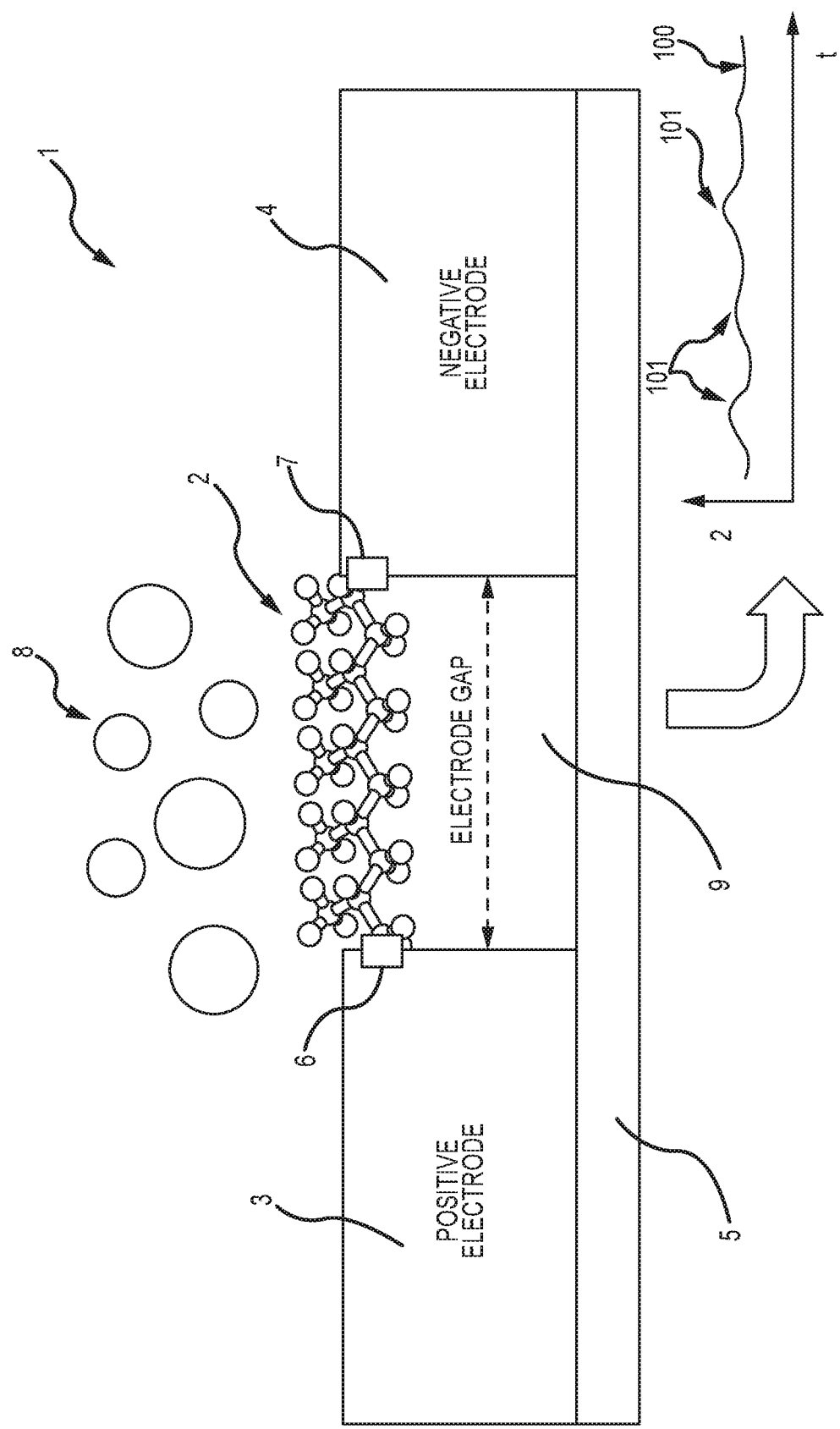
FIG.1-A

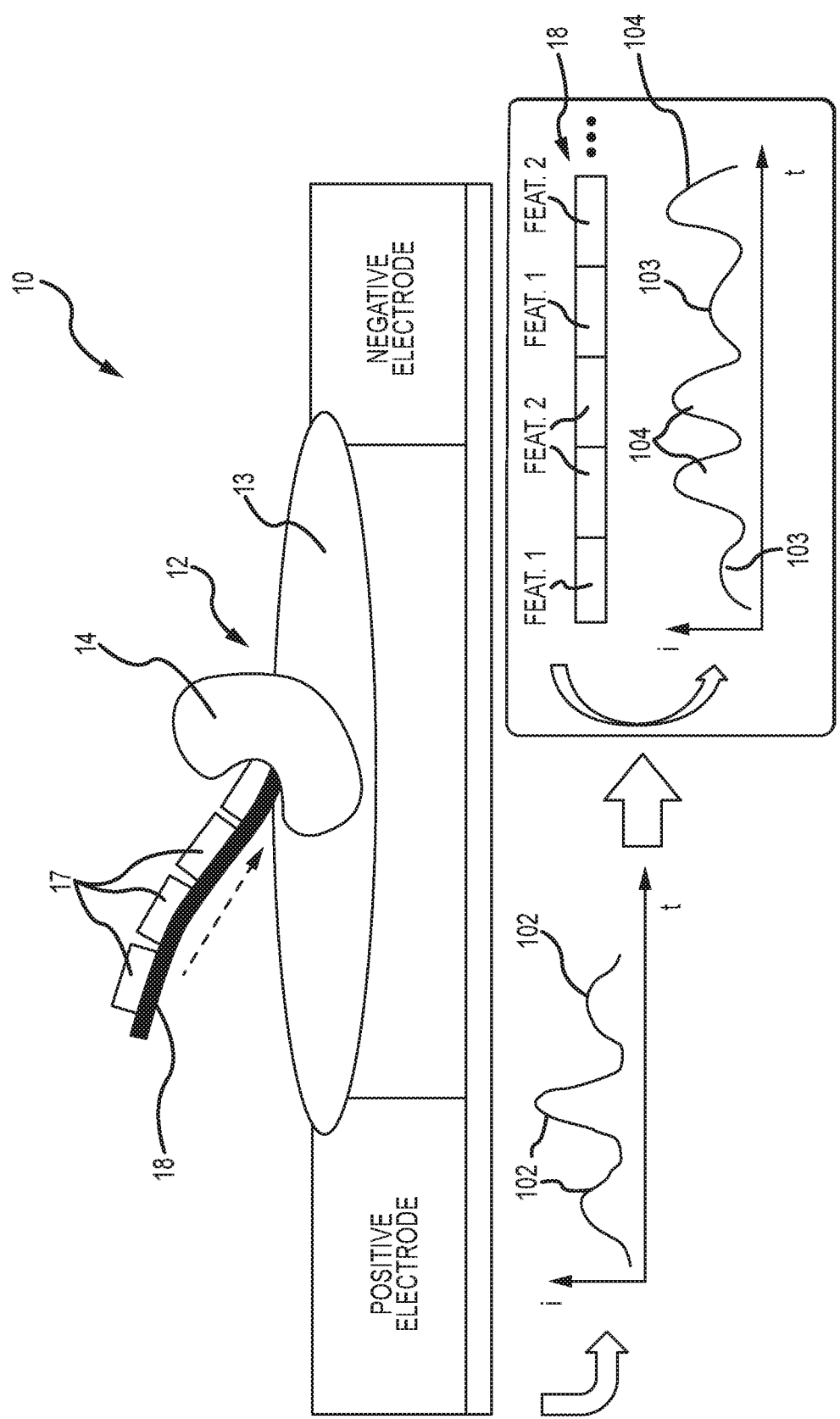
FIG. 1-B

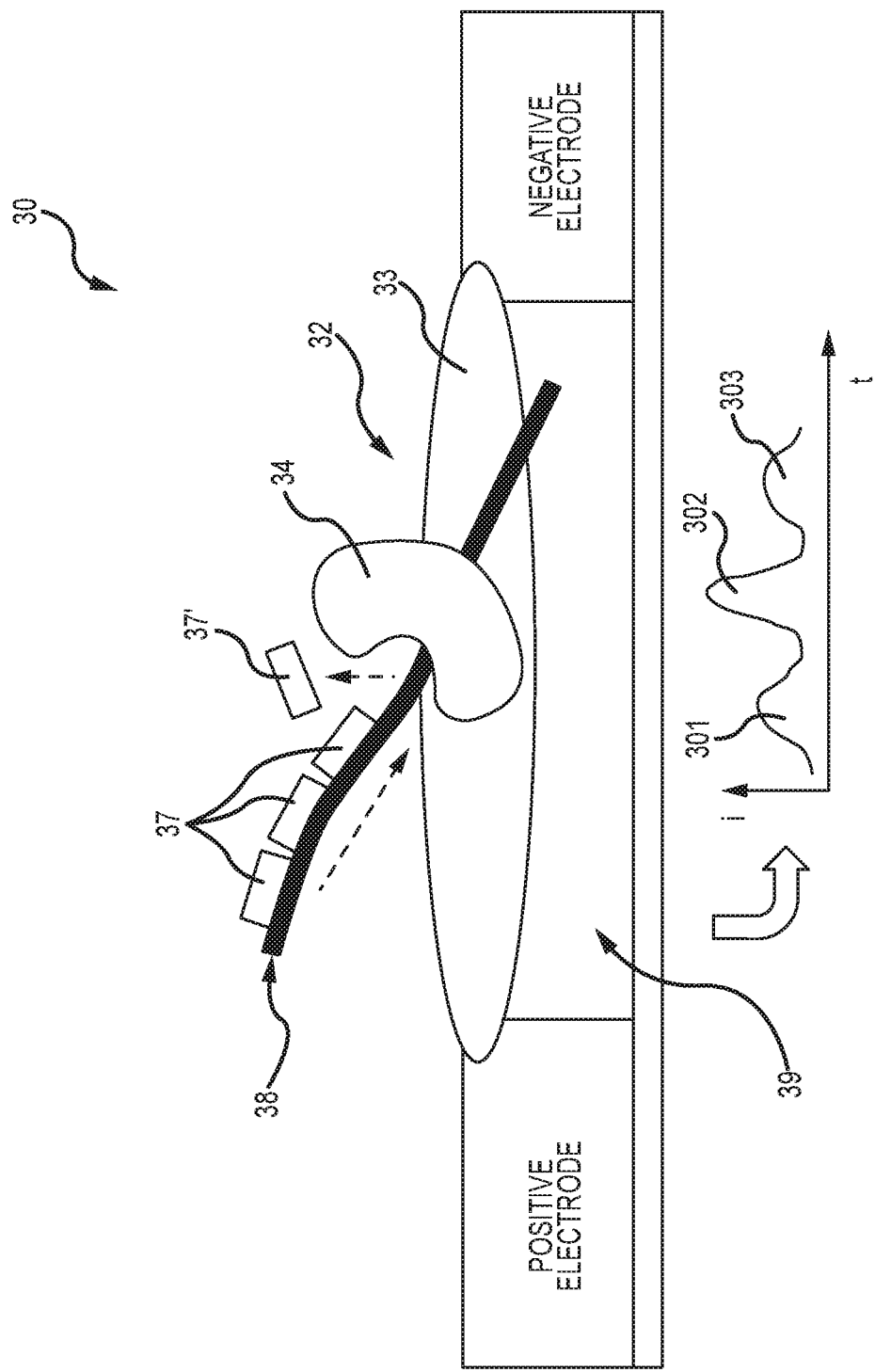
FIG.3-A

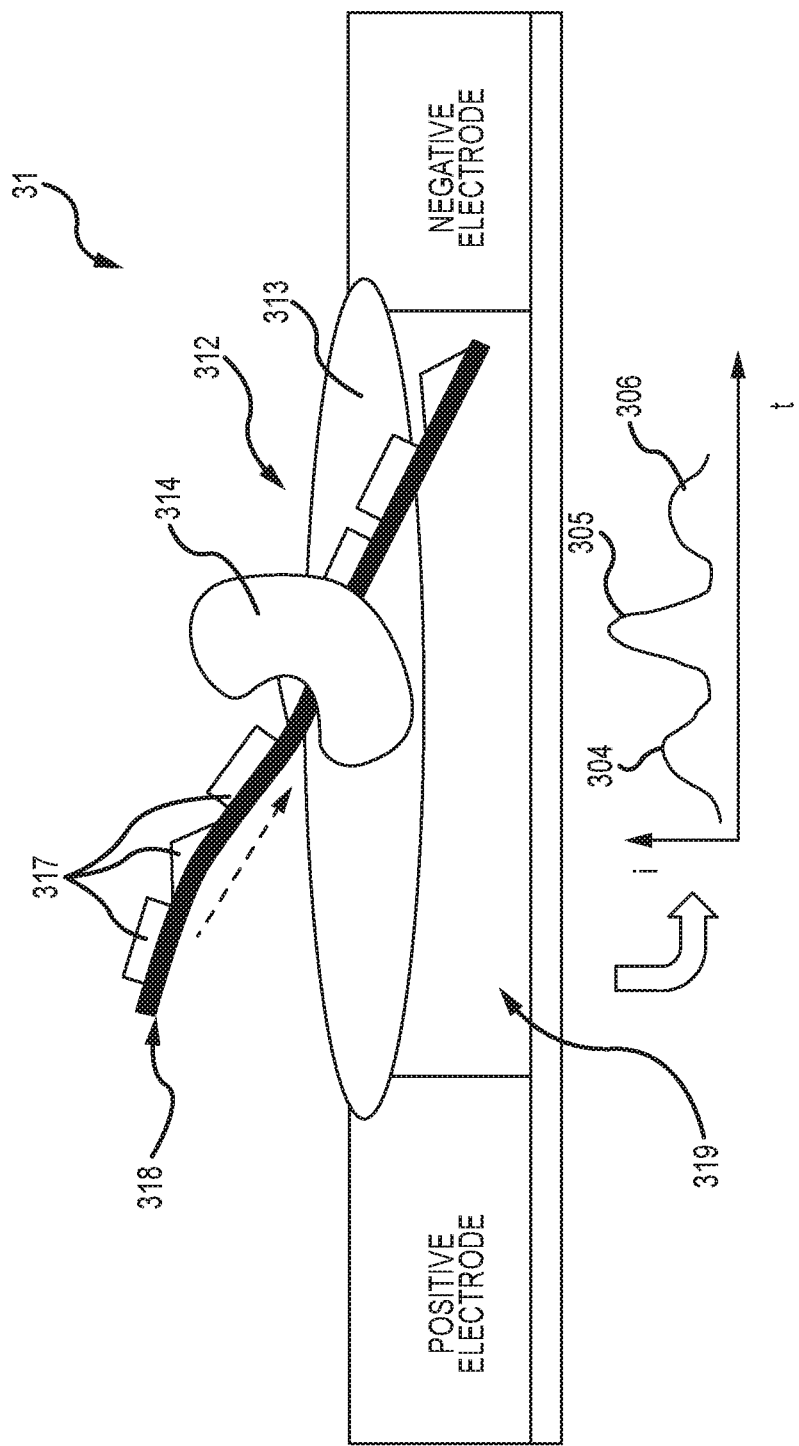
FIG.3-B

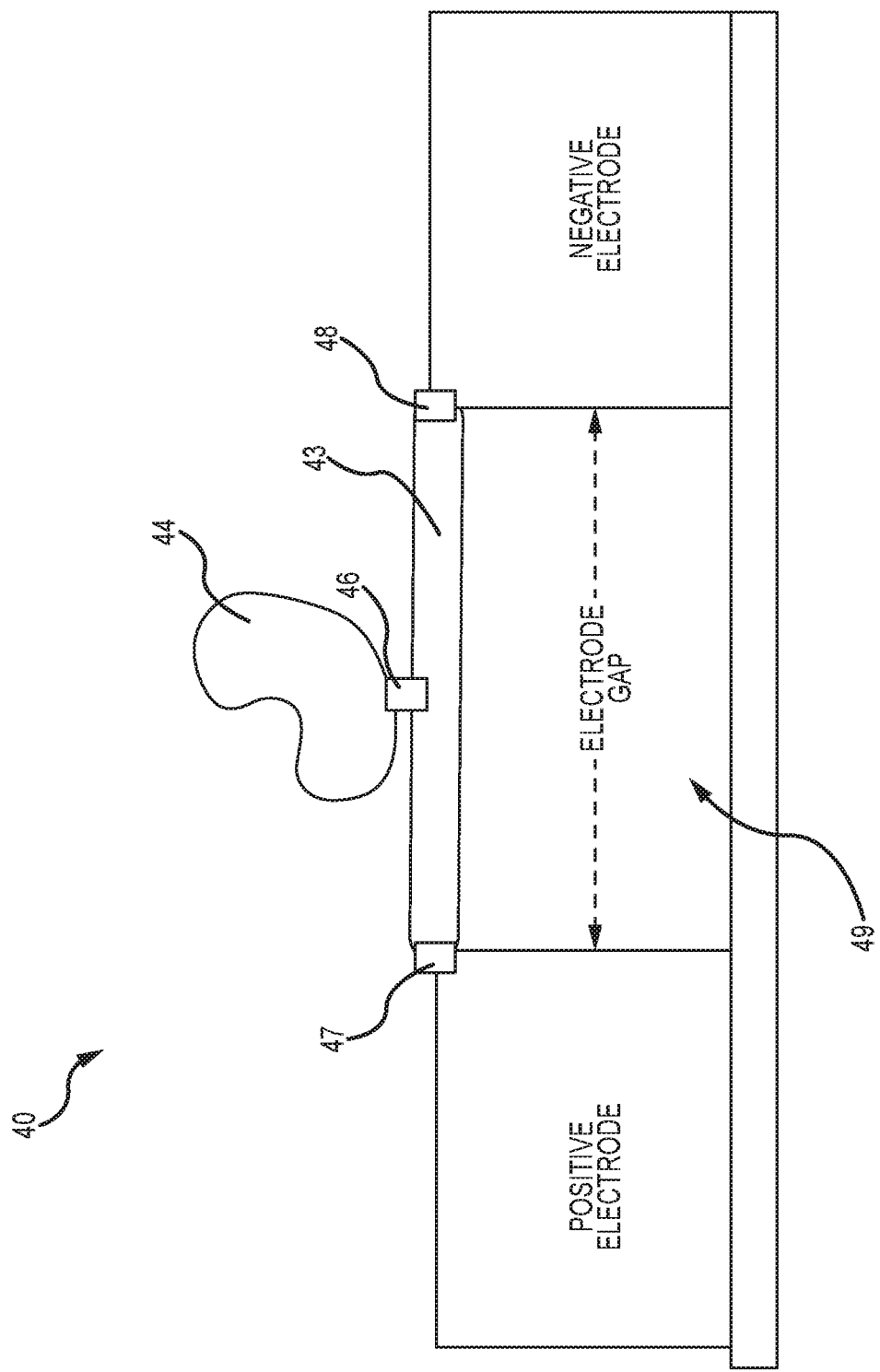
FIG.4-A

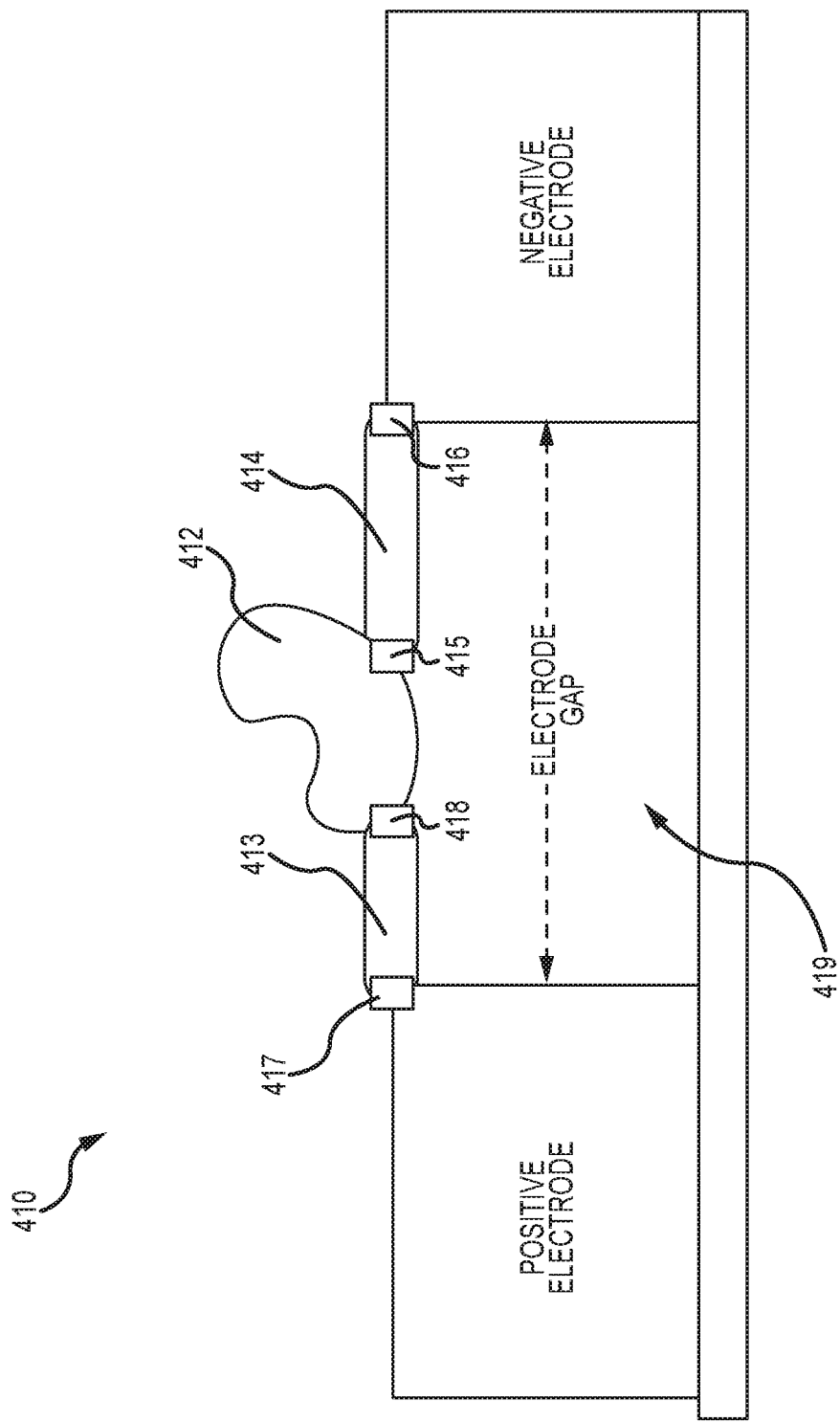
FIG. 4-B

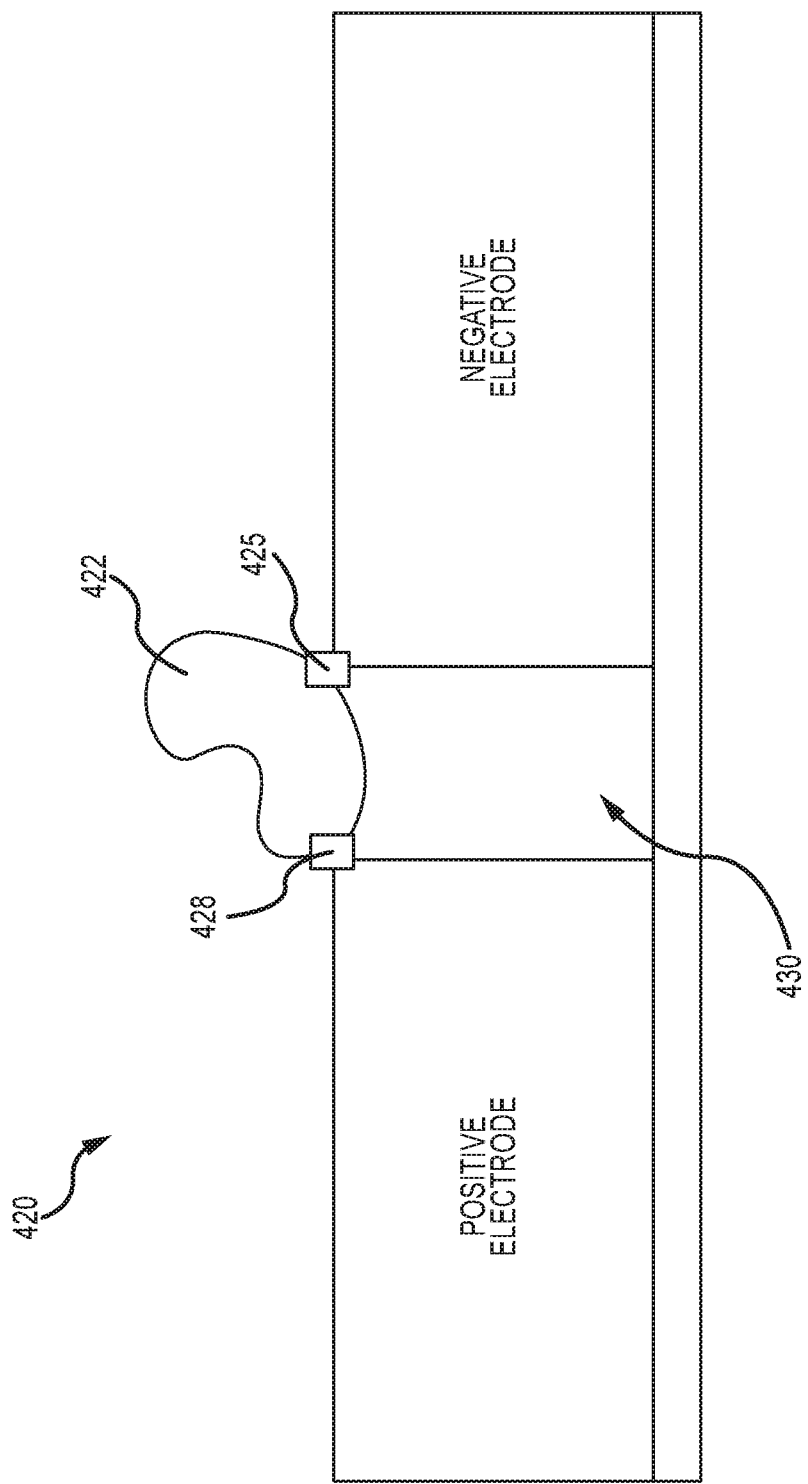

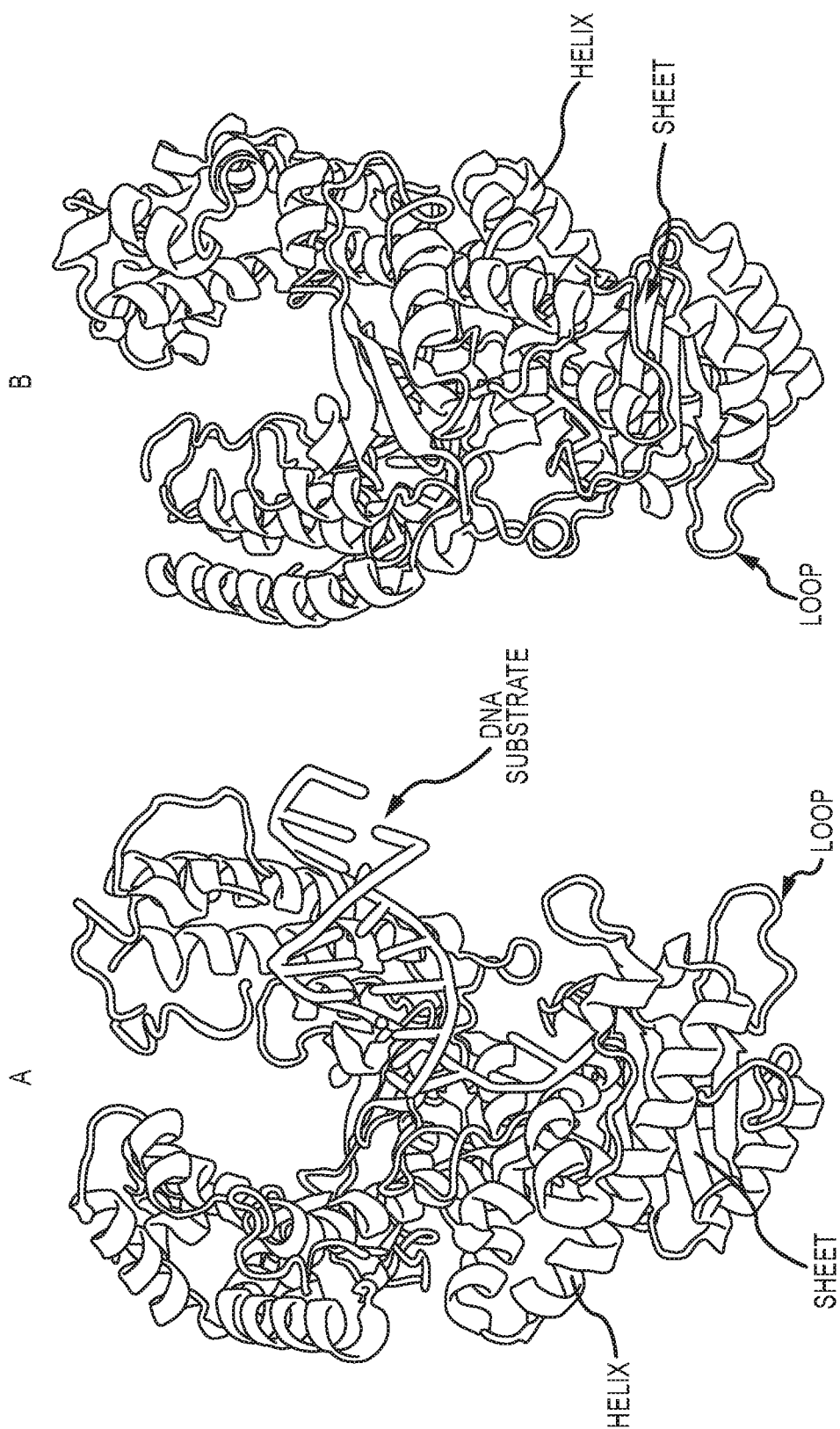
FIG.12-A

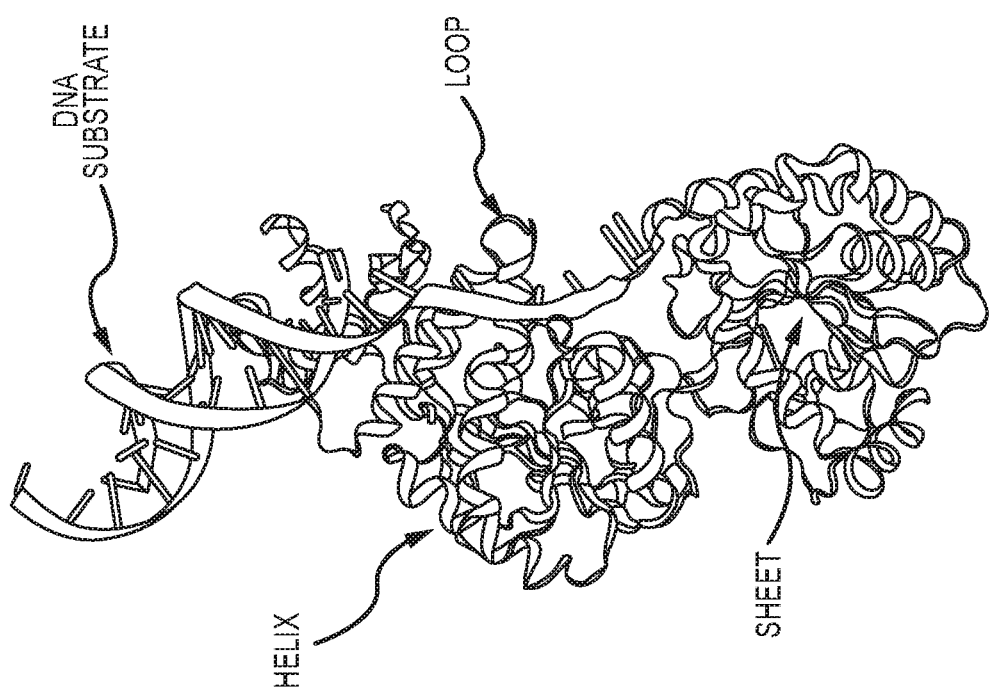
FIG. 12-B

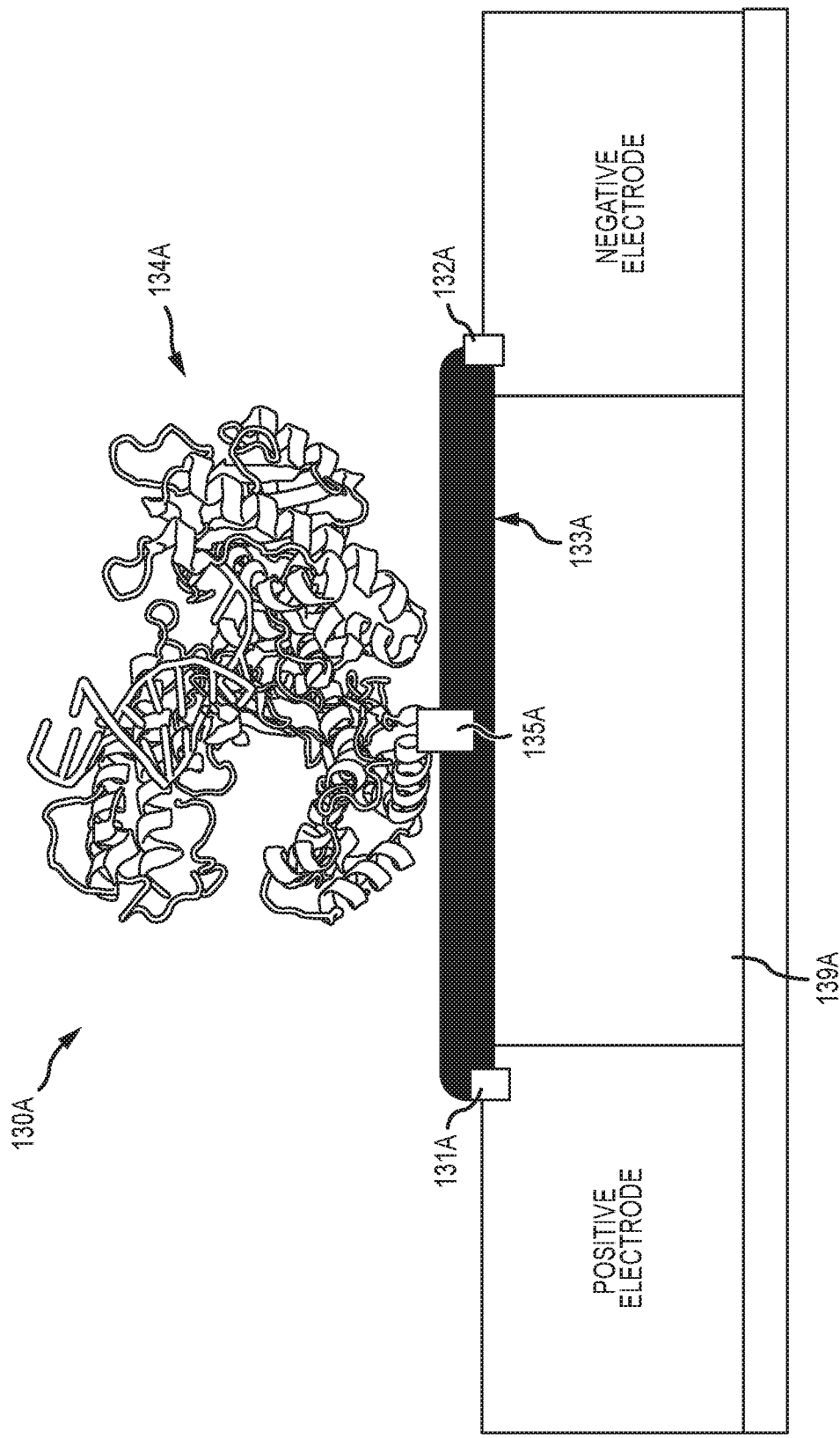
FIG. 13-A

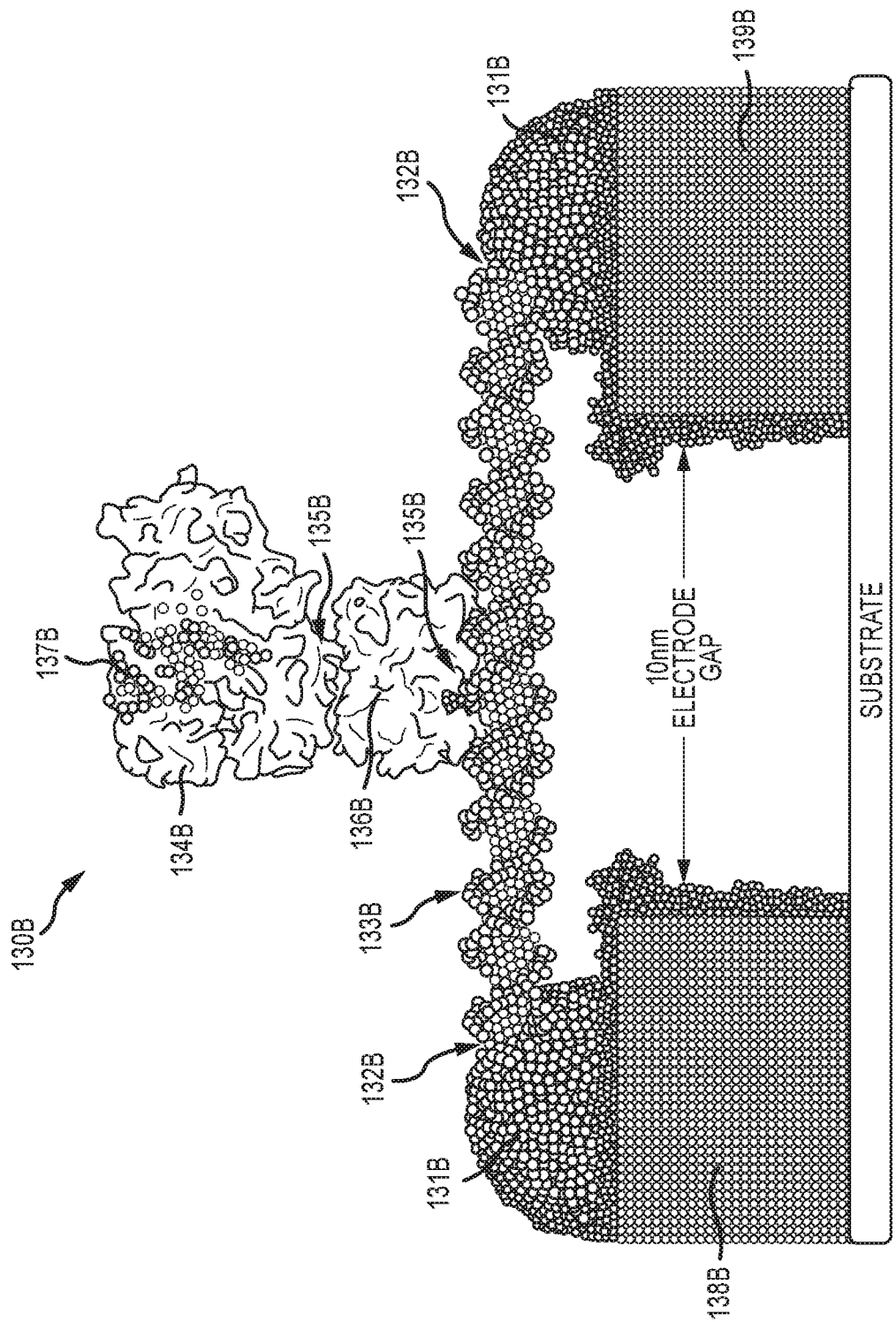
FIG.13-B

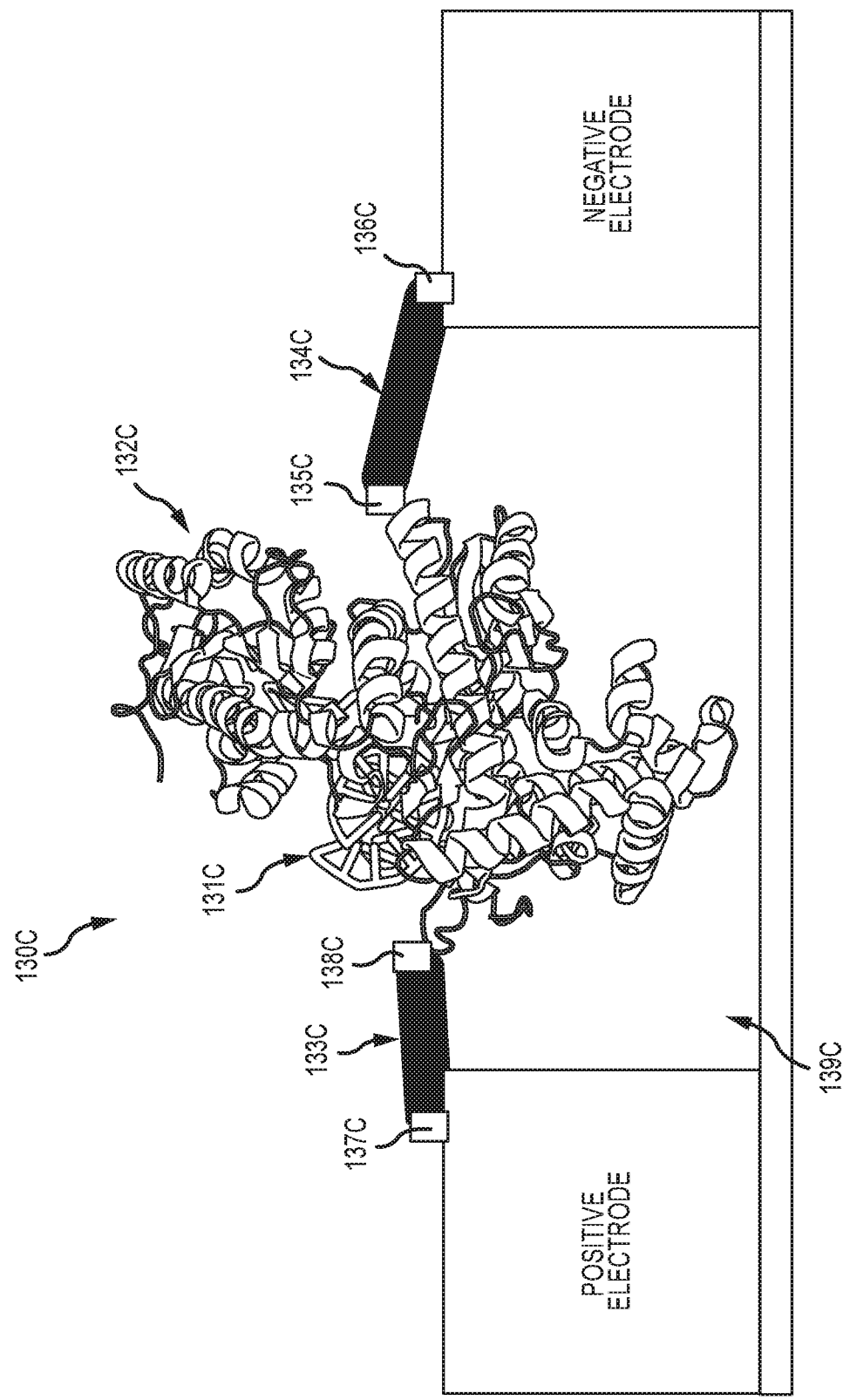
FIG.13-C

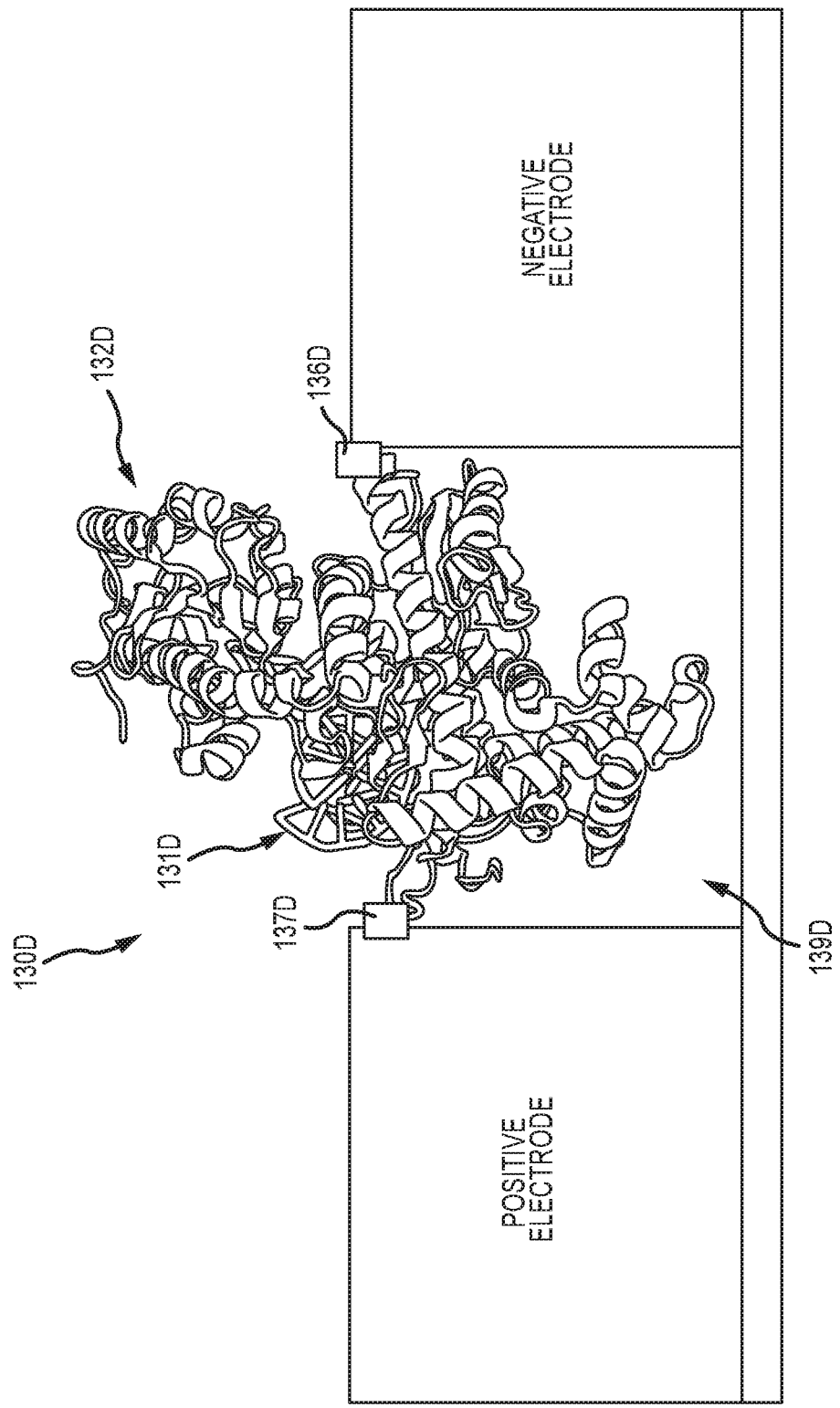

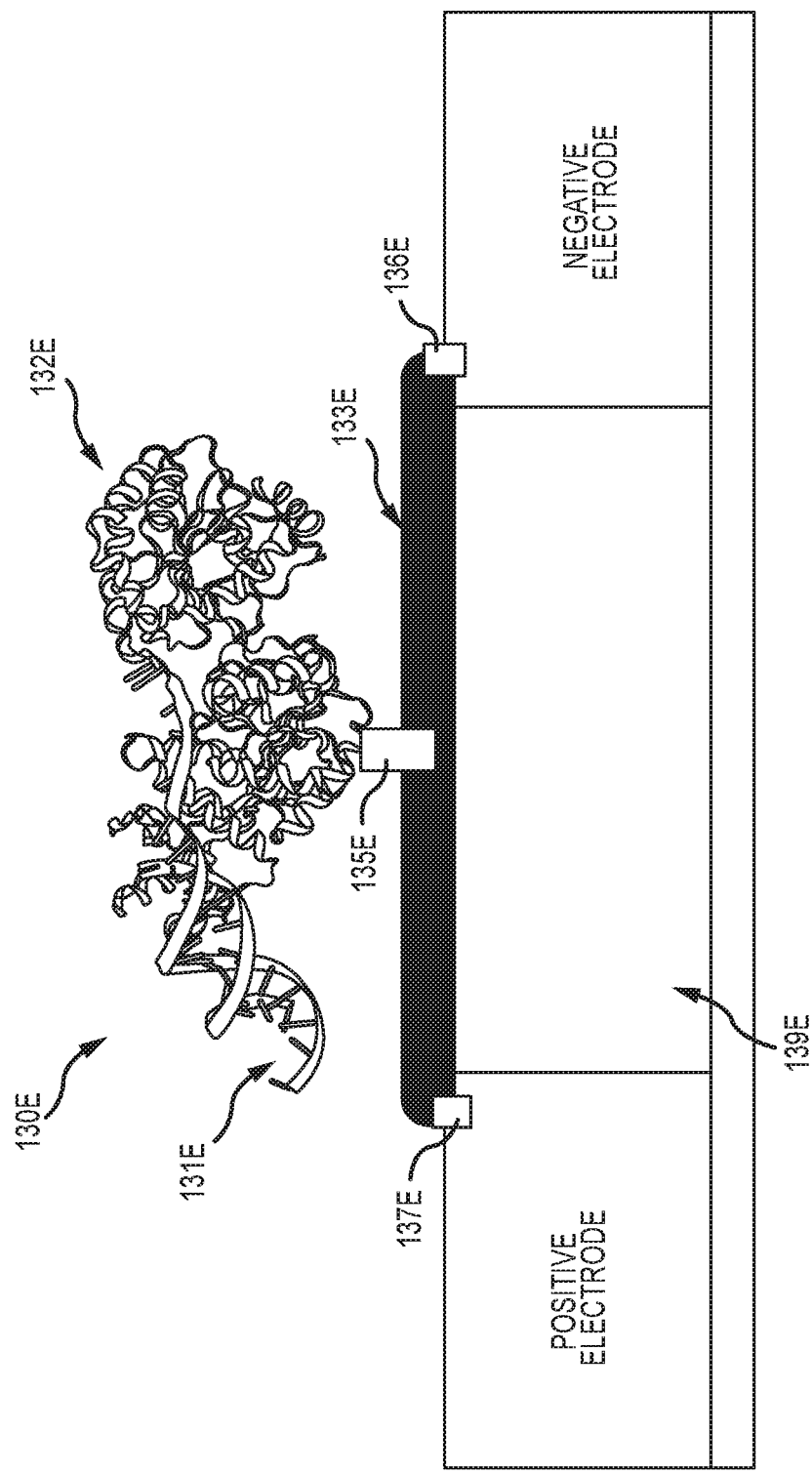
FIG.13-E

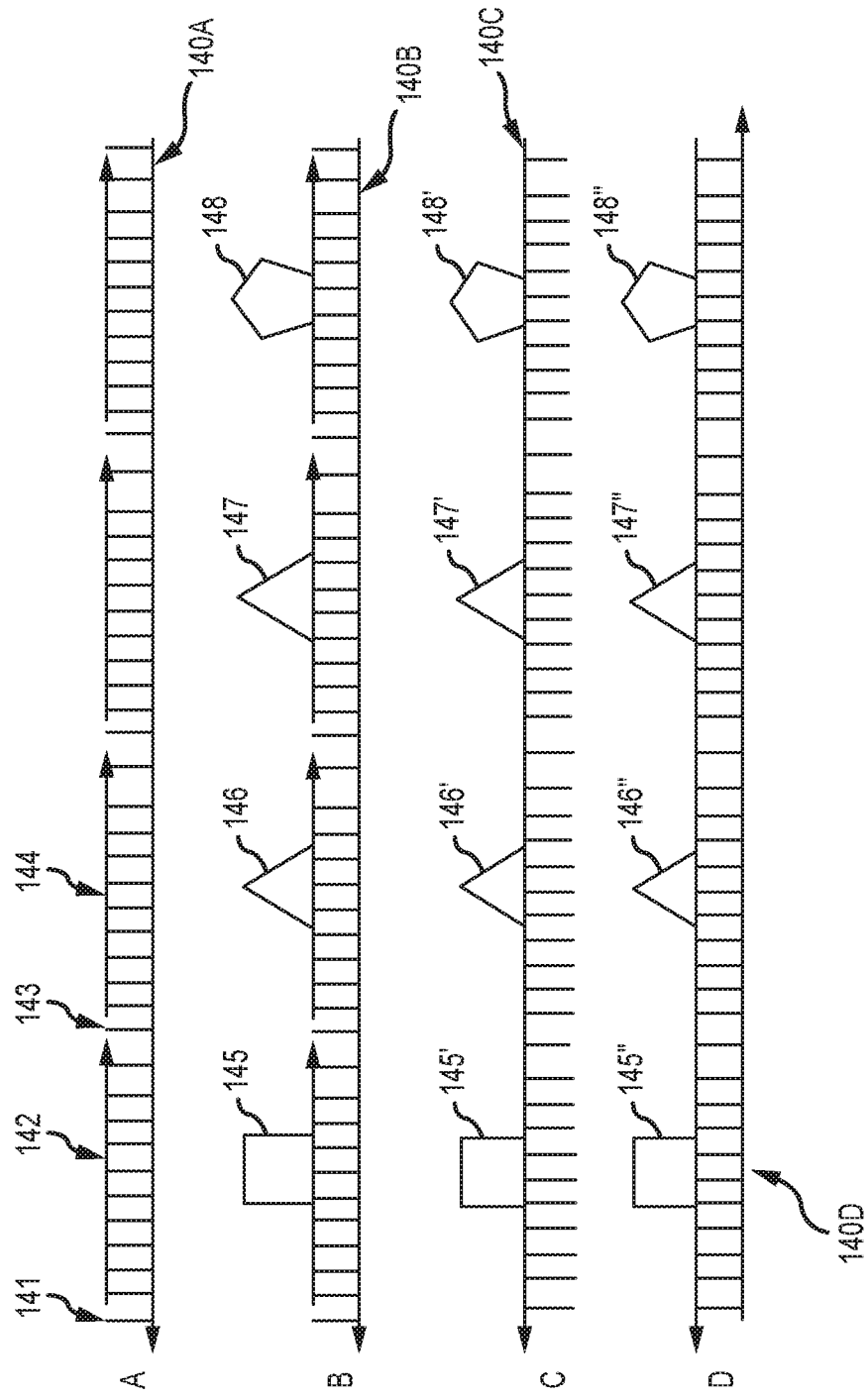

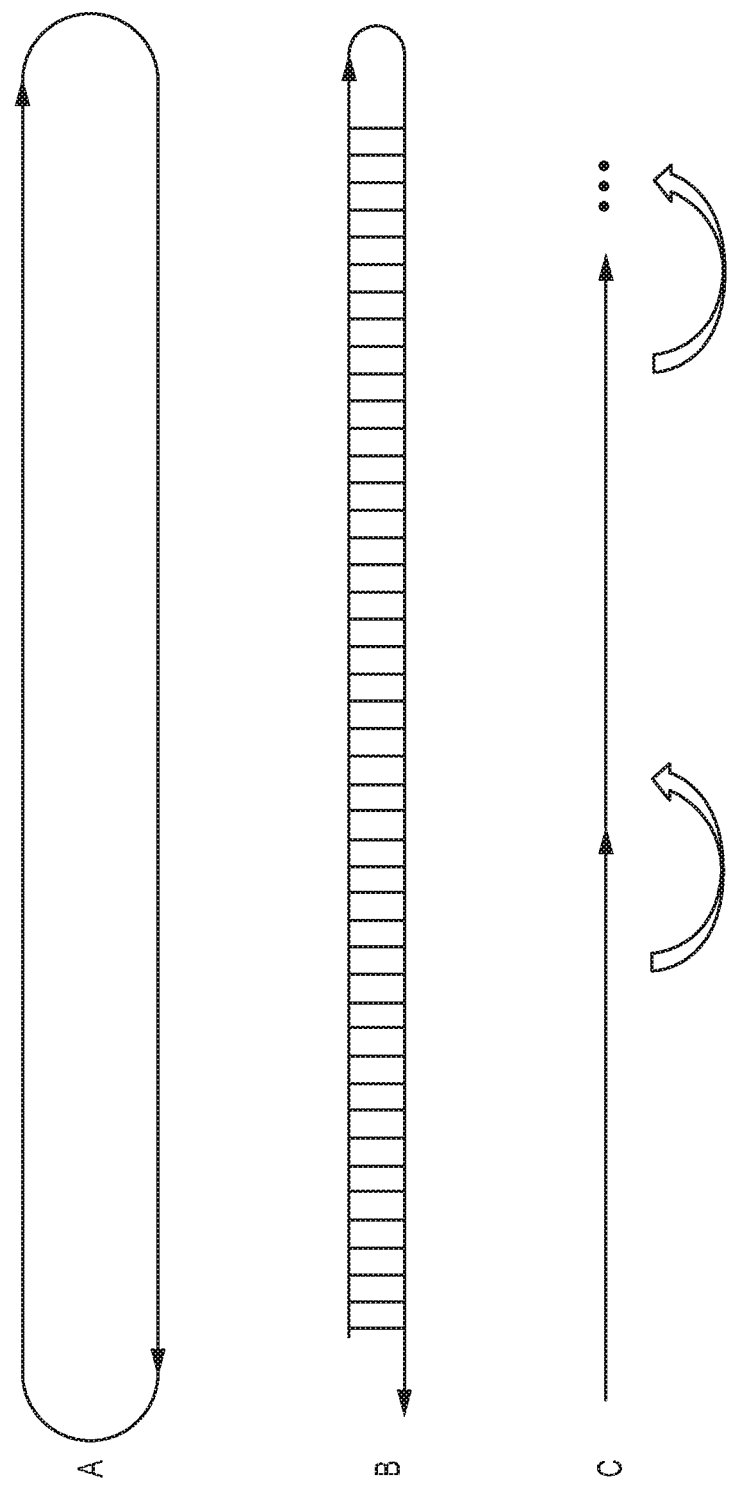

EXAMPLE BINARY DATA PAYLOAD   1010100110011100

EXAMPLE BINARY ENCODING SCHEMES (BES)

BES1            BES2            BES3

0 → F1          00 → F1         0 → F1
1 → F2          01 → F2         1 → F2
                10 → F3         00 → F3
                11 → F4

BES1  1 0 1 0 1 0 0 1 1 0 0 1 1 1 0 0
      F2F1F2F1F2F1F1F2F2F1F1F2F2F1F1F1

BES2  10101001100111 00
      F3F3F3F2F3F2F4F1

BES3  1 0 1 0 1 00 1 1 00 1 1 1 00
      F2F1F2F1F2F3 F2F2F3 F2F2F2F3

FIG.16

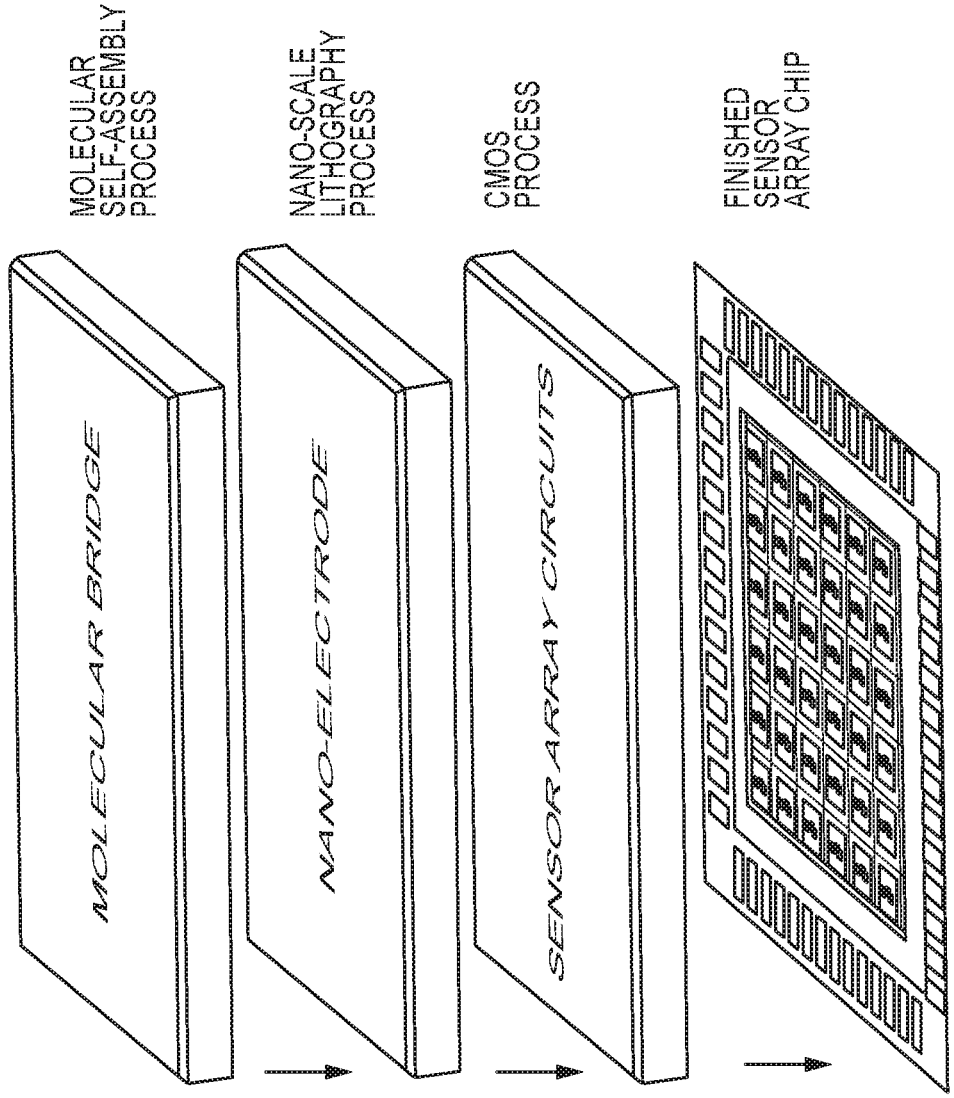
FIG. 17-A

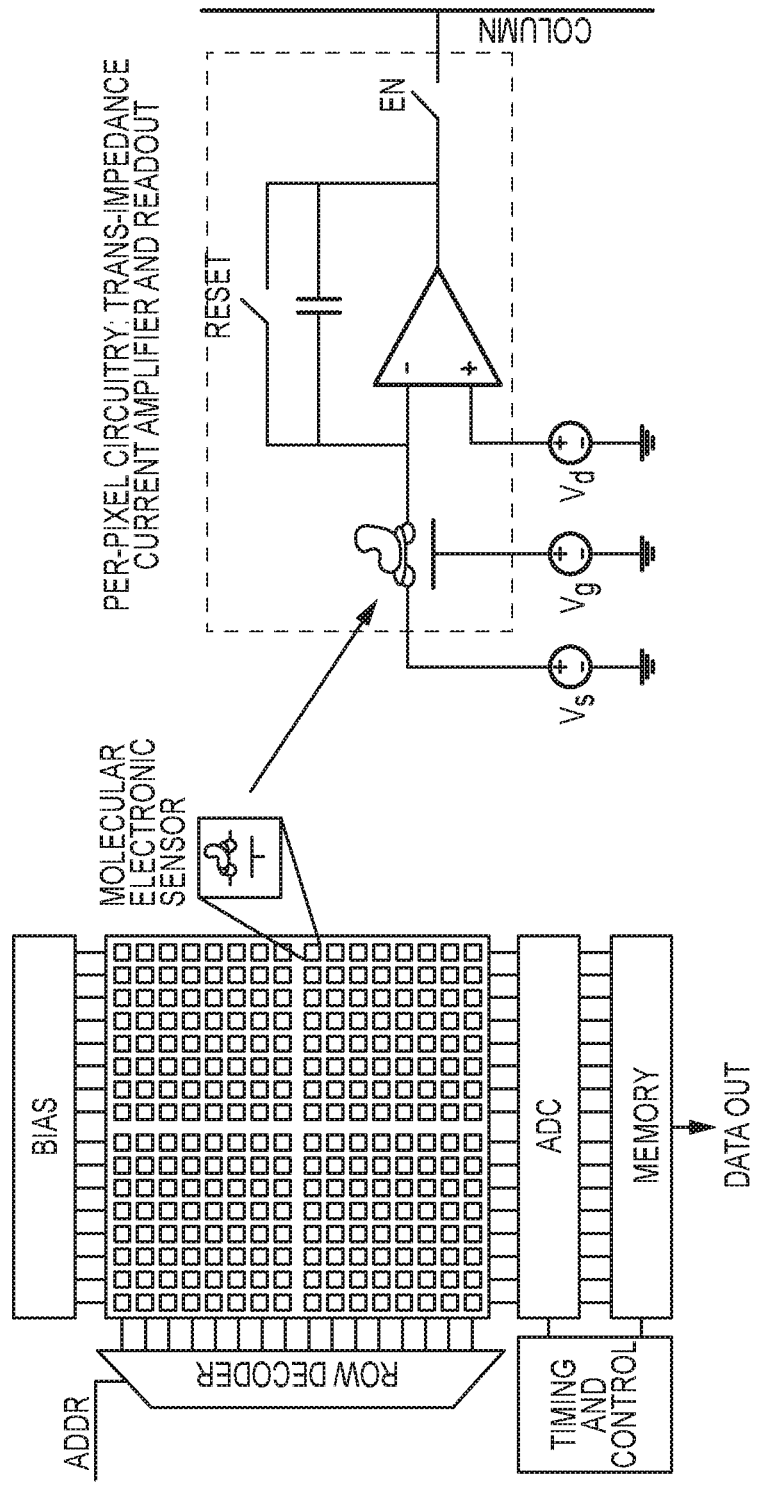
FIG. 17-B

PROCESSIVE ENZYME MOLECULAR ELECTRONIC SENSORS FOR DNA DATA STORAGE

CROSS-REFERENCE TO RELATED APPLICATIONS

This application claims priority to and the benefit of U.S. Provisional Patent Application Ser. No. 62/551,977 filed Aug. 30, 2017, entitled "Processive Enzyme Molecular Electronic Sensors for DNA Data Storage," the disclosure of which is incorporated herein by reference in its entirety for all purposes.

FIELD

The present disclosure generally relates to electronic data storage and retrieval, and more particularly to DNA information and retrieval systems comprising molecular electronic sensors for reading information stored as DNA molecules.

BACKGROUND

The advent of digital computing in the 20$^{th}$ Century created the need for archival storage of large amounts of digital or binary data. Archival storage is intended to house large amounts of data for long periods of time, e.g., years, decades or longer, in a way that is very low cost, and that supports the rare need to re-access the data. Although an archival storage system may feature the ability to hold unlimited amounts of data at very low cost, such as through a physical storage medium able to remain dormant for long periods of time, the data writing and recovery processes in such a system can be relatively slow or otherwise costly. The dominant forms of archival digital data storage developed to date include magnetic tape, and, more recently, compact optical disc (CD). However, as data production grows, there is a need for even higher density, lower cost, and longer lasting archival digital data storage systems.

It has been observed that in biology, the genomic DNA of a living organism functions as a form of digital information archival storage. On the timescale of the existence of a species, which may extend for thousands to millions of years, the genomic DNA in effect stores the genetic biological information that defines the species. The complex enzymatic, biochemical processes embodied in the biology, reproduction and survival of the species provide the means of writing, reading and maintaining this information archive. This observation has motivated the idea that perhaps the fundamental information storage capacity of DNA could be harnessed as the basis for high density, long duration archival storage of more general forms of digital information.

What makes DNA attractive for information storage is the extremely high information density resulting from molecular scale storage of information. In theory for example, all human-produced digital information recorded to date, estimated to be approximately 1 ZB (Zettabyte, $10^{21}$ bytes), could be recorded in less than $10^{22}$ DNA bases, or $\frac{1}{60}^{th}$ of a mole of DNA bases, which would have a mass of just 10 grams. In addition to high data density, DNA is also a very stable molecule, which can readily last for thousands of years without substantial damage, and which could potentially last far longer, for tens of thousands of years, or even millions of years, such as observed naturally with DNA frozen in permafrost or encased in amber.

SUMMARY

In various embodiments of the present disclosure, a data reader for use in a DNA data storage system is provided. In particular, a sensor is disclosed that can extract the digital information synthetically encoded into a single DNA molecule. As disclosed herein, sensors for use as DNA encoded data readers are processive enzyme molecular sensors. In various aspects, a plurality of such sensors are provided in an array in a high-density chip-based format that can provide the high throughput, low-cost and fast data extraction capability required for large scale DNA data storage systems. In various embodiments, the sensor for reading the digital data stored in DNA molecules processes individual encoded DNA molecules directly, so that there is no need for complicated sample preparation such as making copies of DNA or clonal populations of such molecules.

In various aspects, the fundamental time required to extract information encoded in a DNA molecule is short, on the order of seconds, which fundamentally enables short turn-around times for data recovery. Information extraction from a DNA molecule is at the rate of a processive enzyme acting on DNA, which can be very fast, as short as fractions of a second. In various aspects, information can be encoded in native DNA, without modifications, which can be replicated, copied or amplified as needed. Further, simple means to enhance the signal-to-noise ratio are disclosed. The sensor can be deployed in a highly scalable, low cost, CMOS chip format, providing for efficient mass manufacturing, and low cost systems and instruments, and overall low costs for reading digital data stored in DNA. The systems and instruments required to read Exabyte-scale digital data from DNA data can be highly compact and energy efficient, to support practical, robust deployment both locally at on-site data centers, and for highly scalable cloud-based archival data storage services. Sensors for information extraction herein provide for systems that read data stored in DNA that can exceed the performance, in speed, throughput and cost, of the respective reader systems for data archived in conventional archival storage formats such as magnetic tape or optical discs. The present disclosure provides enabling technology for DNA digital data storage systems capable of practical Exabyte scale storage, and Zettabyte scale storage.

In various embodiments of the present disclosure, a sensor is disclosed. In various aspects the sensor comprises a processive enzyme molecular electronics sensor. In various examples the sensor comprises: a first electrode; a second electrode spaced apart from the first electrode by an electrode gap; a processive enzyme conjugated to the first and second electrodes, the processive enzyme comprising a native or genetically engineered polymerase, reverse transcriptase, helicase, exonuclease, or molecular motor for packaging of viral DNA; and a trans-impedance amplifier electrically connected to at least one of the first electrode and second electrode, the trans-impedance amplifier providing an output comprising a measurable electrical parameter; wherein the measurable electrical parameter comprises distinguishable signals corresponding to enzymatic activity of the processive enzyme.

In various aspects of a sensor, the trans-impedance amplifier provides a biasable voltage across the first and second electrodes, and the measurable electrical parameter comprises a current output.

In various aspects of a sensor, the sensor may further comprise a gate electrode capacitively coupled to the electrode gap.

In various aspects of a sensor, the trans-impedance amplifier may further provide a biasable voltage to the gate electrode when a gate electrode is utilized in the sensor. In various aspects of a sensor, the processive enzyme is directly wired between first and second electrodes to provide a conductive pathway between the first and second electrodes, through the processive enzyme. For direct wiring, two sites on the enzyme molecule, such as two amino acid residues, may be modified to promote direct chemical bonding of each site to the first and second electrodes.

In various aspects of a sensor, the processive enzyme is conjugated to the first and second electrodes via a bridge molecule spanning the electrode gap, the bridge molecule having first and second ends, the first end conjugated to the first electrode and the second end conjugated to the second electrode, wherein the processive enzyme is conjugated to the bridge molecule.

In various aspects of a sensor, the processive enzyme is conjugated to the first and second electrodes via at least one intervening arm molecule, the arm molecule conjugated to at least one of the first and second electrodes and conjugated to the processive enzyme.

In various aspects of a sensor, bridge or arm molecules may comprise a double stranded DNA, a protein alpha helix, a graphene nanoribbon, a carbon nanotube, an antibody, or a Fab arm of an antibody.

In various aspects of a sensor, the first and second electrodes comprise source and drain electrodes, respectively, and wherein the measurable electrical parameter is the source-drain current between the electrodes.

In various aspects of a sensor, the trans-impedance amplifier further provides for voltage-biasable source, drain and gate electrodes.

In various embodiments of the present disclosure, a method of reading encoded information is disclosed. The method comprises: translocating a synthetic DNA molecule through a processive enzyme, where the processive enzyme is electrically connected in a molecular sensor circuit; and generating signals in a measureable electrical parameter of the circuit, wherein the signals correspond to the encoded information.

In various aspects of a method, the processive enzyme comprises a native or genetically engineered polymerase, reverse transcriptase, helicase, exonuclease, or molecular motor for packaging of viral DNA.

In various aspects of a method, the encoded information comprises binary data.

In various aspects of a method, the synthetic DNA molecule comprises a DNA template strand with distinguishable signaling features bonded thereon.

In various aspects of a method, the distinguishable signaling features comprise a sequence of oligonucleotides.

In various aspects of a method, the oligonucleotides are bonded to the DNA template strand by complementary base pairing and the oligonucleotides are displaced from the DNA template strand by the processive enzyme as the synthetic DNA molecule processively translocates through the processive enzyme, encountering the oligonucleotides. In these examples, a signal in the measureable electrical parameter of the circuit corresponds to displacement of an oligonucleotide from the DNA template strand.

In various aspects of a method, each of the oligonucleotides further comprises at least one chemical group bonded thereon.

In various aspects of a method, the oligonucleotides are covalently bonded to the DNA template strand, wherein a distinguishable signal in the measurable electrical parameter of the circuit corresponds to interaction of an oligonucleotide with the processive enzyme without displacement of the oligonucleotide from the DNA template strand.

In various aspects of a method, each of the oligonucleotides further comprises at least one chemical group bonded thereon.

In various aspects of a method, the distinguishable signaling features comprise chemical groups conjugated to the DNA template strand.

In various embodiments of the present disclosure, a DNA information system is disclosed. The system comprises: a synthetic DNA molecule comprising a DNA template strand and distinguishable signaling features bonded thereon, the distinguishable signaling features encoding information in the synthetic DNA molecule; a buffer solution in contact with the synthetic DNA molecule, the first and second electrodes, and the processive enzyme; and a sensor capable of reading the information encoded in the synthetic DNA molecule, the sensor comprising: a first electrode; a second electrode spaced apart from the first electrode by an electrode gap; a processive enzyme conjugated to both the first and second electrodes; and a trans-impedance amplifier electrically connected to at least one of the first and second electrodes, the trans-impedance amplifier providing an output comprising a measurable electrical parameter, wherein the measurable electrical parameter comprises distinguishable signals corresponding to the encoded information.

In various aspects of a system, the processive enzyme comprises a native or genetically engineered polymerase, reverse transcriptase, helicase, exonuclease, or molecular motor for packaging of viral DNA.

In various aspects of a system, the encoded information comprises binary data.

In various aspects of a system, the distinguishable signaling features comprise a sequence of oligonucleotides.

In various aspects of a system, the oligonucleotides are bonded to the DNA template strand by complementary base pairing, or the oligonucleotides are covalently bonded to the DNA template strand. In certain aspects, combinations of base-paired oligonucleotides and covalently bound oligonucleotides encode the information in the synthetic DNA molecule. In certain aspects, base-paired oligonucleotides are displaced from the DNA template strand by the processive enzyme, whereas covalently bonded oligonucleotides are not displaced when the processive enzyme encounters them.

In various aspects of a system, each of the oligonucleotides further comprises at least one chemical group bonded thereon. In other examples, at least one oligonucleotide in a sequence of oligonucleotides bonded to the DNA template strand comprise a chemical group bonded thereon.

In various aspects of a system, the distinguishable signaling features comprise chemical groups conjugated to the DNA template strand.

In various aspects of a system, the system further comprises a reference electrode submerged in the buffer solution. The reference may be, for example, a Ag/AgCl electrode.

In various aspects of a system, the system further comprises a gate electrode capacitively coupled to the electrode gap.

In various aspects of a system, the processive enzyme is directly wired between first and second electrodes to provide a conductive pathway between first and second electrodes, through the processive enzyme.

In various aspects of a system, the processive enzyme is conjugated to the first and second electrodes via a bridge molecule spanning the electrode gap, the bridge molecule having first and second ends, the first end conjugated to the first electrode and the second end conjugated to the second electrode, wherein the processive enzyme is conjugated to the bridge molecule.

In various aspects of a system, the processive enzyme is conjugated to the first and second electrodes via at least one intervening arm molecule, the arm molecule conjugated to at least one of the first and second electrodes and conjugated to the processive enzyme.

In various aspects of a system, bridge or arm molecules may comprise a double stranded DNA, a protein alpha helix, a graphene nanoribbon, a carbon nanotube, an antibody, or a Fab arm of an antibody.

In various aspects of a system, the system further comprises a CMOS sensor array chip comprising an array of the sensors and supporting pixel circuitry that performs measurement of the measurable electrical parameter.

In various aspects of a system, the system comprises at least two of the CMOS sensor array chips; an electronic hardware system for controlling and managing electrical inputs and data outputs of the chips; a fluidic system for introducing the synthetic DNA molecule in the buffer solution to the chips; and a signal processing and data recording system for capturing the distinguishable signals and for converting the distinguishable signals back to the information.

In various aspects of a system, the synthetic DNA molecule comprises a circular, hairpin, or tandem repeat architecture that allows repeat reading of the information encoded in the synthetic DNA molecule.

BRIEF DESCRIPTION OF THE DRAWINGS

The subject matter of the present disclosure is particularly pointed out and distinctly claimed in the concluding portion of the specification. A more complete understanding of the present disclosure, however, may best be obtained by referring to the detailed description and claims when considered in connection with the drawing figures:

FIG. 1-A shows an embodiment of a molecular electronic sensing circuit, in which a molecule completes an electrical circuit, an electrical circuit parameter is measured versus time for signals, where the recorded signals correspond to interactions of the molecule with interacting molecules in the surrounding environment;

FIG. 1-B shows an embodiment of a processive enzyme molecular electronics sensor that can be used to read data encoded into synthetic DNA molecules. The sensor produces distinguishable signals corresponding to distinct signaling features structurally present on a template DNA molecule; such feature elements can be used to encode information into synthetic template DNA molecules, which can in turn be read via the sensor;

FIG. 3-A shows an embodiment of a processive enzyme molecular sensor in the process of reading DNA, in which groups bound to the template DNA are displaced by the action of the processive enzyme, with the displacement events resulting in distinguishable signal features;

FIG. 3-B shows an embodiment of a processive enzyme molecular sensor in the process of reading DNA, in which the template DNA has modifying groups attached, and as the processive enzyme translocates past these features, it results in the production of distinguishable signal features;

FIG. 4-A shows an embodiment of a processive enzyme molecular sensor comprising a processive enzyme molecule conjugated to a bridge molecule that spans the gap between two electrodes, conjugated to each electrode;

FIG. 4-B shows an embodiment of a processive enzyme molecular sensor comprising a processive enzyme molecule wired directly into the current path of the sensor by way of two arm molecules providing the connections to the electrodes;

FIG. 4-C shows an embodiment of a processive enzyme molecular sensor, wherein the processive enzyme molecule is directly conjugated to the electrodes without any intervening arm molecules or a bridge molecule in the circuit;

FIG. 12-A shows the detailed protein structure of one specific processive enzyme molecule, a polymerase comprising the Klenow Fragment of E. Coli. Polymerase I, with (A) and without (B) a DNA substrate interacting with the polymerase;

FIG. 12-B shows the detailed protein structure of one specific processive enzyme molecule, a helicase comprising the human RECQ-like DNA helicase while interacting with a DNA substrate molecule;

FIG. 13-A shows embodiments of a processive enzyme molecular electronic sensor, wherein the polymerase processive enzyme molecule is conjugated to a bridge molecule bonded between the electrodes;

FIG. 13-B shows an embodiment of the processive enzyme molecular electronic sensor of FIG. 13-A, wherein the bridge molecule comprises a double stranded DNA, the polymerase-bridge conjugation comprises biotin-streptavidin binding, and the electrodes comprise gold-on-chromium to support thiol-gold binding of first and second ends of the bridge molecule to the electrodes;

FIG. 13-C shows an embodiment of a processive enzyme molecular electronic sensor, wherein the polymerase processive enzyme is conjugated directly into the current path by use of two arm molecules between the enzyme and each of the two electrodes;

FIG. 13-D shows embodiments of a processive enzyme molecular electronic sensor, wherein the polymerase processive enzyme is conjugated directly into the current path, and directly to the metal electrodes, without use of arm or bridge molecules;

FIG. 13-E shows embodiments of a processive enzyme molecular electronic sensor, wherein the processive enzyme comprises a helicase (human RECQ-like helicase) and is conjugated to a bridge molecule that spans the gap between the spaced-apart electrodes;

FIG. 14-A shows the physical structure of various embodiments of different DNA data encoding template molecules, wherein the signaling features are: (A) bound DNA oligonucleotides, (B) bound DNA oligonucleotides further comprising additional modifying groups, (C) single stranded DNA further comprising modifying groups, and (D) double stranded DNA further comprising modifying groups;

FIG. 14-B shows template structures (strand architectures) that allow a data payload from a single DNA molecule to be read multiple times by the same processive enzyme molecular sensor;

FIG. 16 shows examples of Binary Data Encoding Schemes ("BES") that can be used to encode digital information into the DNA data payload segment of a synthetic DNA molecule, for later reading by a processive enzyme molecular electronic sensor;

FIG. 17-A shows an embodiment of a fabrication stack usable to put a plurality of DNA reader sensors on a chip for massively parallel, low-cost deployment of a DNA reading system;

FIG. 17-B shows an embodiment of CMOS chip and pixel architecture for a chip-based array of processive enzyme molecular sensors. In this embodiment, the sensor is formatted into scalable CMOS chip sensor array architecture, with molecular electronic sensor and source, gate and drain terminals;

DETAILED DESCRIPTION

Figure 2:
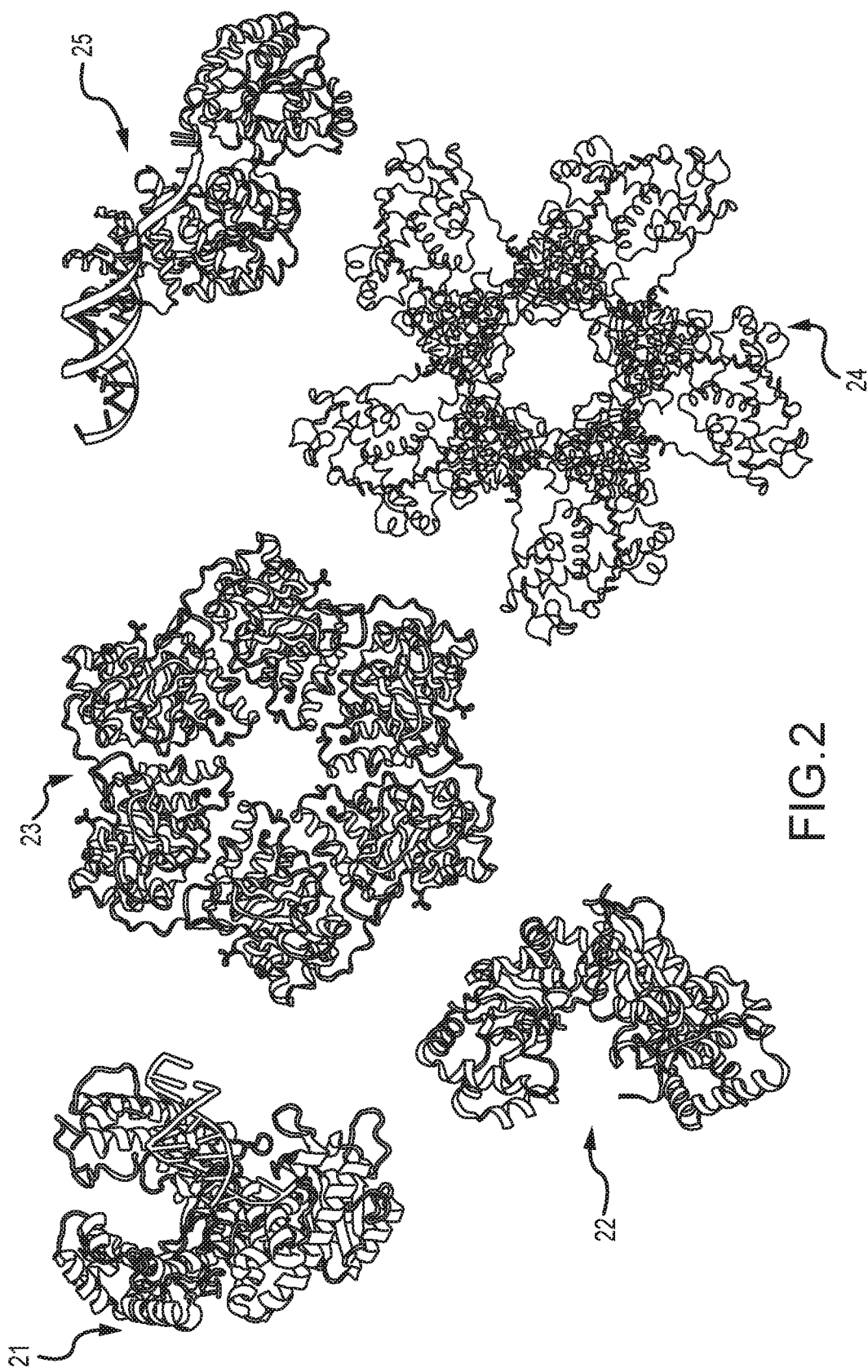
FIG. 2 shows representative processive enzymes that can be used in a molecular sensor to act on various forms of DNA, including specific examples of a polymerase, a helicase, an exonuclease, and a DNA packaging molecular motor. Illustrated are: Klenow+DNA, Protein DataBase (PDB) structure ID 1KLN; Exonuclease I E Coli, PDB ID 1FXX; PDB ID 1G8Y; the crystal structure of the hexameric replicative helicase REPA; PDB ID 3EZK, Bacteriophage T4 gp17 motor assembly based on crystal structures and cryo-EM reconstructions; PDB ID 2WWY; and the structure of human RECQ-like helicase in complex with a DNA substrate.

In various embodiments, a molecular electronics sensor comprising a processive enzyme is disclosed that extracts information from DNA molecules by reading digital data stored as DNA. The present disclosure further provides a means of deploying such sensors in a chip-based format, and a resulting data reading system that supports such a chip-based sensor device. Reading information encoded into DNA molecules by use of the processive enzyme molecular sensors of the present disclosure is fundamental to overall methods and systems for DNA data storage. Various aspects of these methods and systems for DNA data storage, including aspects of molecular sensors for reading DNA molecules encoded with digital information, is disclosed in PCT Application Serial No. PCT/US2018/013140, filed Jan. 10, 2018 and entitled "METHODS AND SYSTEMS FOR DNA DATA STORAGE," the disclosure of which is incorporated herein by reference in its entirety for all purposes.

Definitions

As used herein, the term "DNA" may refer not only to the biological DNA molecule, but also to fully synthetic versions, made by the methods of synthetic chemistry, such as nucleotide phosphoramidite chemistry, or by serial ligation of DNA oligomers, and also to forms made with chemical modifications present on the bases, sugar, or backbone, of which many are known to those skilled in nucleic acid biochemistry, including methylated bases, adenylated bases, other epigenetically marked bases, or also including non-standard or universal bases, such as inosine or 3-nitropyrrole, or other nucleotide analogues, or ribobases, or abasic sites, or damaged sites, and also including such DNA analogues as Peptide Nucleic Acids (PNA), Locked Nucleic Acids (LNA), Xeno Nucleic Acids (XNA) (a family of sugar-modified forms of DNA, including Hexitol Nucleic Acid (HNA)), Glycol Nucleic Acid (GNA), etc., and also including the biochemically similar RNA molecule along with synthetic RNA and modified forms of RNA. All these biochemically closely related forms are implied by the use of the term DNA, in the context of referring to the data storage molecule used in a DNA storage system, including a template single strand, a single strand with oligomers bound thereon, double stranded DNA, and double strands with bound groups such as groups to modify various bases. In addition, as used herein, the term "DNA" may refer to the single stranded forms of such molecules, as well as double helix or double-stranded forms, including hybrid duplex forms, including forms that containing mismatched or non-standard base pairings, or non-standard helical forms such as triplex forms, as well as molecules that are partially double stranded, such as a single-stranded DNA bound to an oligonucleotide primer, or a molecule with a hairpin secondary structure. In various embodiments, "DNA" refers to a molecule comprising a single-stranded DNA component having bound oligonucleotide segments and/or perturbing groups that can act as the substrate for a processive enzyme to process, and in doing so, generate distinguishable signals in a monitored electrical parameter of a molecular sensor comprising the processive enzyme.

DNA sequences as written herein, such as GATTACA (SEQ ID NO: 1), refer to DNA in the 5' to 3' orientation, unless specified otherwise. For example, GATTACA (SEQ ID NO: 1) as written herein represents the single stranded DNA molecule 5'-G-A-T-T-A-C-A-3' (SEQ ID NO: 1). In general, the convention used herein follows the standard convention for written DNA sequences used in the field of molecular biology.

As used herein, the term "dNTP" may refer not only to the standard, naturally occurring nucleoside triphosphates used in biosynthesis of DNA—i.e. dATP, dCTP, dGTP, and dTTP—but also to natural or synthetic analogues or modified forms of these, include those that carry base modifications, sugar modifications, or phosphate group modifications, such as an alpha-thiol modification or gamma phosphate modifications, or the tetra-, penta-, hexa- or longer phosphate chain forms, or possibly with additional groups conjugated to any of the phosphates, particularly the beta, gamma or higher order phosphates in the chain. In general, as used herein, "dNTP" may mean any nucleoside triphosphate analogue or modified form that can be incorporated by a polymerase enzyme as it extends a primer, or that would enter the active pocket of such an enzyme and engage transiently as a trial candidate for incorporation.

As used herein, the term "oligonucleotide" or "binding oligonucleotide" refers to a short segment of DNA, or analog forms described above, having a length in the range of 3-100 bases, or 5-40 bases, or 10-30 bases, which can hybridize with complementary sequence contain in a template strand. Such hybridization may be through perfect Watson-Crock base-paring matches, or may involve mismatches or nonstandard base pairings.

As used herein, the term hybridization refers to the process of complementary strand binding as it occurs in the DNA double helix, or in similar duplex formation for DNA analogs.

As used herein, "buffer," "buffer solution" and "reagent solution" refers to a solution which provides the environment in which the processive enzyme sensor can operate and produce signals from supplied DNA templates. In various embodiments, the solution is an aqueous solution, which may comprise dissolved, suspended or emulsified components such as salts, pH buffers, divalent cations, surfactants, blocking agents, solvents, template primer oligonucleotides, other proteins that complex with the polymerase, and also possibly including the polymerase substrates, i.e. dNTPs, analogues or modified forms of dNTPs, and DNA molecule substrates or templates.

As used herein, "binary data" or "digital data" refers to data encoded using the standard binary code, or a base 2 {0,1} alphabet, data encoded using a hexadecimal base 16 {0,1} alphabet, data encoded using the base 10 {0-9} alphabet, data encoded using ASCII characters, or data encoded using any other discrete alphabet of symbols or characters in a linear encoding fashion.

As used herein, "digital data encoded format" refers to the series of binary digits, or other symbolic digits or characters that come from the primary translation of the DNA sequence features used to encode information in DNA, or the equivalent logical string of such classified DNA features. In some embodiments, information to be archived as DNA may be translated into binary, or exist initially as binary data, and then this data may be further encoded with error correction and assembly information, into the format that is directly translated into the code provided by the distinguishable DNA signaling features. This latter association is the primary encoding format of the information. Application of the assembly and error correction procedures is a further, secondary level of decoding, back towards recovering the source information.

As used herein, the term "signaling feature" refers to a characteristic of a data-encoding DNA molecule that, when encountered and processed by the processive enzyme of a processive enzyme molecular sensor, produces a signal in a monitored electrical parameter of the sensor circuit, such as current (i). Arrangements of signaling features on a DNA molecule are used to encode information in a synthetic DNA molecule. The broader group of signaling features herein further comprise both "bound groups" capable of displacement by a processive enzyme of a sensor and "perturbing groups" that are not displaced from the DNA molecule by the processive enzyme. Both types of signaling features on a DNA molecule provide distinct signals in a monitored electrical parameter of the sensor circuit when encountered by the processive enzyme of the sensor. Signaling features comprise, for example, hybridization-bound oligonucleotides, chemical groups conjugated to the DNA, or combinations of such to achieve arrangements of features that produce distinguishable signals when processed by the sensor processive enzyme.

As used herein, a "data-encoding DNA molecule," or "DNA data encoding molecule," refers to a DNA molecule synthesized to encode data, such as binary information, in its molecular structure, including copies of information containing DNA molecules or other DNA molecules derived from such molecules, such as complementary sequences.

As used herein, "reading data from DNA" refers to any method of measuring distinguishable events, such as electrical signals or other perturbations in a monitored electrical parameter of a circuit, which correspond to molecular features in a synthetic DNA molecule that were used to encode information into the DNA molecule.

As used herein, "electrodes" refer to nano-scale electrical conductors (more simply, "nano-electrodes"), disposed in pairs and spaced apart by a nanoscale-sized electrode gap between the two electrodes in any pair of electrodes. In various embodiments, the term "electrode" may refer to a source, drain or gate. A gate electrode may be capacitively coupled to the gap region, and may be a "buried gate," "back gate," or "side gate." The electrodes in a pair of spaced-apart electrodes may be referred to specifically (and labeled as such in various drawing figures) as the "source" and "drain" electrodes, "positive" and "negative" electrodes, or "first" and "second" electrodes. Whenever electrodes in any of the drawing figures herein are labeled "positive electrode" and "negative electrode," it should be understood the polarity indicated may be reversed, (i.e., the labels of these two elements in the drawings can be reversed), unless indicated otherwise, (such as an embodiment where electrons may be flowing to the negative electrode). Nano-scale electrodes in a pair of electrodes are spaced apart by an electrode gap measuring about 1 nm to 100 nm, and may have other critical dimensions, such as their width, height, and length, also in this same nanoscale range. Such nano-electrodes may be composed of a variety of materials that provide conductivity and mechanical stability. They may be comprised of metals, or semiconductors, for example, or of a combination of such materials. Pairs of spaced-apart electrodes may be disposed on a substrate by nano-scale lithographic techniques.

As used herein, the term "enzyme" refers to any molecule or molecular complex that acts on a substrate molecule to alter its state. Such enzymes are often proteins or comprise a protein component.

As used herein, a "processive enzyme" refers to any enzyme having "processivity," which is the ability to catalyze consecutive reactions without the enzyme releasing its substrate. In various embodiments, a processive enzyme, as all or part of its enzymatic activity, may process a DNA molecule by engaging the DNA molecule at one end of the molecule or at an internal initiation site and translocating along the DNA molecule. This translocative movement is, of course, relative, and it may be the substrate that moves through a processive enzyme if the enzyme is physically anchored in a molecular sensor. Processive enzymes include, but are not limited to, polymerases, helicases, exonucleases, and molecular motors for packaging virus DNA.

As used herein, a "bridge molecule" refers to a molecule bound between two spaced-apart electrodes in a pair of electrodes, to span the electrode gap there between, and complete an electrical circuit. In various embodiments, a bridge molecule has roughly the same length as an electrode gap, such as 1 nm to 100 nm, or in some cases, about 10 nm. Bridge molecules for use herein may comprise double stranded DNA, other analog DNA duplex structures, such as DNA-RNA, DNA-PNA or DNA-LNA or DNA-XNA duplex hybrids, peptides, protein alpha-helix structures, antibodies or antibody Fab domains, graphene nanoribbons or carbon nanotubes, silicon nanowires, or any other of a wide array of molecular wires or conducting molecules known to those skilled in the art of molecular electronics. A bridge molecule herein may be described as having a "first" and "second" end, such as a base at or near the 3' end and a base at or near the 5' end of a DNA molecule acting as a bridge molecule. For example, each end may be chemically modified such that the first end of a bridge molecule bonds to a first electrode and the second end of a bridge molecule bonds to a second electrode in a pair of spaced-apart electrodes. This nomenclature aids in visualizing a bridge molecule spanning an electrode gap and bonding to each electrode in a pair of spaced-apart electrodes. In various embodiments, the first and second ends of a bridge molecule may be chemically modified so as to provide for self-assembly between the bridge molecule and a processive enzyme and/or between the bridge molecule and one or both electrodes in a pair of electrodes.

As used herein, an "arm" molecule has many of the same characteristics as a bridge molecule, and may comprise the same chemical species, e.g., DNA, although an arm molecule may be of shorter molecular length so that it may assist bonding a processive enzyme to only one electrode in a pair of spaced-apart electrodes. In various aspects, at least two arm molecules may be used to electrically connect a processive enzyme to both electrodes in a pair of spaced-apart electrodes, thereby suspending it between electrodes without directly bonding the enzyme to either electrode.

As used herein, the term "conjugation" refers to a chemical linkage, (i.e., bond), of any type known in the chemical arts, e.g., covalent, ionic, Van der Waals, etc. The conjugations of a processive enzyme to bridge and/or arm molecules, or conjugations between bridge or arm molecules to an electrode, may be accomplished by a diverse array of conjugation methods known to those skilled in the art of conjugation chemistry, such as biotin-avidin couplings, thiol-gold couplings, cysteine-maleimide couplings, gold binding peptides or material binding peptides, click chemistry coupling, Spy-SpyCatcher protein interaction coupling, or antibody-antigen binding (such as the FLAG peptide tag/anti-FLAG antibody system), and the like. Conjugation of a processive enzyme to each electrode in a pair of spaced-apart electrodes comprises an "electrical connection" or the "electrical wiring" of the enzyme into a circuit that includes the enzyme and the pair of electrodes. In other words, the enzyme is conjugated to each electrode in a pair of electrodes to provide a conductive pathway between the electrodes that would be otherwise be insulated from one another by the electrode gap separating them. A conductive pathway is provided by electron delocalization/movement through the chemical bonds of the enzyme, such as through C—C bonds.

Further definitions, and other aspects of molecular electronic sensors, are disclosed in PCT Application Serial No. PCT/US2018/029382, filed on Apr. 25, 2018, and U.S. Pat. No. 10,036,064, issued Jul. 31, 2018, the disclosures of which are incorporated herein by reference in their entireties for all purposes.

FIG. 1-A shows an embodiment of a molecular electronic sensing circuit in which a molecule completes an electrical circuit and an electrical circuit parameter is measured versus time to provide a signal, wherein variations in signal reflect interactions of the molecule with other molecules in the environment. As illustrated in FIG. 1-A, a molecular electronics sensor 1 comprises a circuit in which a single sensor molecule 2, (or alternatively, a sensor complex comprising a small number of molecules), forms a completed electrical circuit by spanning the electrode gap 9 between a pair of spaced-apart nano-scale electrodes 3 and 4, comprising for example positive and negative electrodes, respectively, disposed on a support layer 5. The sensor molecule may be electrically conjugated in place to each of the electrodes by specific attachment points 6 and 7. In certain aspects, an electronic parameter 100 of the circuit is measured as the sensor molecule 2 interacts with various interacting molecules 8 to provide signals 101 in the measured electronic parameter. The measured parameter 100 may comprise current (i) passing between the electrodes and through the sensor molecule 2 versus time, with the electrical signals 101 in the measured parameter indicative of molecular interactions between the interacting molecules 8 and the sensor molecule 2, as illustrated by the plot of (i) versus (t) in FIG. 1-A.

With reference now to FIG. 1-B, a processive enzyme molecular electronics sensor 10 provides a reader for reading digital data encoded into a DNA molecule 18. In this example, a molecular complex 12 comprises a molecular bridge 13 and a processive enzyme 14 bonded thereto for reading the digital data. The single enzyme molecule 14 processively engages with a target DNA molecule 18, translocating along the DNA as it acts on it, and by doing so produces electrical signals 102 in the measured electronic parameter of the circuit as it processes along the DNA template, as shown in the plot of (i) versus (t) at the left of the figure. In various examples, the DNA template molecule 18 is augmented with "signaling features" 17, each of which results in a distinguishable electrical signal 102 in the (i) versus (t) plot when the processive enzyme 14 encounters the signaling feature. In this way, the processive enzyme sensor 10 produces a series of distinguishable electrical signals (e.g., 103 and 104 shown in the inset plot of (i) versus (t)), corresponding to the specific distinct signaling features 17 provided in predetermine patterns on the template DNA molecule 18. The inset in FIG. 1-B shows the alignment between the signaling features on the DNA molecule (indicated as "Feat. 1" and "Feat. 2" in the inset) and the distinguishable electrical signals visible in the monitored electrical parameter (indicated as 103 and 104 in the plot of (i) versus (t)). Arrangements of distinguishable signal features 17 can therefore encode information in a synthetic DNA molecule, and may be incorporated into DNA through a variety of encoding schemes, (e.g., discussed below in reference to FIG. 16).

The processive enzyme is a critical element within a processive enzyme molecular sensor that is capable of reading DNA molecules. There are many processive enzymes capable of processively engaging with DNA, such as to perform various biological functions in various organisms. The important feature here is that the enzyme translocates along the DNA molecule in the course of its function. Such enzymes typically have a specific recognition structure that may occur at one end of a DNA strand, and they engage at that site, and initiate a process in which they translocate along the DNA molecule in one direction, perhaps performing some further function as they move along the molecule. Such translocation can in some cases be entirely unidirectional or can in other cases be predominantly in one direction, but with the possibility of reverse motions. Such translocation may process the entire DNA molecule from one end to the other, or may halt or disengage before reaching the other end.

FIG. 2 illustrates non-limiting representatives of some major categories of processive enzymes that act on DNA templates. Shown from left to right are examples of a polymerase 21, an exonuclease 22, a helicase 23, a molecular motor 24 for packaging DNA, and another helicase 25. Each of these types of processive enzymes find use in a processive enzyme molecular sensor herein, and each perform a different major function in regards to processing DNA.

The polymerase 21 illustrated in FIG. 2 is the E. Coli Klenow fragment polymerase (shown is structure 1KLN of the Protein Database (PDB)). In general, a polymerase synthesizes a complementary strand as it translates along single-stranded template DNA. Of use in the molecular sensors of the present disclosure are polymerases having strand-displacing activity, meaning that, as they translocate along single-stranded DNA they displace the complementary strand to expose the template for the strand being synthesized if they encounter a double stranded segment.

The exonuclease 22 illustrated in FIG. 2 is the E. Coli exonuclease I (PDB structure 1FXX). In general, an exonuclease digests a DNA strand as it translocates along it, one base at a time, starting from one end. Various forms act on single or double stranded DNA, and may digest one or both strands. Exonucleases may have a chemical polarity in the direction they digest the strand (i.e., 3' to 5' or 5' to 3'), and may require different types of initiation. Exonucleases may behave in different ways when they encounter various alterations in the strands they are processing, such as a change between single and double stranded forms, or the presence of chemically modified bases, or adducts, or attached groups.

One of the helicases, helicase 23, illustrated in FIG. 2 is the bacterial Helicase REPA, (PDB ID 1G8Y), which is a hexameric protein complex. The helicase 25 illustrated in FIG. 2 is the human RECQ-like DNA helicase. In general, a helicase unzips the complementary strands as it translocates along double stranded DNA. Various types of helicases may also purely translocate along single-stranded DNA, performing no other activity.

The packaging motor protein 24 illustrated in FIG. 2 is the motor protein gp17 from the T4 bacteriophage (PDB ID 3EZK). In general, a DNA packaging motor translocates a DNA strand into the capsule of a viral particle as part of the process of viral replication. Such motors may translocate along a single or double stranded DNA molecule.

FIG. 2 illustrates only non-limiting examples of enzymes that processively engage with DNA. There are many other specific proteins from these categories, as well as other forms of processive enzymes well known to those in the field of molecular biology that find use in the processive enzyme molecular sensors of the present disclosure. Further, the enzymes illustrated in FIG. 2 comprise the native forms of these enzymes. It is understood that for the processive enzyme molecular sensors of the present disclosure, native enzymes may be used, or enzymes that have been genetically modified to provide conjugation groups at specific sites, such as to modify or augment their activity, rate of translocation, or tolerance for modifications on a DNA molecule.

FIG. 3-A illustrates various embodiments of a processive enzyme molecular electronics sensor 30 capable of reading digital information encoded and stored in DNA. The processive enzyme molecular sensor 30 comprises a molecular sensor complex 32 spanning electrode gap 39 and further comprising a bridge molecule 33 and a processive enzyme 34 bound thereto. In these embodiments, the DNA template molecule 38 comprises bound groups 37, capable of displacement from the DNA as the processive enzyme 34 translocates along the DNA molecule 38. In these examples, a displacement event, comprising displacement of a bound group 37 from the DNA molecule 38 to an unbound group 37', generates a corresponding signal feature in a monitored electrical parameter such as current (i) through the sensor circuit versus time (t). As illustrated in FIG. 3-A, the displacement events may appear as peaks 301, 302, 303 and so forth, or other distinguishable electrical signals, corresponding to each of the displacement events, in the (i) versus (t) plot. As detailed herein, there are different types of such bound groups for use herein that produce distinguishable signal features when displaced by the processive enzyme of the sensor. Arrangements of such bound groups 37 comprise encoded digital information, encoded in DNA molecules such as, for example, by the encoding schemes of FIG. 16. In various embodiments, bound groups 37 may comprise DNA oligonucleotides hybridized to single stranded DNA, or oligonucleotides further comprising a signal enhancing modification such as an attached charged group or structural group. Such constructs are illustrated in the upper two structures of FIG. 14, discussed herein.

FIG. 3-B illustrates another series of embodiments of a processive enzyme molecular electronics sensor 31 for reading digital information stored in DNA. The molecular sensors 31 comprise a molecular sensor complex 312 spanning the electrode gap 319 and further comprising a bridge molecule 313 and a processive enzyme 314 bonded thereto. In these embodiments, a DNA template molecule 318 further comprises perturbing groups 317 integrated into the molecule, wherein such groups 317 remain on the DNA template molecule as the DNA molecule translocates through the processive enzyme 314, and where in so doing the local perturbations present in the molecule result in distinguishable perturbation signals 304, 305, and 306 in the monitored electrical parameter, such as (i) versus (t). In this way, arrangements of perturbing groups integrated in DNA molecules can be used to store information in DNA molecules, such as for example by the encoding schemes of FIG. 16. In various embodiments, such perturbing groups 317 may comprise modifications to the bases of the DNA, including modification to the nucleobase, the sugar residue, or the phosphate backbone. A very large number of such base modifications are well known to those in the field of molecular biology. Modifications may further comprise groups conjugated to modified bases, such as by any standard means of conjugation, including click chemistry coupling, biotin-based coupling, N-hydroxysuccinimide (NHS) conjugation, maleimide conjugation, or any of many other methods known for conjugating groups to DNA.

The processive enzyme molecular sensor embodiments illustrated in FIGS. 3-A and 3-B comprise a molecular complex. In these drawings, the molecular complex is illustrated generically as comprising a bridge molecule (oval shape) and a processive enzyme (globular shape) bonded thereto. The molecular complex is electrically connected between a pair of spaced-apart electrodes to span the electrode gap and complete an electronic circuit. The processive enzyme may be integrated as part of the molecular complex in various ways. FIGS. 4-A, 4-B, and 4-C illustrate various non-limiting embodiments for this complex and how the enzyme is integrated into an electronic circuit that comprises the molecular complex.

FIG. 4-A shows an embodiment of a processive enzyme molecular sensor 40 in which the processive enzyme 44 is conjugated, via a one or more conjugations points 46, to a bridge molecule 43 that spans the electrode gap 49. The bridge molecule 43 comprises first and second ends capable of attachment to each of the electrodes at attachment points 47 and 48. In this way, the bridge molecule is electrically connected to each electrode in a pair of spaced-apart electrodes, such as the positive and negative electrodes shown, to span the electrode gap 49 between electrodes and complete the sensor circuit.

FIG. 4-B shows an embodiment of a processive enzyme molecular sensor 410 in which the processive enzyme 412 is conjugated directly into the current path between the electrodes, spanning the electrode gap 419, by conjugation to two separate "arm" molecules 413 and 414, which in turn are conjugated at one of their ends to each of the two electrodes via attachment points 416 and 417, and to bonding sites on the enzyme 412 at conjugation points 415 and 418, as shown.

FIG. 4-C shows an embodiment of a processive enzyme molecular sensor 420 in which the processive enzyme 422 is conjugated directly to the electrodes to span the electrode gap 430 via the conjugation points 428 and 425, without any intervening arm or bridge molecules to assist in conjugating the enzyme to the electrodes. In this way, the processive enzyme 422 is directly wired into and functions as an element of the sensor circuit.

In general, for various embodiments of processive enzyme molecular electronic sensors, such as illustrated in FIG. 1-B through FIG. 4-C, there are many specific options for the components within the sensors. In various embodiments, the enzyme may be a native or mutant form of a polymerase, a reverse transcriptase, a helicase, an exonuclease, or a molecular motor for packaging DNA into a virus. In other embodiments, the mutated enzyme forms enable site specific conjugation of the enzyme to a bridge molecule, to one or more arm molecules, or to each of the electrodes in a pair of spaced-apart electrodes, through introduction of specific conjugation sites in the enzyme. Such conjugation sites engineered into the protein by recombinant methods or methods of synthetic biology, may in various embodiments comprise any one of a cysteine, an aldehyde tag site (e.g. the peptide motif CxPxR), a tetracysteine motif (e.g. the peptide motif CCPGCC (SEQ ID NO: 2)), and an unnatural or non-standard amino acid (NSAA) site, such as through the use of an expanded genetic code to introduce a p-acetylphenylalanine, or an unnatural crosslinkable amino acid, such as through the use of RNA- or DNA-protein cross-link using 5-bromouridine, (see Gott, J. M., et al., *Biochemistry*, 30 (25), 6290-6295 (1991)).

In various aspects, the bridge molecules or arm molecules may comprise double stranded DNA, other analog DNA duplex structures, such as DNA-RNA, DNA-PNA or DNA-LNA or DNA-XNA duplex hybrids, peptides, protein alpha-helix structures, antibodies or antibody Fab domains, graphene nanoribbons or carbon nanotubes, silicon nanowires, or any other of a wide array of molecular wires or conducting molecules known to those skilled in the art of molecular electronics. The conjugations of a processive enzyme to such molecules, or of such molecules to the electrodes, may be accomplished by a diverse array of conjugation methods known to those skilled in the art of conjugation chemistry, such as biotin-avidin couplings, thiol-gold couplings, cysteine-maleimide couplings, gold binding peptides or material binding peptides, click chemistry coupling, Spy-Spy-Catcher protein interaction coupling, or antibody-antigen binding (such as the FLAG peptide tag/anti-FLAG antibody system) etc. Coupling of molecules to electrodes may be done via material binding peptides, or through the use of a SAM (Self-Assembling-Monolayer) or other surface derivatization on the electrode surface to present suitable functional groups for conjugation, such as azide or amine groups. The electrodes herein comprise electrically conducting nanoscale-dimensioned structures, which may comprise a metal, such as gold, silver, platinum, palladium, aluminum, chromium, or titanium, layers of such metals, such as gold on chromium, or semiconductors, such as doped silicon, or doped germanium. In various embodiments, a contact point of a first material may be disposed on a supporting second material, such that the contact point is a site that directs chemical self-assembly of the molecular complex to the electrode. In non-limiting examples, a sensor may comprise spaced-apart pairs of titanium or platinum electrodes having a gold dot contact point deposited on each one of the electrodes to direct self-assembly of bridge molecules to the contact points such that only one bridge molecule spans each electrode gap between a pair of spaced-apart electrodes.

Figure 5:
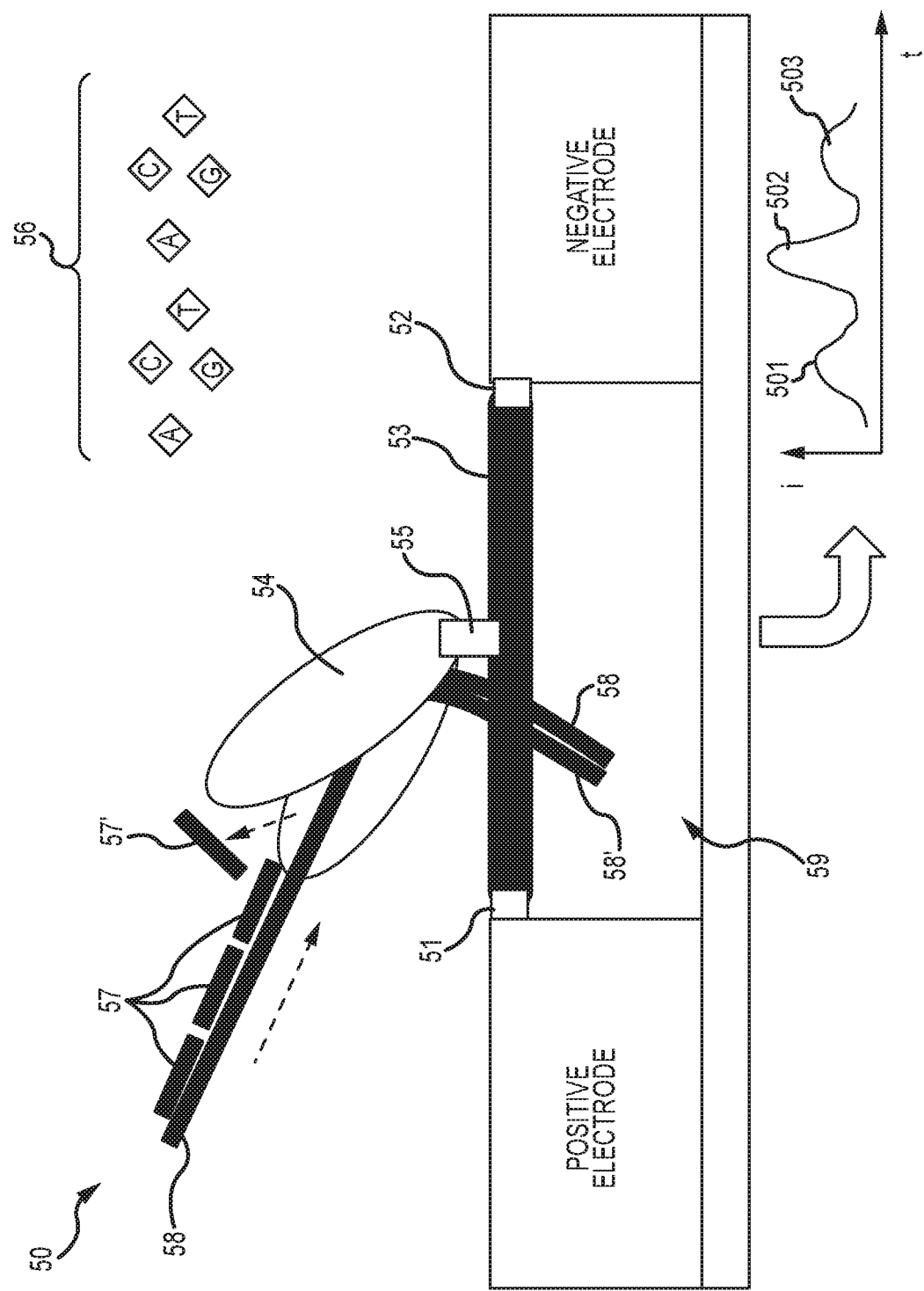
FIG. 5 illustrates embodiments of a processive enzyme molecular sensor, wherein the processive enzyme comprises a polymerase having strand displacing activity.

FIG. 5 shows embodiments of a processive enzyme molecular sensor 50 wherein the processive enzyme comprises a polymerase 54 having strand displacing activity. As shown, sensor 50 comprises processive enzyme 54 conjugated at one or more attachment points 55 to a bridge molecule 53 bonded between electrode pairs and spanning the electrode gap 59. The bridge molecule 53 comprises first and second ends functionalized to bond to the electrode pair at conjugation points 51 and 52. In this case, the processive translocation occurs as the polymerase 54 extends the 3' end of the primed strand 58, and synthesizes the complementary strand 58' of the underlying template strata. This takes place in a suitable buffer that also supplies dNTPs 56 for the synthesis of the complementary strand, as indicated. In the embodiment shown in FIG. 5, the signaling features 57 are DNA oligonucleotides hybridized to the template strand 58. The strand displacing polymerase 54 will displace and remove these oligonucleotides (as exemplified by the displacement of oligonucleotide 57') as it translocates in the course of synthesis. Each strand displacement event may generate a signal in the measured current of the circuit, as indicated by perturbations 501, 502 and 503 in the (i) versus (t) plot. The hybridizing oligonucleotides 57 may be DNA or DNA analogs, and may have further groups attached to enhance signaling, such as described further below in the context of FIG. 14.

Figure 6:
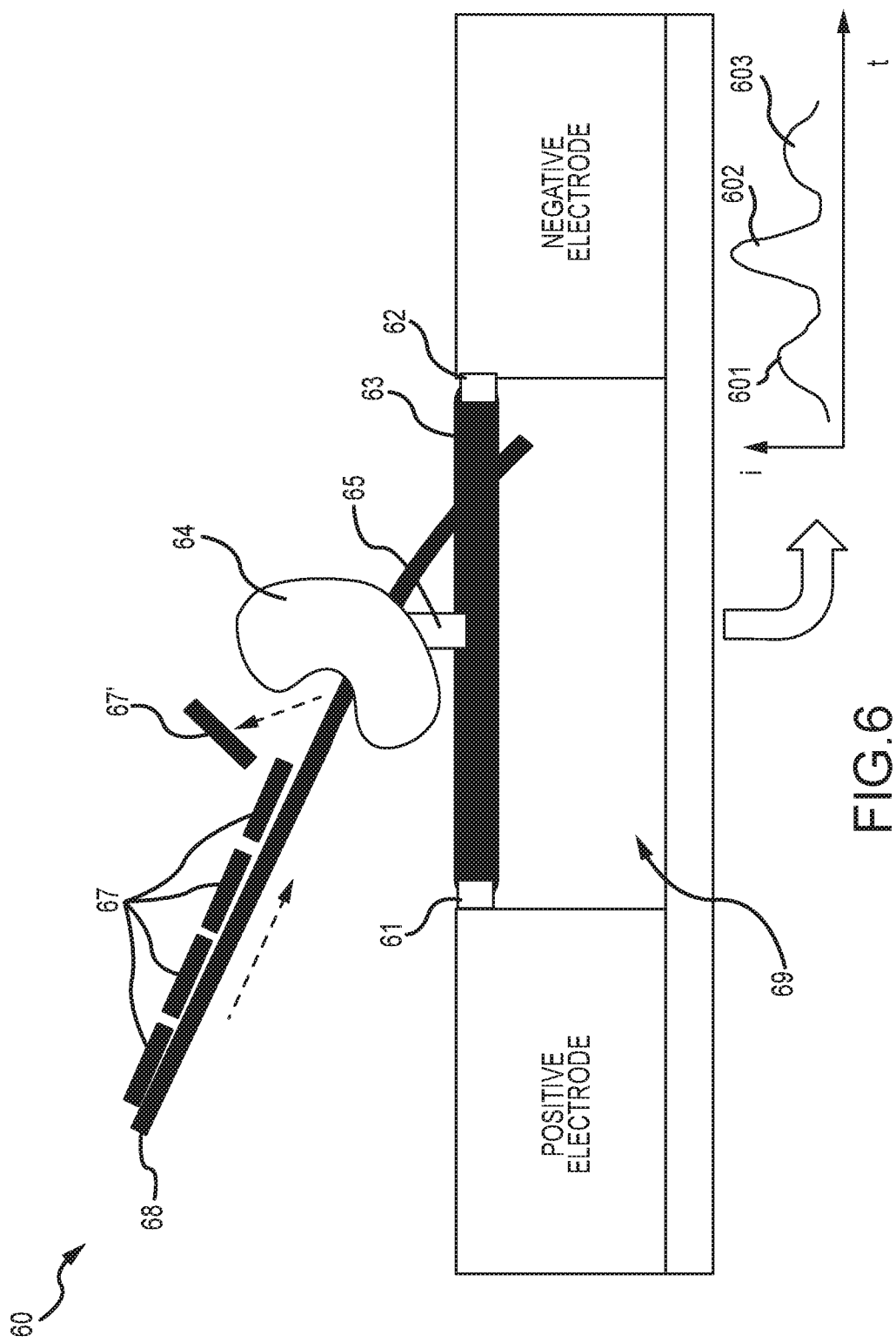
FIG. 6 illustrates embodiments of a processive enzyme molecular sensor, wherein the processive enzyme comprises a helicase having strand displacing activity.

FIG. 6 shows further embodiments of a processive enzyme molecular sensor 60 wherein the processive enzyme 64 comprises a helicase also having strand displacing activity. As shown, sensor 60 comprises processive enzyme 64 conjugated at one or more attachment points 65 to a bridge molecule 63 bonded between electrode pairs and spanning the electrode gap 69. The bridge molecule 63 comprises first and second ends functionalized to bond to the electrode pair at conjugation points 61 and 62. In this case, the signaling features 67 are DNA oligonucleotides hybridized to the template strand 68. The strand displacing helicase 64 will displace and remove these oligonucleotides (such as illustrated by displacement of oligonucleotide 67') as it translocates. Each strand displacement event may generate a signal in the measured current of the circuit, as indicated by the perturbations 601, 602, and 603 in the (i) versus (t) plot. The hybridizing oligonucleotides 67 in question comprise DNA or DNA analogs, and may have further groups attached to enhance signaling, such as described further below in the context of FIG. 14.

Figure 7:
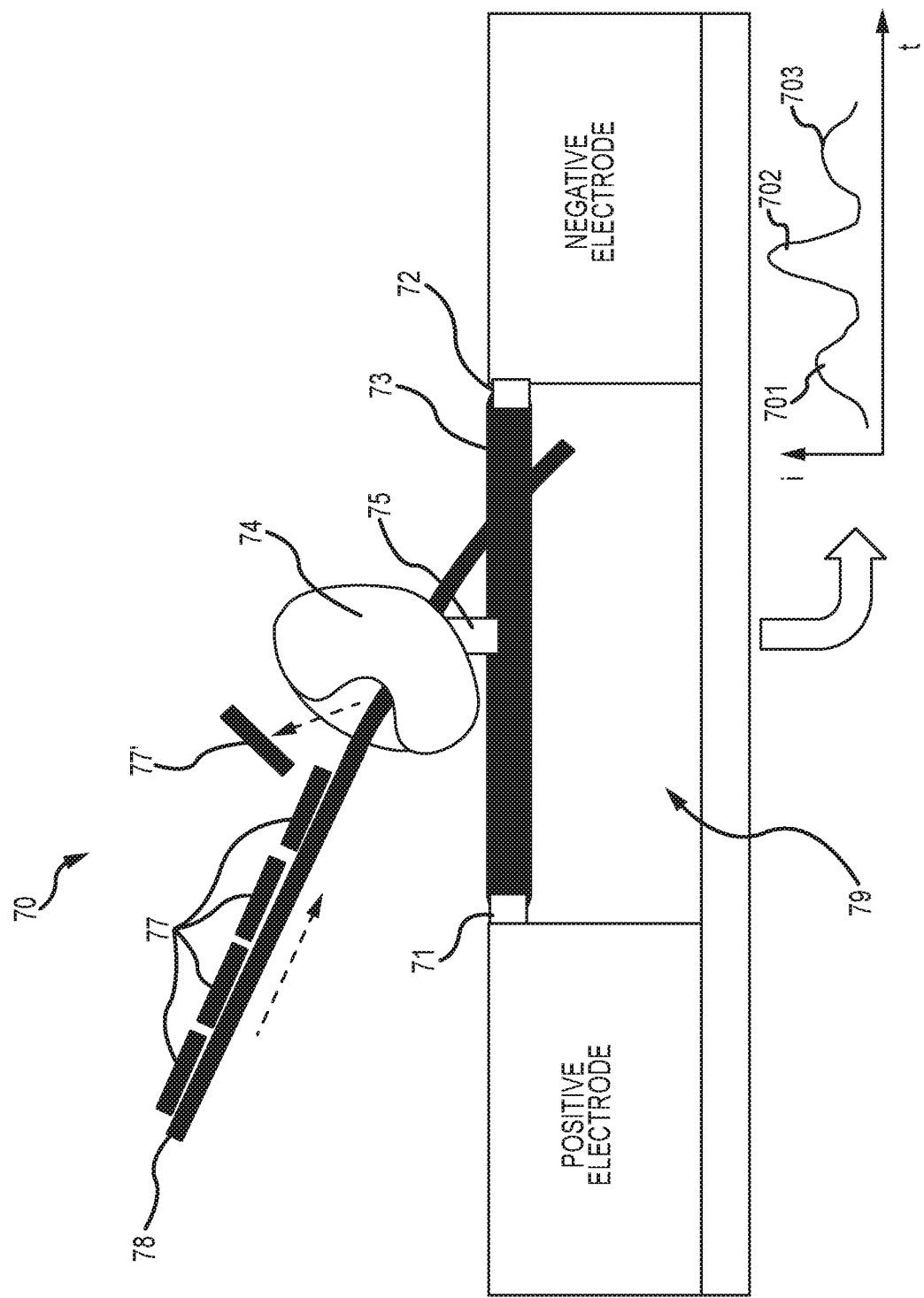
FIG. 7 illustrates embodiments of a processive enzyme molecular sensor, wherein the processive enzyme comprises a DNA packaging molecular motor having the ability to displace bound oligonucleotides sufficiently sterically bulky so as not to fit through the motor inlet.

FIG. 7 shows further embodiments of a processive enzyme molecular sensor 70 wherein the processive enzyme 74 comprises a DNA packaging molecular motor also having the ability to displace a bound oligonucleotide 77' that is sufficiently sterically bulky to not fit through the motor inlet. As shown, sensor 70 comprises processive enzyme 74 conjugated at one or more attachment points 75 to a bridge molecule 73 bonded between electrode pairs and spanning the electrode gap 79. The bridge molecule 73 comprises first and second ends functionalized to bond to the electrode pair at conjugation points 71 and 72. In this case, the signaling features comprise DNA oligonucleotides 77 hybridized to the template strand 78. The strand displacing motor 74 will displace and remove these oligonucleotides (such as 74' thus displaced) as it translocates the DNA. Each strand displacement event may generate a signal in the measured current of the circuit, as indicated by perturbations 701, 702, and 703 in the (i) versus (t) plot. The hybridizing oligonucleotides 77 in question may comprise DNA or DNA analogs, and may have further groups attached to enhance signaling, such as described further below in the context of FIG. 14. In these embodiments where the processive enzyme comprises a molecular motor, the oligonucleotides 77 may include a sterically hindering group that makes them too large to fit through the motor inlet, such as a polyethylene glycol (PEG) group, an Avidin protein group, or any other bulky group that can be readily attached to a DNA oligonucleotide. Many such groups are known and readily available to those skilled in molecular biology.

Figure 8:
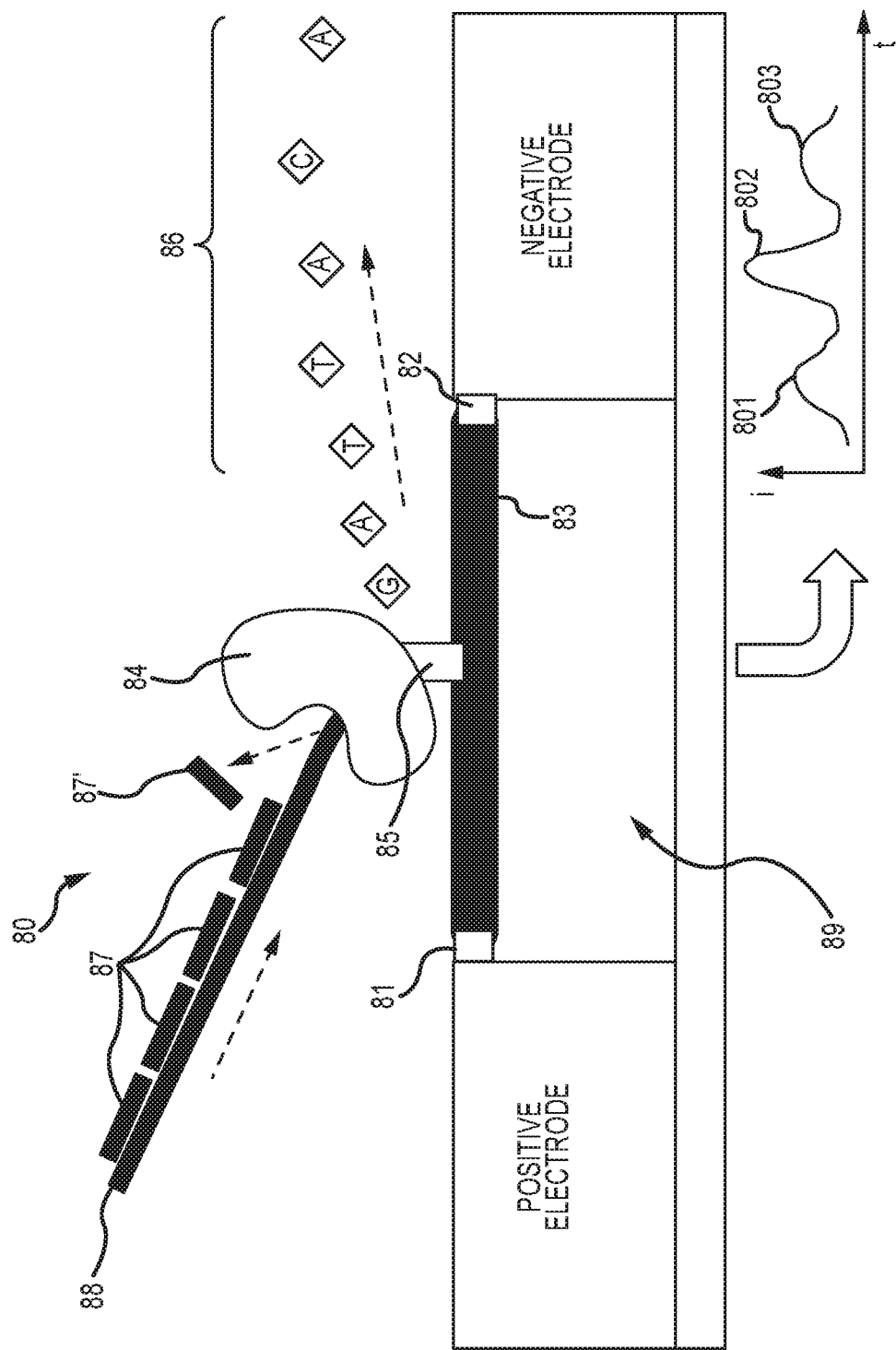
FIG. 8 illustrates embodiments of a processive enzyme molecular sensor, wherein the processive enzyme comprises an exonuclease having strand displacing activity.

FIG. 8 shows embodiments of a processive enzyme molecular sensor wherein the processive enzyme 84 comprises an exonuclease also having strand displacing activity. As shown, sensor 80 comprises processive enzyme 84 conjugated at one or more attachment points 85 to a bridge molecule 83 bonded between electrode pairs and spanning the electrode gap 89. The bridge molecule 83 comprises first and second ends functionalized to bond to the electrode pair at conjugation points 81 and 82. In this case, the signaling features comprise DNA oligonucleotides 87 hybridized to the template strand 88. The strand displacing exonuclease 84 will displace and remove these oligonucleotides (such as illustrated by the displacement of 87') as it translocates and digests the primary strand 88. Each strand displacement event may generate a signal in the measured current of the circuit, as indicated by the perturbations 801, 802, and 803 in the (i) versus (t) plot. The hybridizing oligonucleotides 87 may comprise DNA or DNA analogs, and may further comprise groups attached to enhance signaling, such as described further below in the context of FIG. 14. In various embodiments, some exonucleases may displace oligonucleotides 87 from the primary strand 88 by digesting entirely through the double stranded region of the paired segment, or by digesting only partially through it, at which point the remainder of the oligonucleotide dissociates from the primary strand.

Figure 9:
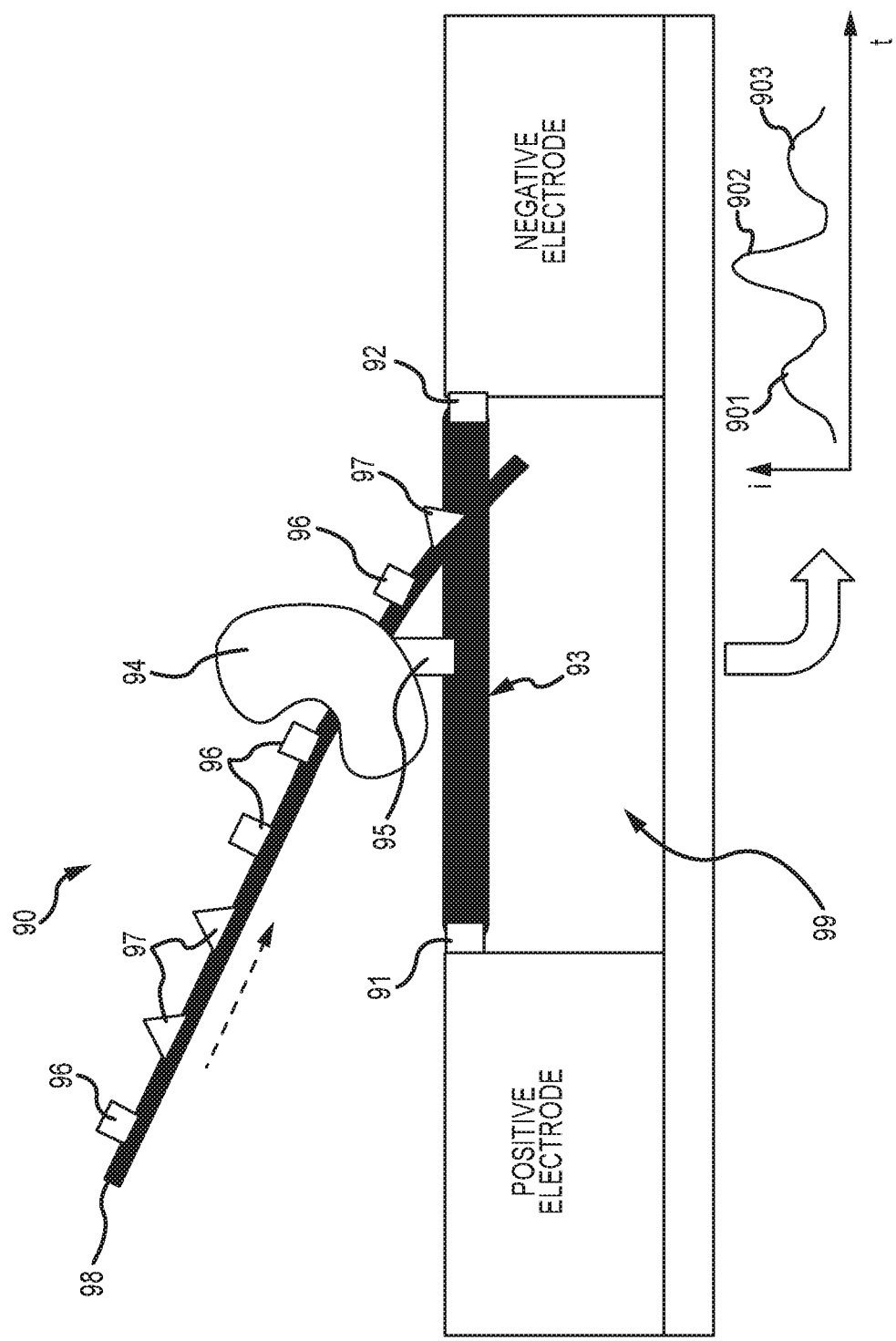
FIG. 9 illustrates embodiments of a processive enzyme molecular sensor, wherein the processive enzyme comprises a helicase.

FIG. 9 shows embodiments of a processive enzyme molecular sensor 90 wherein the processive enzyme 94 comprises a helicase. As shown, sensor 90 comprises processive enzyme 94 conjugated at one or more attachment points 95 to a bridge molecule 93 bonded between electrode pairs and spanning the electrode gap 99. The bridge molecule 93 comprises first and second ends functionalized to bond to the electrode pair at conjugation points 91 and 92. In this case, the signaling features 96, 97 are perturbing groups on the DNA strand 98. As each perturbing group 96, 97 passes by the helicase, it generates a signal in the measured current of the circuit, as indicated by 901, 902 and 903 in the (i) versus (t) plot. As illustrated, the various perturbing groups 96, 97 may be arranged in patterns that encode information. The illustration of this particular sequence of 96, 97, 97, 96, 96, and so forth is not intended to be limiting, and any number of different perturbing groups arranged in any pattern may be used in order to encode information. The DNA molecule may be single stranded, with the perturbing groups 96, 97 on the single strand, and the helicase 94 may be purely translating along the single strand. In other embodiments, the DNA may be double stranded, and the perturbing groups may be positioned on either strand, the one that goes "through" the helicase, to which it is bound, or the one that is displaced "around" the helicase. In other embodiments, such perturbing groups may be positioned on both strands within the same double stranded DNA molecule. Such groups are described further below in the context of FIG. 14.

Figure 10:
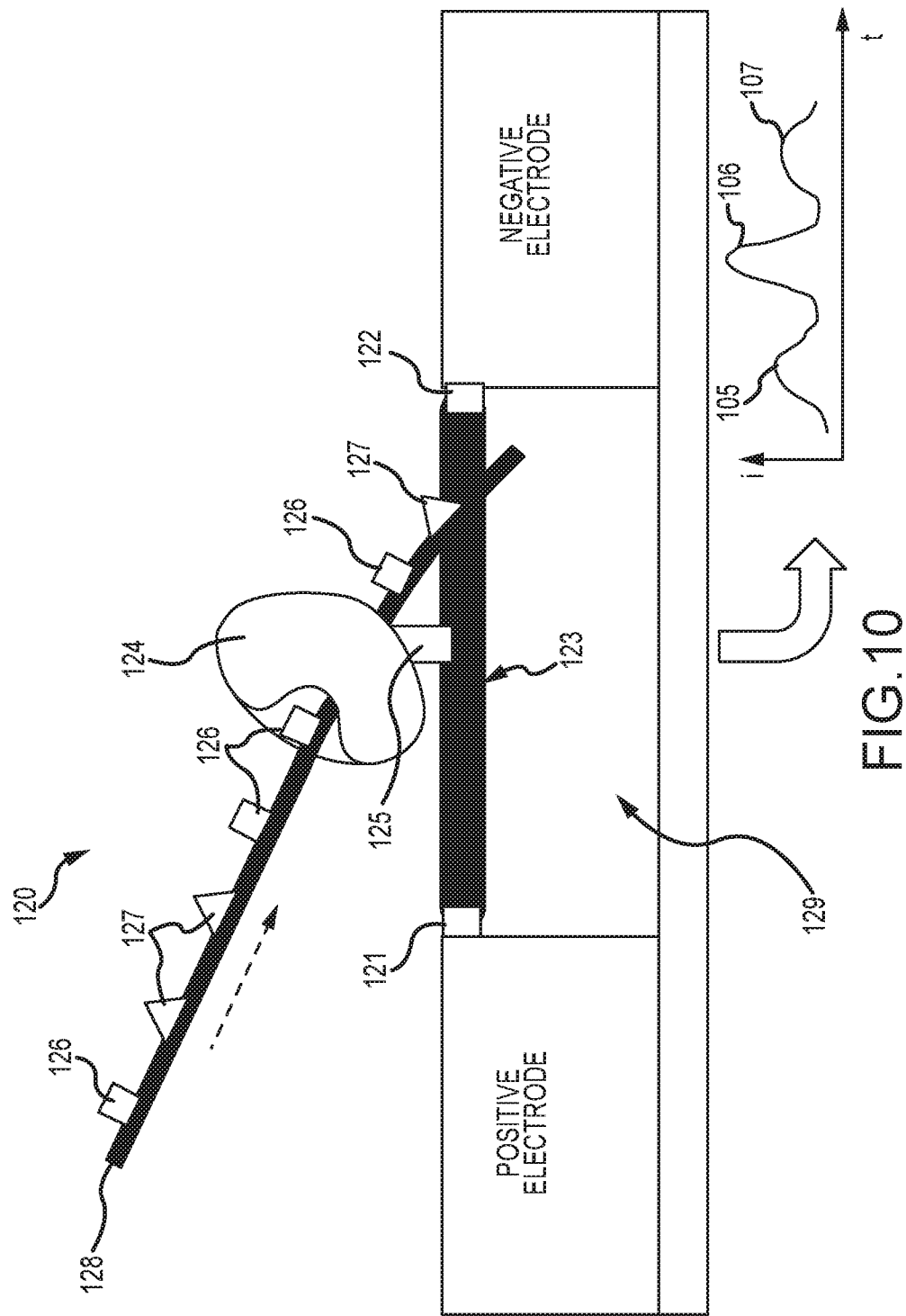
FIG. 10 illustrates embodiments of a processive enzyme molecular sensor, wherein the processive enzyme comprises a DNA packaging molecular motor.

FIG. 10 shows embodiments of a processive enzyme molecular sensor 120 wherein the processive enzyme 124 comprises a DNA packaging motor. As shown, sensor 120 comprises processive enzyme 124 conjugated at one or more attachment points 125 to a bridge molecule 123 bonded between electrode pairs and spanning the electrode gap 129. The bridge molecule 123 comprises first and second ends functionalized to bond to the electrode pair at conjugation points 121 and 122. In this case, the signaling features 126, 127 are perturbing groups on the DNA strand 128. As each perturbing group 126, 127 passes by the motor 124, it generates a corresponding signal in a monitored electrical parameter of the circuit, such as indicated by the changes 105, 106, and 107 seen in the (i) versus (t) plot. As illustrated, the various perturbing groups 126, 127 may be arranged in patterns that encode information. The illustration of this particular sequence of 126, 127, 127, 126, 126, and so forth is not intended to be limiting, and any number of different perturbing groups arranged in any pattern may be used in order to encode information. The DNA molecule may be single stranded, with the perturbing groups on the single strand, such as for a motor that translates a single strand. In other embodiments, the DNA may be double stranded, and the perturbing groups may be positioned on either strand, in the case of a motor that translocates double stranded DNA. Such groups are described further in the context of FIG. 14.

Figure 11:
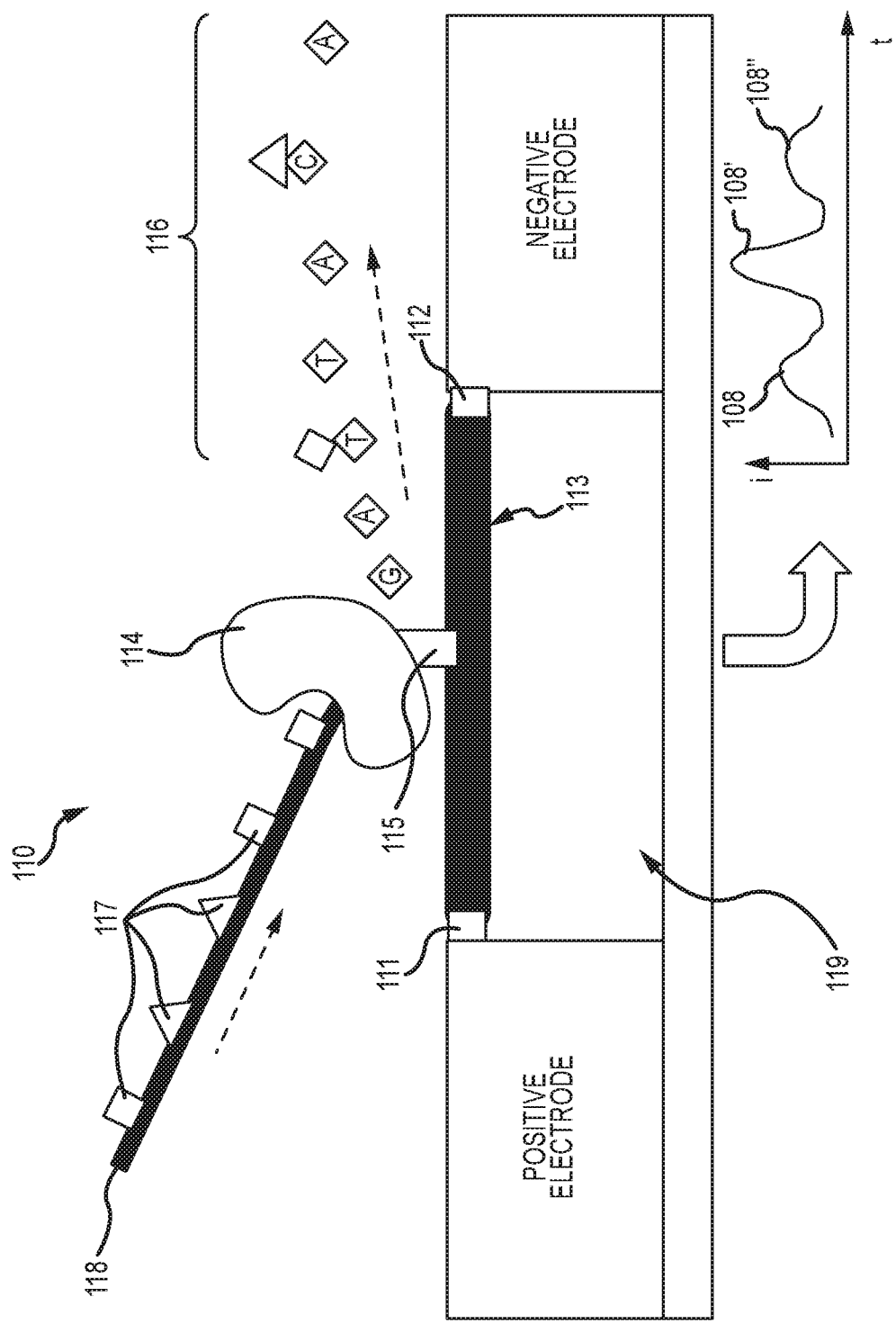
FIG. 11 illustrates embodiments of a processive enzyme molecular sensor, wherein the processive enzyme comprises an exonuclease.

FIG. 11 shows embodiments of processive enzyme molecular sensors 110 wherein the processive enzyme 114 comprises an exonuclease. As shown, sensor 110 comprises processive enzyme 114 conjugated at one or more attachment points 115 to a bridge molecule 113 bonded between electrode pairs and spanning the electrode gap 119. The bridge molecule 113 comprises first and second ends functionalized to bond to the electrode pair at conjugation points 111 and 112. In this case, the signaling features 117 are perturbing groups on the DNA strand 118. As each perturbing group 117 passes near the exonuclease, it generates a signal in a monitored electrical parameter of the circuit, such as indicated by the perturbations 108, 108', and 108" in the (i) versus (t) plot. The action of the exonuclease 114 on the functionalized DNA 118 produces digestion products 116 as the DNA is digested by the enzyme. The digestion products comprise a mixture of bases and functionalized bases that retain a perturbation group, as shown. The illustration of this particular sequence of perturbing groups 117 is not intended to be limiting, and any number of different perturbing groups arranged in any pattern may be used in order to encode information. The DNA molecule 118 may be single stranded, with the perturbing groups 117 positioned on the single strand, for an exonuclease that digests a single strand, or the DNA may be double stranded, for an exonuclease that processes double stranded DNA, and the perturbing groups may be on either strand, and in the case where only one strand of a double stranded DNA is digested, the perturbing groups 117 may reside on the digested or on the non-digested strand, or both. Such groups are described further below in the context of FIG. 14.

FIG. 12-A shows the detailed protein anatomy and DNA engagement of one of the exemplary processive enzymes for use herein, in this case a polymerase, and specifically the *E. Coli* Klenow fragment. The structure shown is PDB ID 1KLN. The detailed structure and how it engages the template DNA inform the choice of how to best conjugate the enzyme into the circuit, so as not to interfere with its interaction with DNA, and to position the signaling portions of the protein or DNA near to the molecular bridge for enhanced signal generation via proximity. The structure A at left is the polymerase engaged with a DNA substrate molecule whereas the structure B at right is the polymerase in its conformation absent engagement with a DNA substrate. The helix, sheet and loop portions of the enzyme are pointed out in both the engaged conformation and the conformation absent DNA engagement.

FIG. 12-B shows the detailed protein anatomy and DNA engagement of one of the exemplary processive enzymes for use herein, in this case a helicase, and specifically the human RECQ-like helicase. The structure shown is PDB ID 2WWY. The detailed structure and how it engages the template DNA inform the choice of how to best conjugate the enzyme into the circuit, so as not to interfere with its interaction with DNA, and to position the signaling portions of the protein or DNA near to the molecular bridge for enhanced signal generation via proximity. The structure shows the helicase engaged with a DNA substrate molecule. The helix, sheet and loop portions of the helicase are pointed out in the illustrated structure.

FIG. 13-A shows embodiments of a processive enzyme molecular sensor 130A wherein the polymerase enzyme 134A is conjugated to a molecular bridge molecule 133A, at a conjugation point 135A comprising a specific site on the enzyme 134A bonded to a specific site on the bridge molecule 133A. As shown, the bridge molecule 133A is bonded to each of the spaced-apart electrodes to span the electrode gap 139A. The bridge molecule 133A comprises first and second ends functionalized to bond to the electrode pair at conjugation points 131A and 132A.

FIG. 13-B shows the molecular structure of one specific example of a processive enzyme molecular sensor 130B, wherein the polymerase 134B is conjugated to a bridge molecule 133B comprising a 20 nm long (=6 helical turns) double-stranded DNA. The sensor 130B further comprises a pair of spaced apart chromium electrodes 138B and 139B, disposed on a substrate layer, such as $SiO_2$, and spaced apart at about 10 nm. On each electrode 138B and 139B are deposits of gold 131B that participate in the bonding of the bridge molecule to each of the electrodes. The DNA bridge molecule 133B shown is conjugated to the gold-on-chromium electrodes through thiol groups on first and second ends of the DNA bridge, binding to gold via sulfur-gold bonds 132B, and wherein the polymerase 134B is conjugated to the DNA bridge molecule 133B at a centrally located biotinylated base on the DNA bridge 135B, bound to a streptavidin molecule 136B, in turn bound to the polymerase 134B via a specific biotinylated site 135B on the polymerase 134B. In this way, the streptavidin 136B links the polymerase 134B to the DNA bridge molecule 133B by way of two biotin-streptavidin linkages 135B. The processive enzyme molecular sensor 130B is illustrated translocating a DNA substrate molecule 137B. As discussed, the DNA substrate molecule 137B may be encoded with information comprising arrangements of signaling features such as bound DNA oligonucleotide segments or perturbing groups.

FIG. 13-C shows embodiments of a processive enzyme molecular sensor 130C wherein the polymerase molecule 134C (also shown in FIG. 12-A) is conjugated directly into the current path between the electrodes, spanning the electrode gap 139C, by conjugation to two separate "arm" molecules 133C and 134C, which in turn are conjugated at one of their ends to each of the two electrodes via attachment points 136C and 137C, and to bonding sites on the enzyme 132C at conjugation points 135C and 138C, as shown. These embodiments illustrate how the conjugations of the arm molecules may be to the ends of an alpha-helix spanning the enzyme, to loop or sheet portions, or to other such protein anatomical structures (e.g., pointed out in FIG. 12-A) that preferentially channel the current through or near the active site of the enzyme or through or near portions of the enzyme that experience changes in conformation when interacting with a substrate molecule such as DNA molecule 131C shown.

FIG. 13-D shows embodiments of a processive enzyme molecular sensor 130D wherein the polymerase molecule 132D (also shown in FIG. 12-A) is conjugated directly to the each of the electrodes in a pair of spaced-apart electrodes to span the electrode gap 139D without any intervening arm or bridge molecules, in accordance with the general sensor structure of FIG. 4-C. The polymerase 132D is conjugated directly to the electrodes at attachment points 136D and 137D, wherein the attachment points may comprise thiol-gold bonds. These embodiments illustrate how the conjugations may be to the ends of an alpha-helix spanning the enzyme, to loop or sheet portions, or to other such protein anatomical structures (e.g., pointed out in FIG. 12-A) that preferentially channel the current through or near the active site of the enzyme or through or near portions of the enzyme that experience changes in conformation when interacting with a substrate molecule such as DNA molecule 131D shown.

FIG. 13-E shows embodiments of a processive enzyme molecular sensor 130E wherein the helicase enzyme molecule 132E (also shown in FIG. 12-B) is conjugated to a molecular bridge molecule 133E, at a specific conjugation point 135E comprising a specific binding site on both the helicase and the bridge molecule, in accordance to the general sensor structure shown in FIG. 4-A. The bridge molecule 133E comprises first and second ends, each bonded to the pair of electrodes at attachment points 136E and 137E. The conjugation point 135E between the helicase 132E and the bridge molecule 133E is chosen to bring the most active or variable parts of the helicase 132E, or the signaling groups bonded on the DNA substrate molecule 131E to be processively processed by the helicase 132E, in close proximity to the bridge molecule 133E for enhanced current modulation and enhanced signaling.

The electrical parameter measured in the processive enzyme molecular sensors described herein for distinguishable signals can in general be any electrical property of the circuit measurable while the sensor is active. In various embodiments, the parameter is the current passing between the two electrodes in a pair of spaced-apart and bridged electrodes versus time, either continuously or sampled at discrete times, when a voltage, fixed or varying, is applied between the electrodes. In various embodiments, there may also be a gate electrode, capacitively coupled to the molecular structure, such as a buried gate or back gate, which applies a gate voltage, fixed or variable, during the measurement. In various other embodiments, the measured parameter may be the resistance, conductance, or impedance between the two electrodes, measured continuously versus time or sampled periodically. The measured parameter could be the voltage between the electrodes. If there is a gate electrode, the measured parameter could be the gate voltage. The measured parameter could also be a capacitance, or the amount of charge or voltage accumulated on a capacitor coupled to the circuit. The measurement could be a voltage spectroscopy measurement, such that the measurement process comprises capturing an I-V or C-V curve. The measurement could be a frequency response measurement. In all such measurements, for all such measured parameters, there are embodiments in which a gate electrode applies a gate voltage, fixed or variable, near the molecular complex during the measurement. Such a gate will typically be physically located within a micron distance, and in some cases within a 200 nm distance, of the molecular complex bridging the pair of spaced-apart electrodes.

In various embodiments, for the electrical measurements there will be a reference electrode present, such as a Ag/AgCl reference electrode, or a platinum electrode, in the solution placed in contact with the sensor, and maintained at an external potential, such as ground, to maintain the solution at a stable or observed potential, and thereby make the electrical measurements more well defined or controlled. In addition, when making the electrical parameter measurement, various other electrical parameters may be held fixed at prescribed values, or varied in a prescribed pattern, such as, for example, the source-drain electrode voltage, the gate voltage if there is a gate electrode, or the source-drain current.

The use of the present processive enzyme molecular sensors to measure distinguishable features of a DNA molecule requires the processive enzyme to be maintained in the appropriate physical and chemical conditions to be enzymatically active, to process DNA templates, and produce strong, distinguishable signals above the background noise (i.e, for a high signal-to-noise ratio, or SNR). For this, the enzyme should reside in aqueous buffer solution, which, in various embodiments, will comprise salts, such as NaCl or KCl, pH buffers, such as Tris-HCl, multivalent cation cofactors, such as Mg, Mn, Ca, Co, Zn, Ni, other ions, such as Fe or Cu, surfactants, such as tween, chelating agents such as EDTA, reducing agents such as DTT or TCEP, solvents, such as betaine or DMSO, volume concentrating agents, such as PEG, and/or other components for enzyme buffers. The sensor signals may also be enhanced by maintenance of a buffer in a certain range of pH or temperature, or at a certain ionic strength. In particular, the ionic strength may be selected to obtain a Debye length (electrical charge screening distance) in the solution favorable for electrical signal production, which may be in the range of 0.3 nm-100 nm, or in the range of 1 nm-10 nm. Such buffers formulated to have larger Debye lengths may be more dilute or have lower ionic strength by a factor of 10, 100, 1000, 100,000 or 1 million relative to the buffer concentrations routinely used in standard molecular biology procedures such as PCR.

Buffer compositions, concentrations and conditions (e.g., pH, temperature, or ionic strength) may also be also selected or optimized to alter the enzyme kinetics to favorably increase the signal-to-noise ratio (SNR) of the sensor, the overall rate of signal production, or overall rate of information decoding in the context of reading data stored in DNA molecules. This may include slowing down or speeding up the processive enzyme activity by any combination of these variables. Optimal buffer selection process consists of selecting trial conditions from the matrix of all such parameter variations, empirically measuring a figure of merit, such as related to the discrimination of the distinguishable features, or to the overall speed of feature discrimination when processing a template, and using various search strategies, such as those applied in statistical Design Of Experiment (DOE) methods, to infer optimal parameter combinations.

In the case where the processive enzyme is a polymerase, the processing of the template DNA also requires that the polymerase be provided with a supply of dNTPs (deoxynucleoside triphosphates) so that it can act processively on a single-stranded DNA template molecule to synthesize a complementary strand. The standard or native dNTPs are dATP, dCTP, dGTP, and dTTP, which provide the A, C, G, and T base monomers for polymerization into a DNA strand, in the form required for the enzyme to act on them as substrates. Polymerase enzymes, native or mutant, may also accept analogues of these natural dNTPs or modified forms that may enhance or enable the generation of the distinguishable signals in accordance to the present disclosure.

Many such modified forms of DNTPs are known to those skilled in the field of nucleic acid biochemistry, and all such forms may be enabling for signal production in various embodiments of the processive enzyme molecular sensor. This includes dNTPs that have modification to the base, the sugar, and/or the phosphate group. For example, common forms include deaza-, thio-, bromo- and iodo-modifications at various sites on the molecule, or the inclusion of metal ions or different isotopes at various sites, the inclusion of a diverse variety of dye molecules at various sites, or methylation of various sites, or biotinylation of various sites. In particular, such modifications include forms that have an extended phosphate chain beyond the native tri-phosphate, such as to tetra-, penta-, hexa-, hepta- or more (4 or more, up to 11 or more) phosphates. Further, modifications may comprise addition of a chemical group to the terminal phosphate of this chain of phosphates, or any of the phosphates, except the alpha-phosphate or first in the chain, which are cleaved off during incorporation of the dNTPs into a complementary strand.

Polymerases are highly tolerant of such derivatization, and retain a high level of activity in their presence. In various embodiments, such modifying groups may provide different charge states, or different sizes, or different degrees of hydrophobicity to the dNTPs, which may aid in producing distinguishable signals. In various embodiments, groups added to dNTPs may interact selectively with sites on the bridge molecule or on the polymerase or the template DNA to produce distinguishable signals. In various embodiments, the dNTPs may be modified to include a group that interacts directly with the signal generating features indicated in FIG. 3-A or FIG. 3-B. For example, in the case where oligonucleotides are being displaced from an encoded DNA molecule, the dNTPs may be modified to comprise a group that interacts with the oligonucleotide being displaced, for example via hybridization to a complimentary portion of the oligonucleotide, or via interaction with a cognate group on the oligonucleotide. For example, the binding oligonucleotides and dNPTs may comprise complimentary oligonucleotides, or comprise other cognate binding partners such as biotin-avidin, or pyrenes that engage by pi-stacking, or many other such pairs, with one such partner in the pair being attached to the binding oligonucleotide, and the other cognate partner on a dNTP. In various embodiments, the binding group on the binding oligonucleotide feature of FIG. 3-A is only exposed for binding to its partner when the oligonucleotide is the next strand to be displaced by the polymerase, so that such interactions are preferentially occurring during the signaling process of FIG. 3-A.

Various embodiments of information encoding DNA molecular structures are shown in FIG. 14-A. In FIG. 14-A, DNA structure (A) comprises a series of oligonucleotides 142, 144, and so forth, bound to a template strand 140. Such oligonucleotides may be contiguous on the template strand, or have one or more bases such as 141, 143, and so forth separating them. Such oligonucleotides may be native DNA, or may comprise DNA analogues, such as RNA, PNA, LNA, XNA, or modified or analog bases or universal bases such as inosine or 5-nitroindole), or extended genetic code bases such as iso-dC and iso-dG. Such oligonucleotides 142, 144, and so forth may pair in a fully complementary fashion with the template 140, or may include mismatched base pairings. Such oligonucleotides may be selected to have substantially different melting point temperatures (Tm), such as near 30° C., near 40° C., near 50° C., near 60° C. or up to about 100° C. The template DNA 140 to which these oligonucleotides bind may comprise native DNA, or comprise analogues such as those just listed.

FIG. 14-A structure (B) is an information encoded DNA molecule in which the signaling features comprise bound oligonucleotides on the primary strand 140B, such as in structure (A), further comprising signal enhancing groups 145, 146, and so forth bound to the oligonucleotides. Such groups 145, 146, and so forth may be conjugated to the oligonucleotides in many ways, including, but not limited to, biotin-avidin binding, click chemistry, or conjugation to a free azide or amine group on the oligonucleotide. Such signal enhancing groups may comprise molecules carrying a formal charge in typical solutions, such as peptides or proteins including streptavidin, or molecules that are sterically bulky or have steric interactions with the processive enzyme, such as a PEG polymer, or molecules that are hydrophobic or hydrophilic, such as various peptides, or molecules that have specific interactions with the processive enzyme, native or genetically modified, or interactions with any of the other components of the molecular complex. Such interactions may be provided by one member of cognate binding partners bonded on the oligonucleotide and the other on the enzyme, the molecular bridge molecule, or the molecular complex For example, complementary oligonucleotides may be attached to the bound oligonucleotide and the processive enzyme or bridge molecule.

Structures (C) and (D) shown in FIG. 14-A represent further embodiments of DNA molecules encoded with information, such as discussed in the context of FIGS. 3-A and 3-B. In structure (C), signaling features 145', 146', and so forth, such as described for structure (B), are bound to a single stranded DNA template strand 140C. In structure (D), the signaling features 145", 146", and so forth are bound to a double-stranded DNA template 140D.

FIG. 14-B illustrates template structure embodiments (or strand architectures) that allow the data payload from a single molecule to be read multiple times by the same processive enzyme sensor. Various molecular biology methods enable a processive enzyme sensor to interrogate the same DNA molecule repeatedly. Three such embodiments of encoding template structural schematics are shown in FIG. 14-B. The first structural schematic, (A), is a circularized template molecule. For processive enzymes that can engage a circular template without damaging the template, (such as a polymerase, helicase or packaging motors that do not have to "thread" their template but instead clamp on from the side), are able to process around the circular template multiple times, and thus process the same signaling features multiple times. As discussed, such features capable of being processed multiple times include, for example, the permanently bound groups of FIGS. 14-A (C) and (D), or, in the case of displaceable oligonucleotide features, as in FIGS. 14-A (A) and (B), so long as such oligonucleotides are rapidly re-bound to the template after displacement. For oligonucleotides to re-bind to the template, they may be replenished from a local concentration in solution and multiply read. The second structural schematic (B) of FIG. 14-B is a hair pinned single strand forming a double stranded region. Suitable processive enzymes that will process one strand of a double stranded molecule, such as strand displacing polymerases, some helicases, some packaging motors, and some exonucleases, go around the hairpin and process the other complementary strand, and thus can in effect read twice the information that is doubly represented as permanently bound groups on both strands. The third structural schematic (C) of FIG. 14-B is a DNA encoding molecule wherein the data payload is simply repeated in tandem, one or more times, so that the processive enzyme will trivially process through these multiple copies of the same DNA data payload, thus reading it multiple times.

Figure 15:
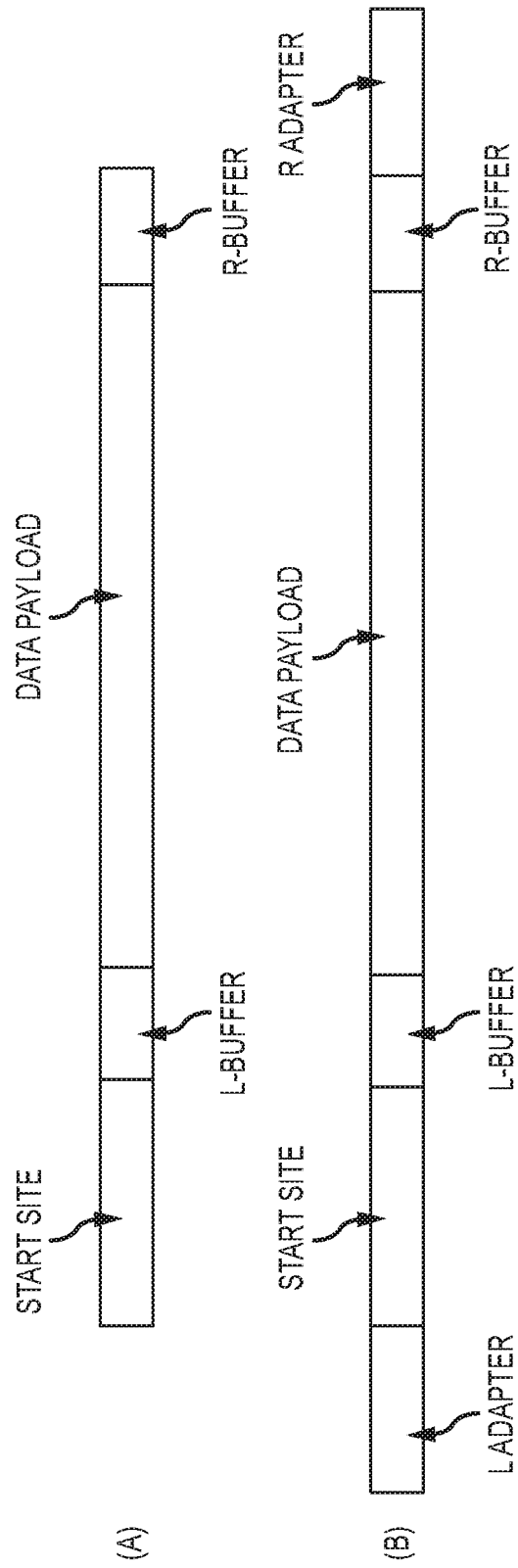
FIG. 15 shows various embodiments of the logical structure for DNA data storage molecules, comprising handling adapters, a start site for the processive enzyme to engage, buffer segments, and a data payload segment encoding the primary binary data payload.

The DNA molecules comprising encoded information for reading by the cognate processive enzyme molecular sensor, being of synthetic and designed origin, may be prepared with an architecture that facilities the reading process as well as the encoding (its synthesis) and decoding (the reading) processes. Such architectures are illustrated in FIG. 15 by structural embodiments (A) and (B). Overall, FIG. 15 illustrates structures of information carrying DNA fragments. In structure (A), the START SITE segment is a primer segment containing primer target/structure where the processive enzyme will bind and initiate the processing of the rest of the strand. The L-BUFFER segment may contain signal calibration sequence for the reader, or buffering sequence prior to the DATA PAYLOAD segment, which contains information storing encoded sequence, and related error correction sequence such as parity bits. The R-BUFFER segment may contain additional calibration sequence, as well as buffer sequence allowing for the enzyme to avoid getting too close to the end of the template when reading data. Left and/or Right buffer regions may comprise DNA segments required to support the polymerase binding footprint, or various calibration or initiation sequences used to help interpret the signals coming from the DATA PAYLOAD region. These buffer segments could also contain molecular barcode sequences that are used to uniquely distinguish molecules, or identity replicate molecules that are derived from the same originating single molecule. One such method of barcoding, known to those skilled in DNA oligonucleotide synthesis, comprises addition of a short random N-mer sequence, typically 1 to 20 bases long, as is commonly made by carrying out synthesis steps with degenerate mixtures of bases instead of specific bases. Finally, there is a DATA PAYLOAD segment, where the specific data is encoded, which may include primary digital data being stored, as well as data related to proper assembly of such information fragments into longer strings, and also data related to error detection and correction, such as parity bits, check sums, or other such information overhead.

In structure (B) of FIG. 15, L-ADAPTER and R-ADAPTER segments may be sequence elements related to the storage or manipulation of the associated DNA segment, such as adapters for outer priming cites for PCR amplification, or hybridization based selection, or representing a surrounding carrier DNA for this insert, including insertion into a host organism genome as a carrier. These right and left adapters may comprise primers for universal amplification processes, used to copy the stored data, or may comprise hybridization capture sites or other selective binding targets, for targeted selection of molecules from a pool, for example. Such adapters may comprise surrounding or carrier DNA, for example in the case of DNA data molecules stored in live host genomes, such as in bacterial plasmids or other genome components of living organisms. The DATA PAYLOAD in general may include the actual primary data being archived, as well as metadata for the storage method, such as related to the assembly of this information into larger strings, or error detection and correction.

The DATA PAYLOAD DNA structure results from a sensor-specific information encoding scheme applied to a source digital data payload, such as binary data, as illustrated in FIG. 16. In this scenario, the originating digital data that is being stored as DNA will typically have a prior representation as electronic binary data. This originating data will then be divided into segments, and be augmented by re-assembly data, and also transformed by error correcting encodings appropriate for DNA data storage, to produce actual binary data payload segments, such as in FIG. 16, that then require translation to DNA payload sequences for subsequent DNA synthesis to produce the physical storage molecules. This primary translation is what, in various embodiments, is performed by Binary Encoding Schemes (BES) such as those exemplified in FIG. 16. These encoding schemes provide primary translation from a digital data format, such as binary, to a DNA molecular sequence format, via first producing a list of distinguishable signaling features that imply corresponding DNA segments, which are assembled for the encoding DNA molecule.

Choosing which BES is appropriate depends, in part, on the type of distinguishable signal features and their arrangements, as discussed in the context of FIG. 1-B and illustrated in the inset of FIG. 1-B. FIG. 16 illustrates several such primary encodings, beginning with an exemplary binary data payload, a particular 16-bit word "1010100110011100," and converting the binary data to one or more distinguishable signal features for the encoded DNA molecule.

With continued reference to FIG. 16, exemplary binary encoding schemes (BES) shown include: BES1, encoding 1 bit into 2 distinguishable signaling features F1 and F2, for use with a DNA reading sensor that can distinguish these features; BES2, encoding combinations of two binary bits 00, 01, 10 and 11 into four features, F1, F2, F3 and F4, for use with a DNA reading sensor that distinguishes these features; and BES3, encoding the binary strings 0, 1 and 00 into 3 distinguishable features F1, F2 and F3. FIG. 16 illustrates the encoding of the binary data payload for these BES, in terms of conversion of the binary string into a feature string, which must then be realized in DNA. Codes that produce shorter sequences are preferred if reducing the length of synthesized DNA information encoding molecules is preferred, which may exist for example, due to practical limitations on oligonucleotide length for the writing technology.

It is understood that the BES exemplified in FIG. 16 are non-limiting, and many variations or similar encoding schemes to those shown in FIG. 16 are also implicit in these examples, such as by permuting the features used. It is also understood that all such encoding schemes must have a cognate sensor that is capable of distinguishing the signals of the encoding features, so that the choices of BES are directly related to the properties of the sensor in distinguishing features. It is understood that digital data formats or alphabets other than binary, such as hexadecimal, decimal, ASCII, etc., can equally well be encoded into DNA signaling features by similar schemes as those of FIG. 16. Such methods are well known to those skilled in the field of computer science. Schemes more sophisticated than those shown, in terms of optimal information density, such as Lempel-Ziv encoding, can highly efficiently convert and compress data from one alphabet into another. In general, for converting a binary or other digital data payload string or collection of strings, into a DNA sequence string, or collection of such strings, many of the methods of lossless and lossy encoding or compression, well known in computer science, can be used to devise schemes for the primary conversion from input digital data payloads to DNA data payloads of the forms such as the embodiments of FIG. 14.

For one illustrative example of such how the encoding is used to define a DNA sequence for synthesis, consider a sensor which has as distinguishable signaling features that are the oligonucleotides 5'-CCCC-3' (SEQ ID NO: 3) and 5'-GGGG-3' (SEQ ID NO: 4) and 5'-AAAA-3' (SEQ ID NO: 5) bound to the respective reverse complement template segments F1=5'-GGGG-3' (SEQ ID NO: 4), F2=5'-CCCC-3' (SEQ ID NO: 3) and F3=5'-TTTT-3' (SEQ ID NO: 6). Suppose the BES3 of FIG. 16 is used, and the input binary data payload is 01001. The conversion to a feature sequence would be F1F2F3F1. This could be directly converted to a DNA data payload segment of the DNA encoding molecule with architecture as in FIG. 15, as 5'-GGGGCCCCTTTTGGGG-3' (SEQ ID NO: 7). Or, in other embodiments, there may be "punctuation" sequence segments inserted between the distinguishable signal features, which do not alter the distinguishable features, e.g., bound oligonucleotides, but may provide benefits such as accommodating special properties or constraints of the DNA synthesis chemistry, or to provide spacers for added time separation between signal features, or reduced steric hindrance, or to improve the structure of the DNA molecule. For example, if A were such a punctuation sequence, the DNA encoding sequence would become 5'-AGGGGACCC-CATTTTAGGGGA-3' (SEQ ID NO: 8). In general, such insertion of punctuation sequences or filler sequences may be part of the process of translating from a digital data payload to the encoding DNA sequence to be synthesized.

For robust recovery of digital data from DNA storage, a DNA data payload of interest may be processed by a processive enzyme sensor multiple times, or, for a collection of such payloads, they on average may be processed some expected number of multiple times. This repetition has the benefit of providing a more accurate estimation of the encoding distinguishable features by aggregating such multiple observations. This also has the benefit of overcoming fundamental Poisson sampling statistical variability to ensure that, with high confidence, a data payload of interest is sampled and observed at least once, or at least some desirable minimal number of times. In various embodiments, the desired number or expected number of such repeat interrogations may be in the range of 1 to 1000. In other embodiments, the number or expected number may be in the range of 3 to 30.

Such multiple observations may be via either of or a combination of: repeated observations of the same physical DNA molecule by the processive enzyme sensor, or by one or more processive enzyme sensors processing multiple, physically distinct DNA molecules that carry the same data payload. In the latter case, such multiple, physically distinct DNA molecules with the same data payload may be the DNA molecules produced by the same bulk synthesis reaction, or may be molecules from distinct such synthesis reactions targeting the same data payload, or may be replicate molecules produced by applying amplification or replication methods such as PCR, T7 amplification, rolling circle amplification, or other forms of replication known to those skilled in molecular biology. The aggregation of such multiple observations may be done through many methods, such as averaging or voting, maximum likelihood estimation, Bayesian estimation, hidden Markov methods, graph theoretic or optimization methods, or deep learning neural network methods.

In various embodiments, the digital data stored in DNA is read at a high rate, such as approaching 1 Gigabyte per second for recovering the digital data, as is possible with large scale magnetic tape storage systems. Because the maximum processing speed of a processive enzyme such as a polymerase is in the range of 100-1000 bases per second, depending on the type, the bit recovery rate of one sensor is limited to a comparable speed, and so it is highly desirable to deploy millions of sensors in a cost effective format to achieve the desired data reading capacity. In various embodiments, the sensors can be deployed as a large scale sensor array on a CMOS chip, which is the most cost-effective, semiconductor chip manufacturing process.

FIG. 17-A shows an embodiment of the fabrication stack in which the sensor measurement circuitry is deployed as a scalable pixel array as a CMOS chip, a nano-scale lithography process is used to fabricate the nano-electrodes, and molecular self-assembly chemical reactions, in solution, are used to establish the molecular complex on each nano-electrode in the sensor array. The result of this fabrication stack is the finished DNA reader sensor array chip indicated at the bottom of FIG. 17-A. In certain embodiments of this fabrication stack, the nanoscale lithography is done using a high resolution CMOS node, such as a 28 nm, 22 nm, 20 nm, 16 nm, 14 nm, 10 nm, 7 nm or 5 nm nodes, to leverage the economics of CMOS chip manufacturing. In contrast, the pixel electronics may be done at a coarser node better suited to mixed signal devices, such as 180 nm, 130 nm, 90 nm, 65 nm, 40 nm, 32 nm or 28 nm. Alternatively, the nano-electrodes may be fabricated by any of a variety of other means known to those skilled in the art of nanofabrication, such as e-Beam Lithography or Nano-imprint lithography, or ion beam lithography, or advanced methods of photolithography such any combinations of Extreme UV or Deep UV lithography, multiple patterning or phase shifting masks.

FIG. 17-B illustrates an embodiment of a high-level CMOS chip pixel array architecture for a DNA reader in more detail at the left of the drawing figure. The CMOS chip pixel array architecture comprises a scalable array of sensor pixels, with associated power and control circuitry and major blocks such as Bias, Analog-to-Digital convertors, and timing. The inset in the figure shows an individual sensor pixel as a small bridged structure representing a single processive enzyme molecular sensor, and where this individual electronic sensor is located in the pixel array. FIG. 17-B also illustrates (at the right side of the figure) the details of an embodiment of a processive enzyme molecular electronics sensor circuit pixel in the array. As illustrated, a complete sensor circuit comprises a trans-impedance amplifier, voltage-biasable source, drain, and (optionally) gate electrodes, and a reset switch, along with a processive enzyme electrically connected between the source and drain electrodes (with or without bridge and/or arm molecules). The feedback capacitor illustrated is optional to improve stability of the amplifier. The output of the pixel circuit (the measurable electronic parameter) in this embodiment is current, which is monitored for perturbations relating to the activity of the processive enzyme. That is, the current output from the trans-impedance amplifier is the measurable electrical parameter for this sensor pixel that is monitored for perturbations. It should be noted that one of the two electrodes can be grounded, in which case a biasable voltage is supplied across the electrodes.

Figure 18:
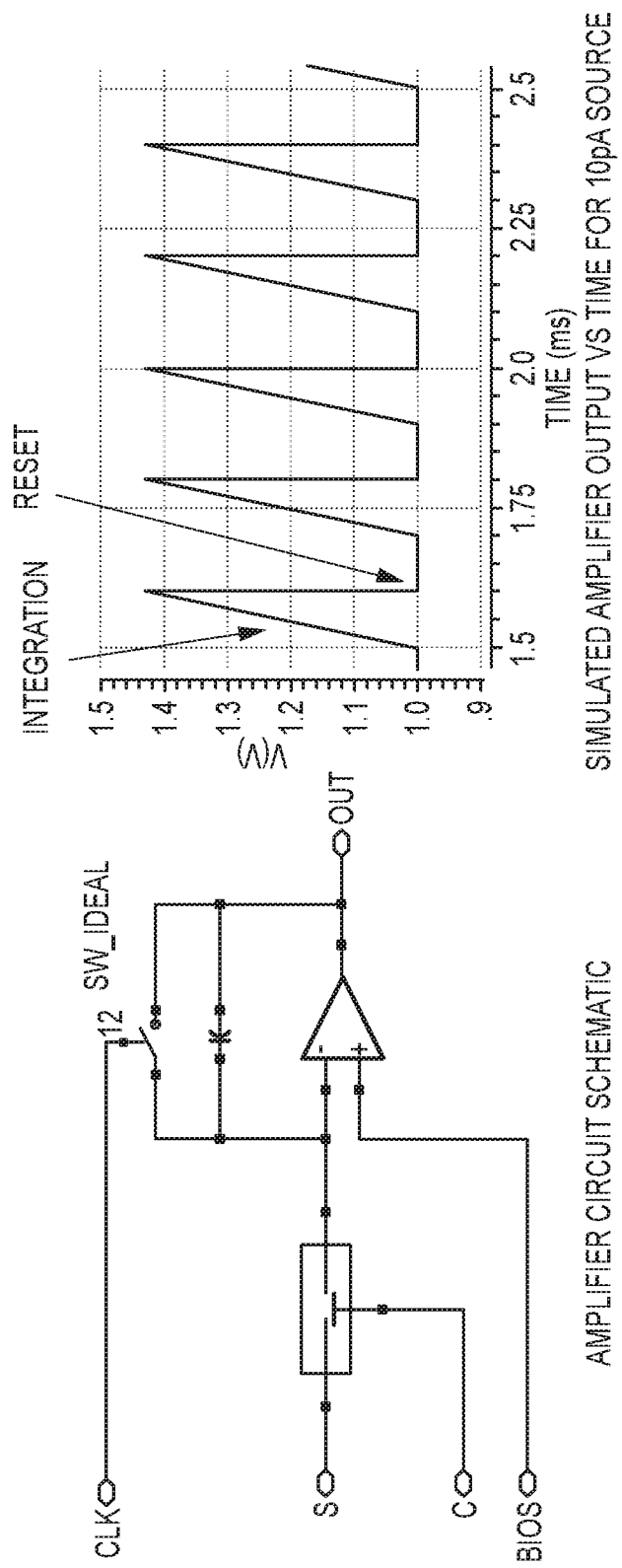
FIG. 18 shows an embodiment of a circuit schematic and the resulting measurement for the pixel circuit of FIG. 17-B, comprising sensing of a 10 pA current, for one possible choice of circuit parameters (transistor properties, resistors and capacitors)

FIG. 18 shows an embodiment of a circuit schematic of the pixel amplifier in detail at the left side of the figure, along with simulation results at the right side of the figure showing the voltage signal vs time when used to measure a 10 pA current, and with a reset applied periodically as indicated in the plot. This embodiment exemplifies one non-limiting selection of circuit components and parameters (transistor, resistors, capacitors, etc.).

Figure 19:
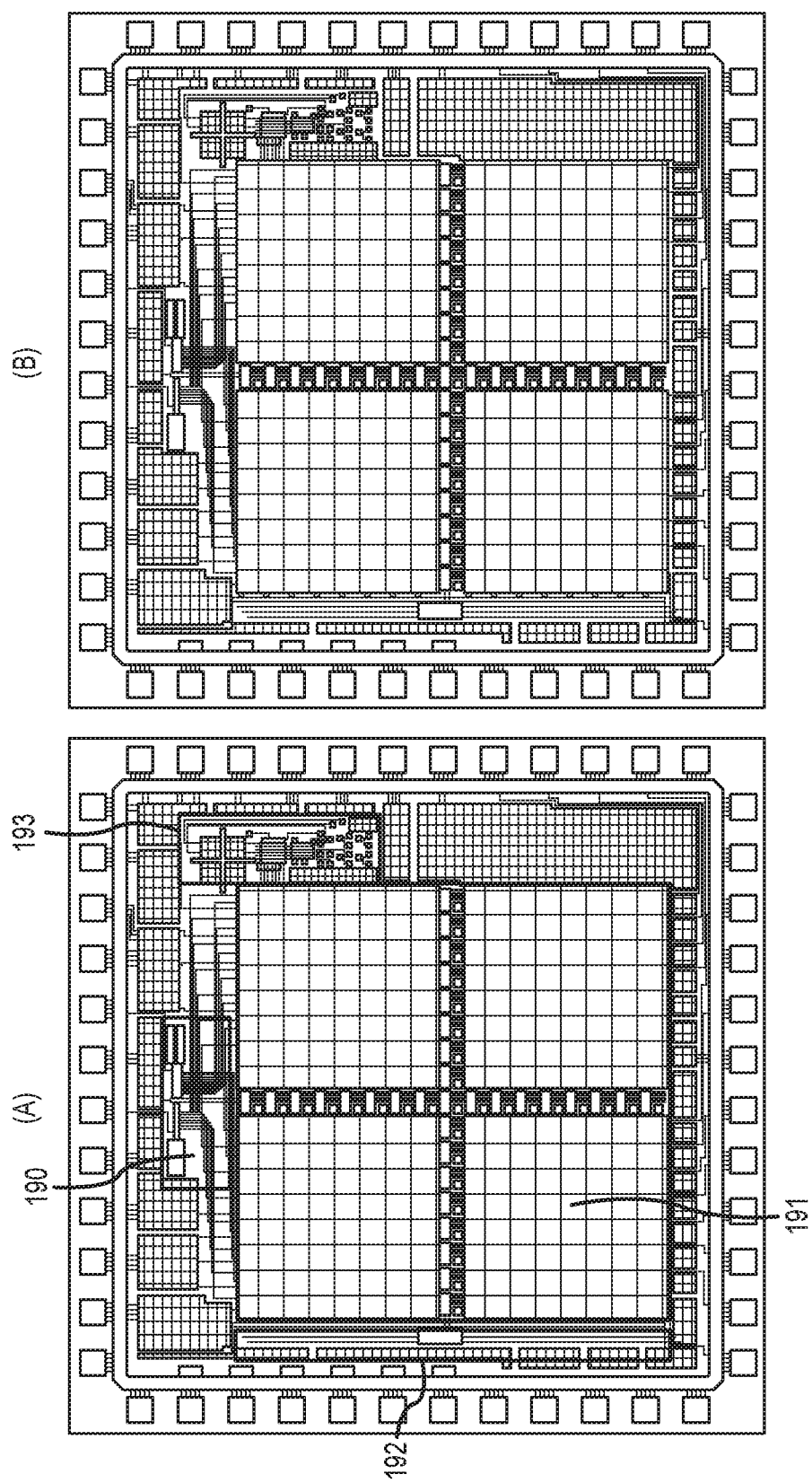
FIG. 19 shows the completed, annotated chip design, and a drawing of an optical microscope image of the fabricated chip, for an embodiment of the pixel array chip of FIG. 17-B having an array of 256 pixels.

FIG. 19 illustrates an embodiment of an annotated chip design layout file and the corresponding finished chip for comparison. In FIG. 19, (A), at left, is the finished design of an embodiment of the CMOS pixel array of FIG. 17-B with 256 pixels, annotated to show the location of the Bias 190, Array 191 and Decoder 192 regions of the chip. The design layout also comprises a test structures 193 region. In FIG. 19, (B), at right, is a drawing of an optical microscope image of the corresponding finished chip based on the final design, produced at TSMC, Inc. semiconductor foundry (San Jose, Calif.) with the TSMC 180 nm CMOS process, with no passivation layer.

Figure 20:
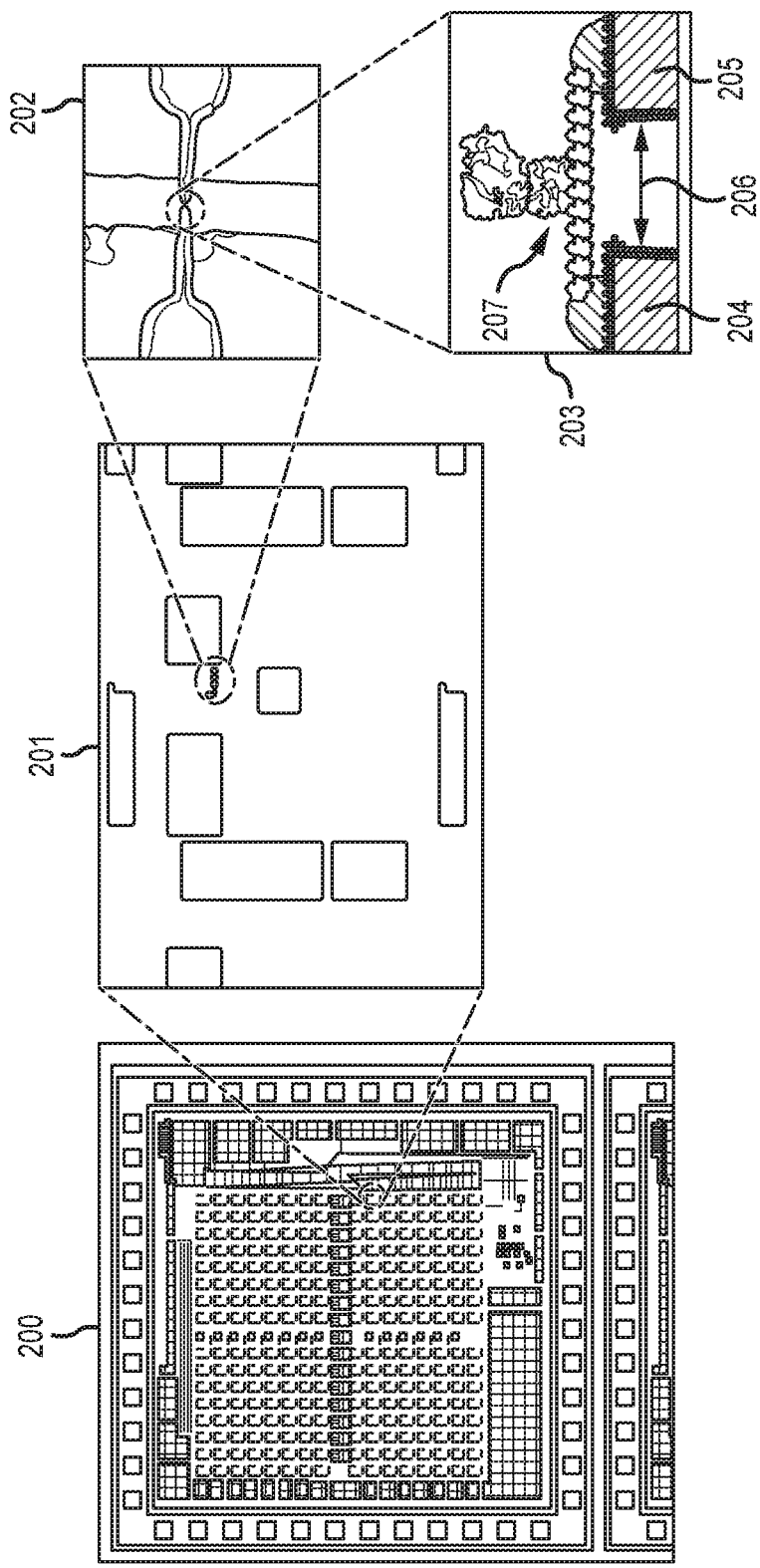
FIG. 20 shows a drawing of an electron microscope image of the fabricated chip of FIG. 19, including insets of the nano-electrode with a polymerase processive enzyme molecular complex in place.

FIG. 20 shows illustrations of scanning electron microscope (SEM) images of the finished CMOS chip 200 of FIG. 19 (256 pixel array, 2 mm×2 mm), which clearly shows the sub-optical surface features of the 80 µm pixel 201, and notably the exposed vias (the source, gate, and drain) where the nano-electrodes can be deposited by post-processing and electrically connected into the amplifier circuit as shown in FIG. 17-B, at right. The furthest right drawing of a 100 nm SEM image 202 in FIG. 20 shows an e-beam lithography fabricated pair of spaced apart nanoelectrodes with a molecular complex in place. The sketch 203 at the bottom right of FIG. 20 is an illustration of the processive enzyme molecular electronics sensor comprising a polymerase molecular complex 207, spaced apart electrodes 204 and 205, each labeled by a gold dot contact, wherein the electrode gap 206 is about 10 nm.

In various embodiments of the present disclosure, a DNA reader chip for use herein comprises at least 1 million sensors, at least 10 million sensors, at least 100 million sensors, or at least 1 billion sensors. Recognizing that a typical sensor data sampling rate may be 10 kHz, and recording 1 byte per measurement, a 100 million sensor chip produces raw signal data at a rate of 1 Terabyte (TB) per second. In considering how many sensors are desirable on a single chip, one critical consideration is the rate at which such a chip can decode digital data stored in DNA, compared to the desirable digital data reading rates. It is, for example, desirable to have digital data read out at a rate of up to 1 Gigabyte per second. Note that each bit of digital data encoded as DNA will require multiple signal measurements to recover, given that a feature of the signal use used to store this information, so this raw signal data production rate for the measured signal will be much higher that the recovery rate of encoded digital data. For example, if 10 signal measurements are required to recover 1 bit of stored digital data, as might be the case for signal features such as in FIG. 2, and each measurement is an 8-bit byte, that is a factor of 80 bits of signal data to recover 1 bit of stored digital data. Thus, digital data reading rates are anticipated to be on the order of 100 times slower than the sensor raw signal data acquisition rate. For this reason, achieving desirable digital data reading rate of 1 Gigabyte/second would require nearly 0.1 TB/second of usable raw signal data. Given that not all sensors in a chip may be producing usable data, the need for chips that produce up to 1 TB/sec of raw data is desirable, based on the desired ultimate digital data recover rates from data stored as DNA. In various embodiments, such recovery rates correspond to a 100 million sensor chip.

Figure 22:
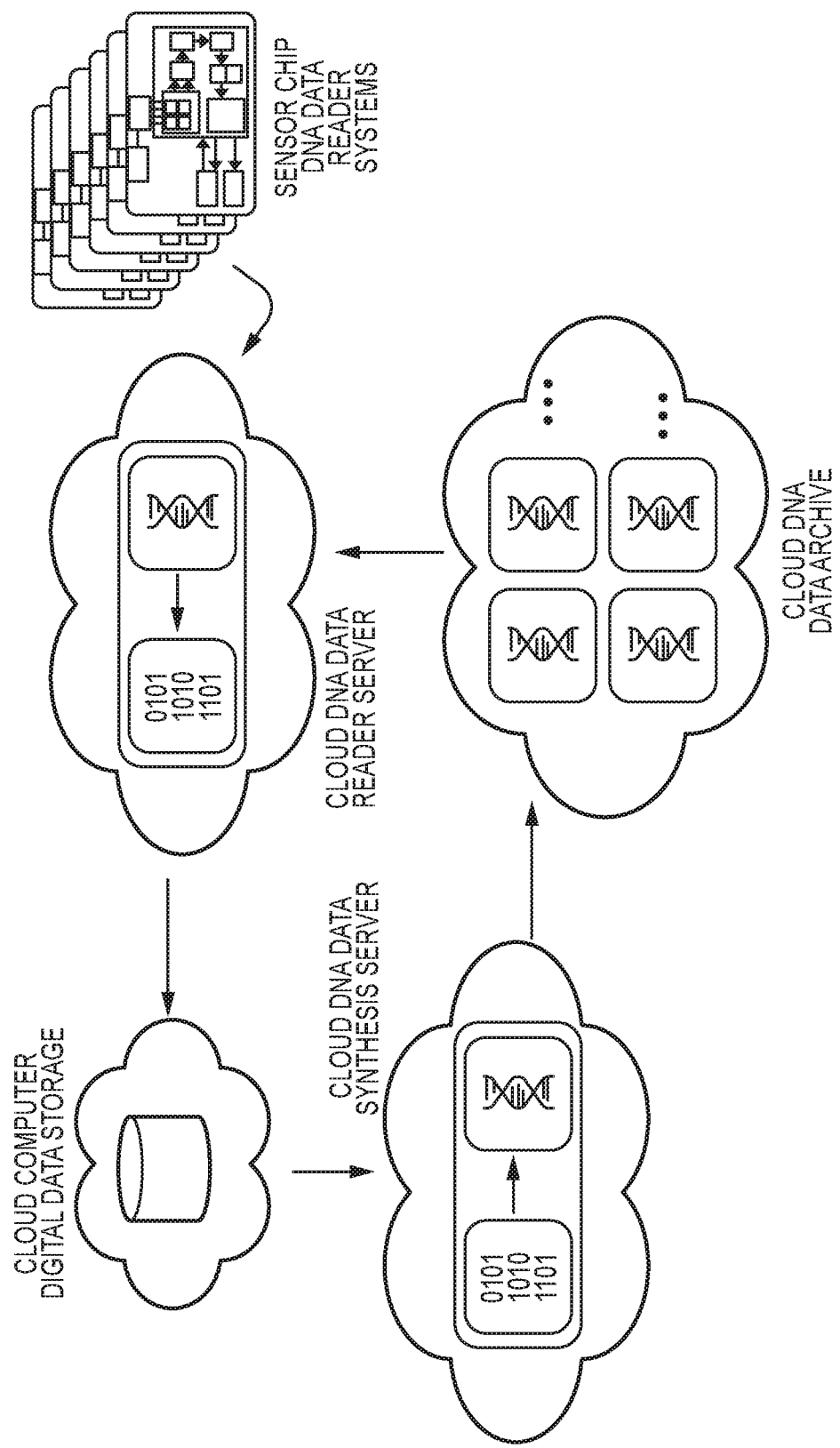
FIG. 22 shows a schematic of a cloud-based DNA data archival storage system, in which a multiplicity of the DNA reading system of FIG. 21 are aggregated to provide the data reader server.

In various embodiments of the present disclosure, multiple chips are deployed within a reader system to achieve desired system-level digital data reading rates. The DNA data reader chip of FIG. 17-A may be deployed as part of a complete system for reading digital data stored in DNA. The features of such a system are indicated in FIG. 22. In various aspects, and with reference to FIG. 22, a complete digital data reading system comprises a motherboard with a staging area for an array of multiple chips, in order to provide data reading throughput beyond that of the limitations of a single chip. Such chips are individually housed in flow cells, with a fluidics liquid handling system that controls the additional and removal of the sensor system liquid reagents. In addition, the fluidics system receives DNA encoding data in solution form, originating from a data repository source. The motherboard would also comprise a suitable first stage data processing unit, capable of receiving and reducing raw signal data at very high rates, such as exceeding 1 TB per second, or exceeding 10 TB per second, or exceeding 100 TB per second, indicated as a primary signal processor. This primary processor may comprise one, multiple, or combinations of a FPGA, GPU, or DSP device, or a custom signal processing chip, and this may optionally be followed by stages of similar such signal processors, for a processing pipeline. Data output of this primary pipeline is typically transferred to a fast data storage buffer, such as a solid state drive, with data from here undergoing further processing or decoding in a CPU-based sub-system, from which data is buffered into a lower speed mass storage buffer, such as a hard drive or solid state drive or array of such drives. From there it is transferred to an auxiliary data transfer computer sub-system that handles the subsequent transfer of decoded data to a destination. All these system operations are under the high-level control of an auxiliary control computer that monitors, coordinates and controls the interplay of these functional units and processes.

In some embodiments, chips within the reader system may be disposable, and replaced after a certain duty cycle, such as 24 hours to 48 hours. In other embodiments, the chips may be reconditioned in place after such a usage period, whereby the molecular complex, and possibly conjugating groups, are removed, and then replaced with new such components through a serious of chemical solution exposures. The removal process may comprise using voltages applied to the electrodes to drive removal, such as an elevated violated applied to the electrodes, or an alternating voltage applied to the electrodes, or a voltage sweep. The process may also comprise the use chemicals that denature, dissolve or dissociate or otherwise eliminate such groups, such as high molarity Urea, or Guanidine or other chaotropic salts, proteases such as Proteinase K, acids such as HCl, bases such as KOH or NaOH, or other agents well known in molecular biology and biochemistry for such purposes. This process may also include the use of applied temperature or light to drive the removal, such as elevated temperature or light in conjunction with photo-cleavable groups in the molecular complex or conjugation groups.

Figure 21:
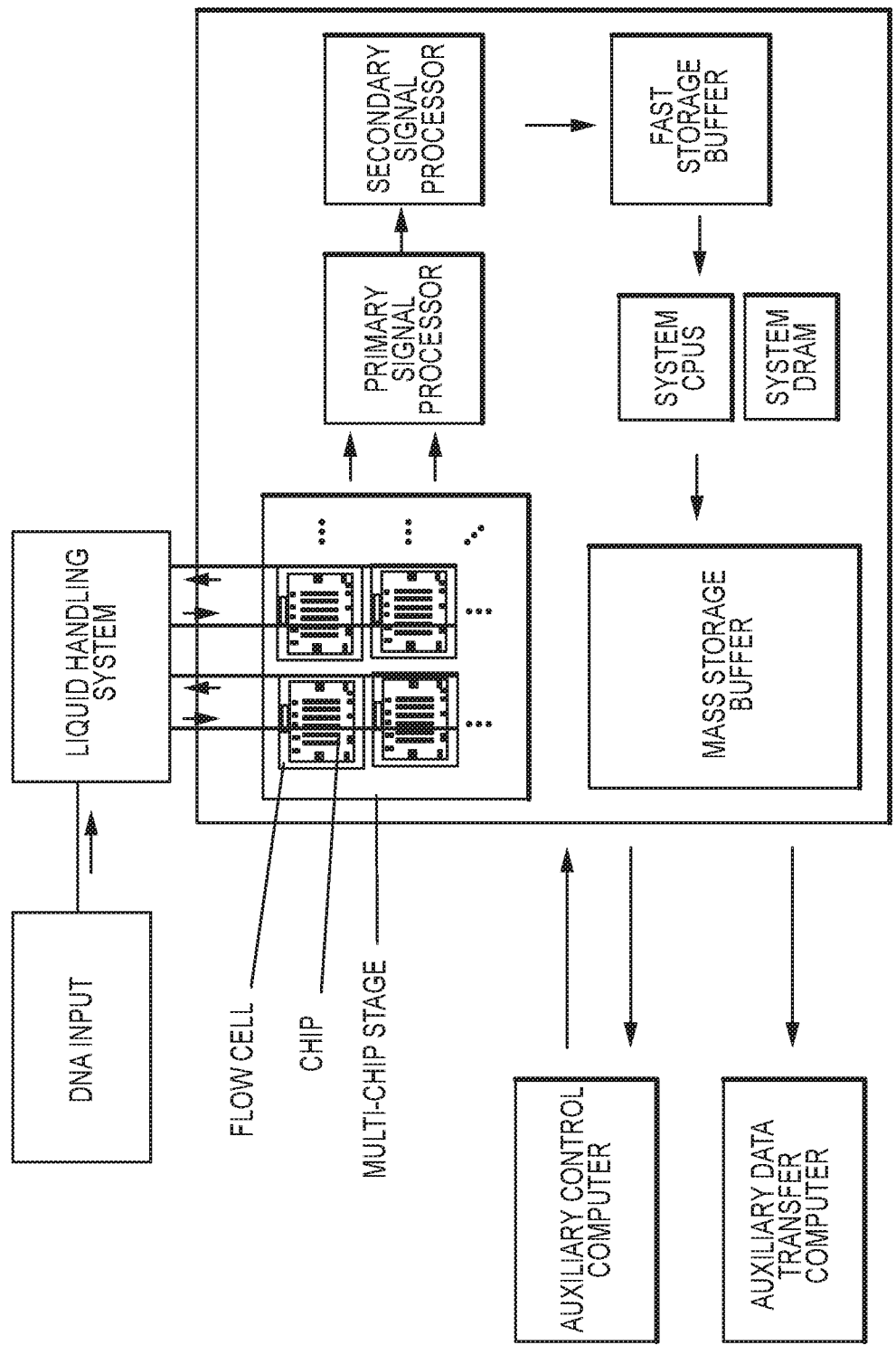
FIG. 21 shows a schematic of a complete system for reading DNA data with chip-based DNA reader comprising processive enzyme molecular electronic sensors.

FIG. 22 illustrates n embodiment of a cloud based DNA data archival storage system, in which the complete reader system such as outlined in FIG. 21 is deployed in aggregated format to provide the cloud DNA reader server of the overall archival storage and retrieval system. FIG. 22 shows a cloud computing system, with a standard storage format (upper left). Such a standard cloud computing system is provided with DNA archival data storage capability as indicated. Some cloud-based DNA synthesis system can accept binary data from the cloud computer, and produce the physical data encoding DNA molecules. This server stored the output molecules in a DNA data storage archive, lower right, where typically the physical DNA molecules that encode data could be stored in dried or lyophilized format, or in solution, at ambient temperature or cooled or frozen. From this archive, when data is to be retrieved, a DNA sample from the archive is provided to the DNA data reader server, which outputs decoded binary data back to the primary cloud computer system. This DNA data reader server may be powered by a multiplicity of DNA reader chip-based systems of the kind indicated in FIG. 21, in combination with additional computers that perform the final decoding of the DNA derived data back to the original data format of the primary cloud storage system.

Figure 23:
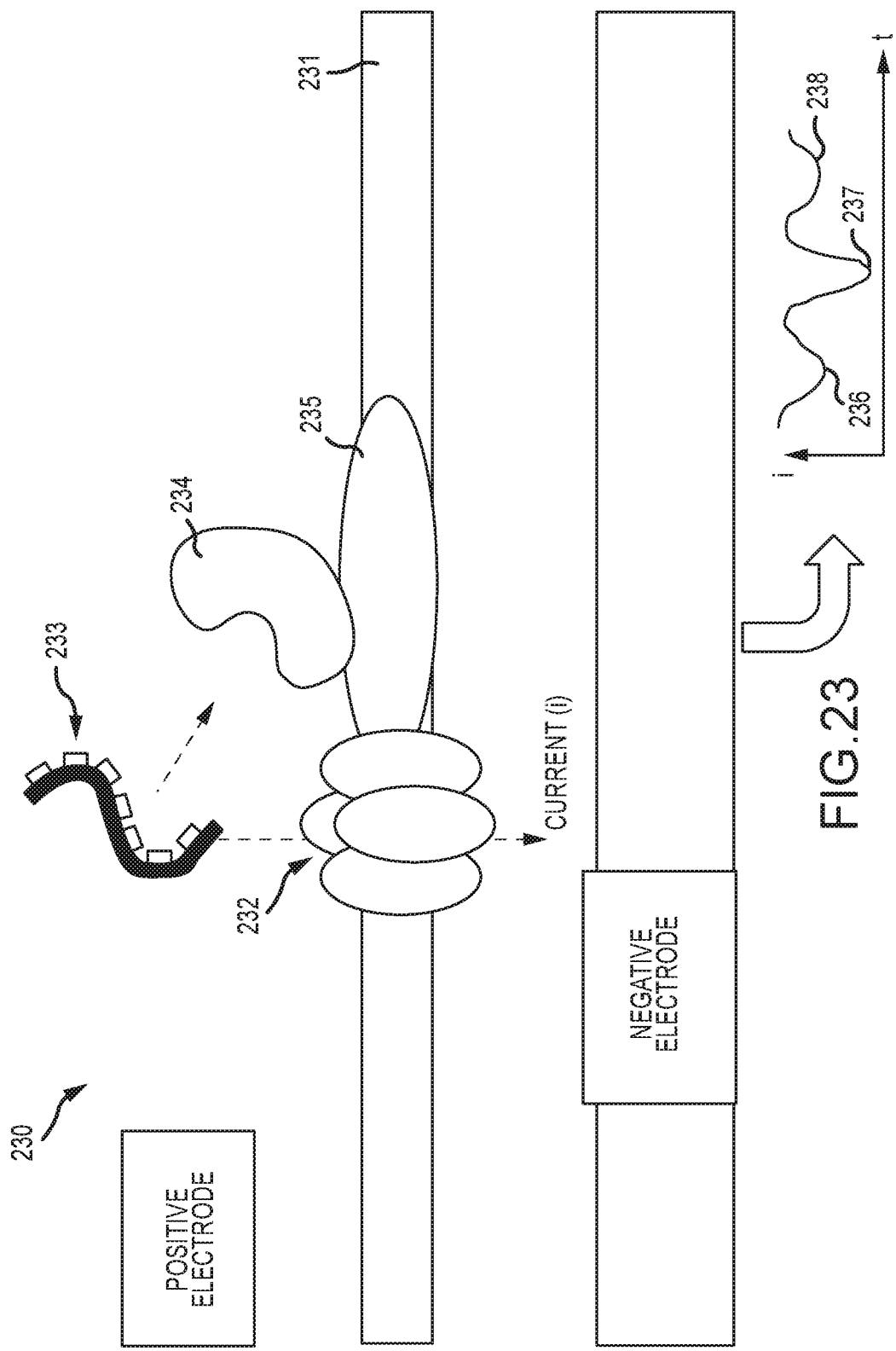
FIG. 23 shows an alternate embodiment of a DNA data reader sensor in which a processive enzyme is complexed with a different electronic sensor configuration than in FIG. 1, here a nanopore ion current sensor, and which produces distinguishable signal features in the nanopore ion current when processing a DNA template molecule having signaling features.

Alternative embodiments of processive enzyme molecular sensors relying on a different nano-electronic measurement configuration than the sensors of FIG. 1-B, is shown in FIG. 23. As shown, the processive enzyme molecular sensor 230 comprises a membrane 231 disposed between positive and negative electrodes. In these sensors, the electronic measurement is made by a nanopore ionic current sensor comprising the electrodes on either side of the membrane 231, a pore 232 localized in the membrane 231 that regulates the passage of ionic current (shown as "CURRENT (i)" passing through the pore), and aqueous solution residing on both sides of the pore 232. The sensor 230 further comprises a processive enzyme 234 bonded to another molecule 235 embedded in the membrane 231, or bonded directly to the membrane 231. As the processive enzyme 234 processes the DNA substrate 233 having distinguishable signaling features bonded thereto, ions generated on the processing side of the membrane 231 pass through the pore 232 due to the ion gradient. Such nanopore current sensors are well known to those skilled in the art of biological ion channels, or biophysics. In various embodiments, the pore 232 comprises a biological protein nanopore, native or mutated, and the membrane 231 comprises a lipid membrane, or synthetic analogue thereof. Various pores may comprise a solid state pore, and the membrane a thinned membrane composed of a solid material, such as SiN or Teflon. In various embodiments, the positive and negative electrodes may be reversed from what is illustrated, such as depending on the formal charge of the ions in the ion gradient. As the ions generated in the processive action of the enzyme pass through the pore, the changes in the ionic current are seen as perturbations 236, 237, 238, and so forth in the (i) versus (t) plot shown in the inset in the figure. As shown in FIG. 23, the processive enzyme 234 is further complexed with the pore 232 by a variety of ways, such as being part of a molecular complex involving a small number of molecules 235 embedded in the membrane 231 and associated with the pore 232. As the enzyme 234 processes a DNA template 233, with signaling groups or features shown bonded thereon, the ionic current through the pore is modulated by this activity, producing distinguishable signal perturbations 236, 237, 238, and so forth that correspond to the distinct template signaling features on the DNA template.

Figure 24:
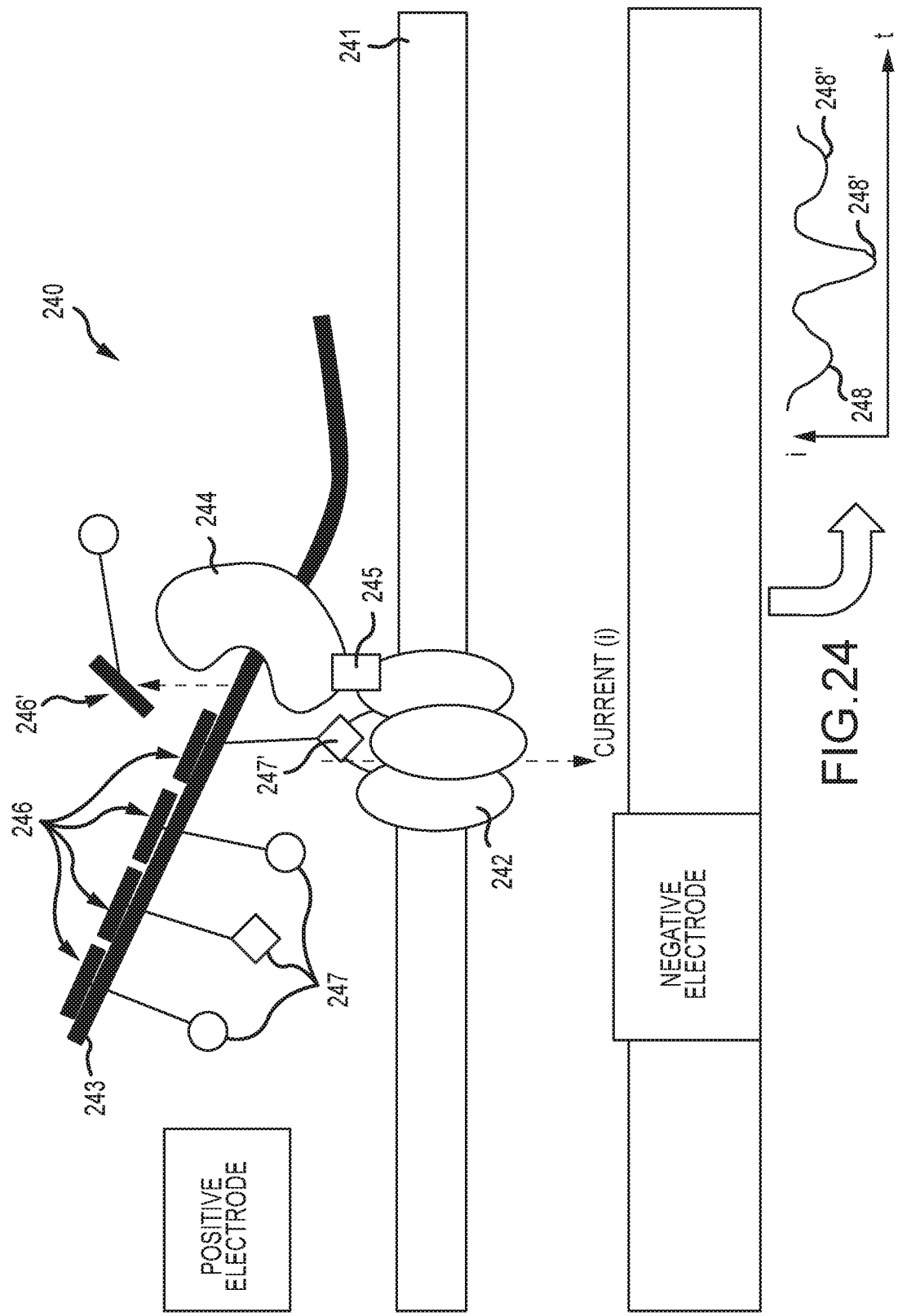
FIG. 24 shows an embodiment of DNA data reader sensor of FIG. 23, in which the Helicase is directly conjugated to the nanopore, and in which the signaling groups are oligonucleotides bound to the DNA template, which further carry groups that alter the current in the nanopore sensor as they are translated past the pore by the action of the Helicase.

Other embodiments of the nanopore current sensor version of the processive enzyme-based DNA digital data reader are shown in FIG. 24. In various embodiments, the processive enzyme molecular sensor 240 comprises a processive enzyme 244 directly conjugated to the pore 242 in the membrane 241 at a specific conjugation point 245. The processive enzyme 244 may comprise a helicase. When a DNA template 243 encoded with signaling features 246 is provided to the enzyme 244, distinguishable signals, (248, 248', 248", and so forth), result in the (i) versus (t) plot as shown in the inset in the drawing figure, comparable to the situation illustrated in FIG. 6. In certain aspects, the oligonucleotides 246 bonded to the primary strand 243 may comprise attached groups 247 capable of occluding the pore 242 while the oligonucleotides 246 engage with the enzyme 244, thereby resulting in current suppression features. As illustrated, group 247' is capable of occluding the pore 242 when adjacent to, or processed by, the processive enzyme 244. Once processed, an oligonucleotide with its attached group, such as 246' shown, is displaced from the primary strand 143. The enzyme conjugation 245 to the pore 242 may comprise any of many possible conjugation chemistries, such as the Spy-SpyCatcher protein-based conjugation system. In other examples, the conjugation may comprise a molecular tether. For the nanopore sensor embodiments illustrated in FIG. 23 and FIG. 24, various aspects put forth above in the context of FIG. 1-B also apply, providing a nanopore ion current sensor-based sensor for reading digital data stored in DNA molecules, and the related beneficial aspects, encoding schemes, chip formats, systems and cloud based DNA digital data storage systems.

Figure 25:
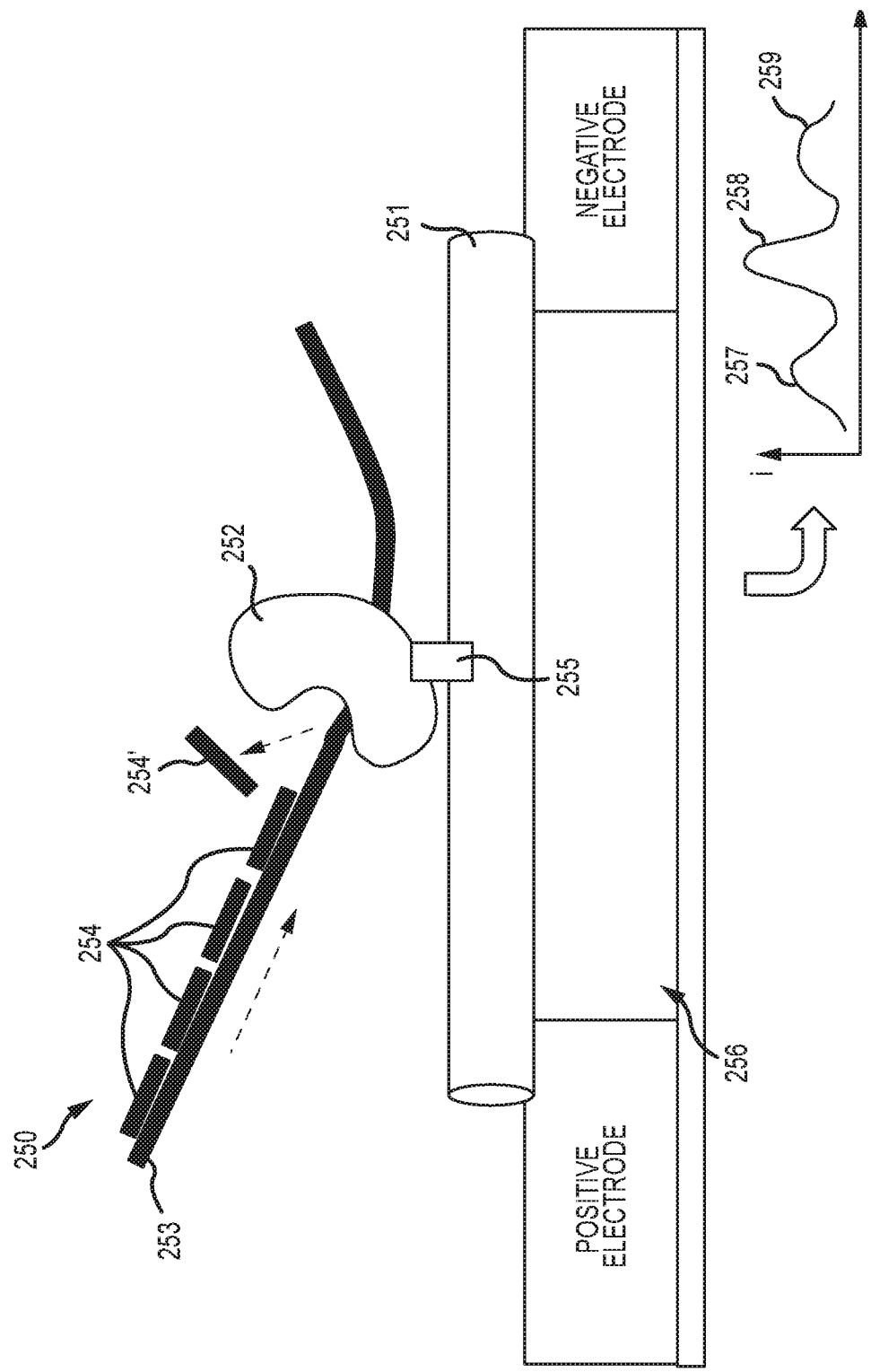
FIG. 25 shows the concept of a DNA data reader sensor which a processive enzyme molecule is complexed with a carbon nanotube molecular wire spanning positive and negative electrodes, and produces distinguishable signal features in the measured current passing through the carbon nanotube.

In various embodiments of a processive enzyme molecular sensor, the sensor comprises a carbon nanotube as the bridge molecule, as illustrated in FIG. 25. As shown, the processive enzyme molecular sensor 250 comprises a carbon nanotube 251 connected at each of its ends to spaced apart electrodes to span the electrode gap 256. In certain aspects, the carbon nanotube 251 comprises a single or multi-walled nanotube, conjugated to the processive enzyme 252 at a specific conjugation site 255, using any of many possible conjugation chemistries. Such a conjugation 255 may, for example, comprise a pyrene linker attached to the nanotube via pi-stacking of the pyrene on the nanotube, or may comprise an attachment to a defect site residing in the carbon nanotube. As per previous embodiments, the processive enzyme 252 processes a DNA template comprising a primary strand 253 with bonded oligonucleotides 254 functioning as distinguishable signaling features that result in perturbations 257, 258, 259, and so forth in the (i) versus (t) plot as shown in the inset of the figure. As the processive enzyme 252 processes the DNA template, oligonucleotides such as 254' shown are displaced. In these embodiments, the current passing through the carbon nanotube 251, acting as a molecular wire, is known to be highly sensitive to the molecules in the environment around the nanotube (e.g. as indicated in FIG. 1-B). It is further known to be sensitive to the activity of an enzyme molecule properly conjugated to the nanotube, including polymerase enzymes. For the embodiments of the sensor 250, all the aspects of the invention put forth above apply in this instance, to provide a carbon nanotube based sensor for reading digital data stored in DNA molecules, including the related beneficial aspects, encoding schemes, chip formats, systems and cloud based DNA digital data storage systems.

Figure 26:
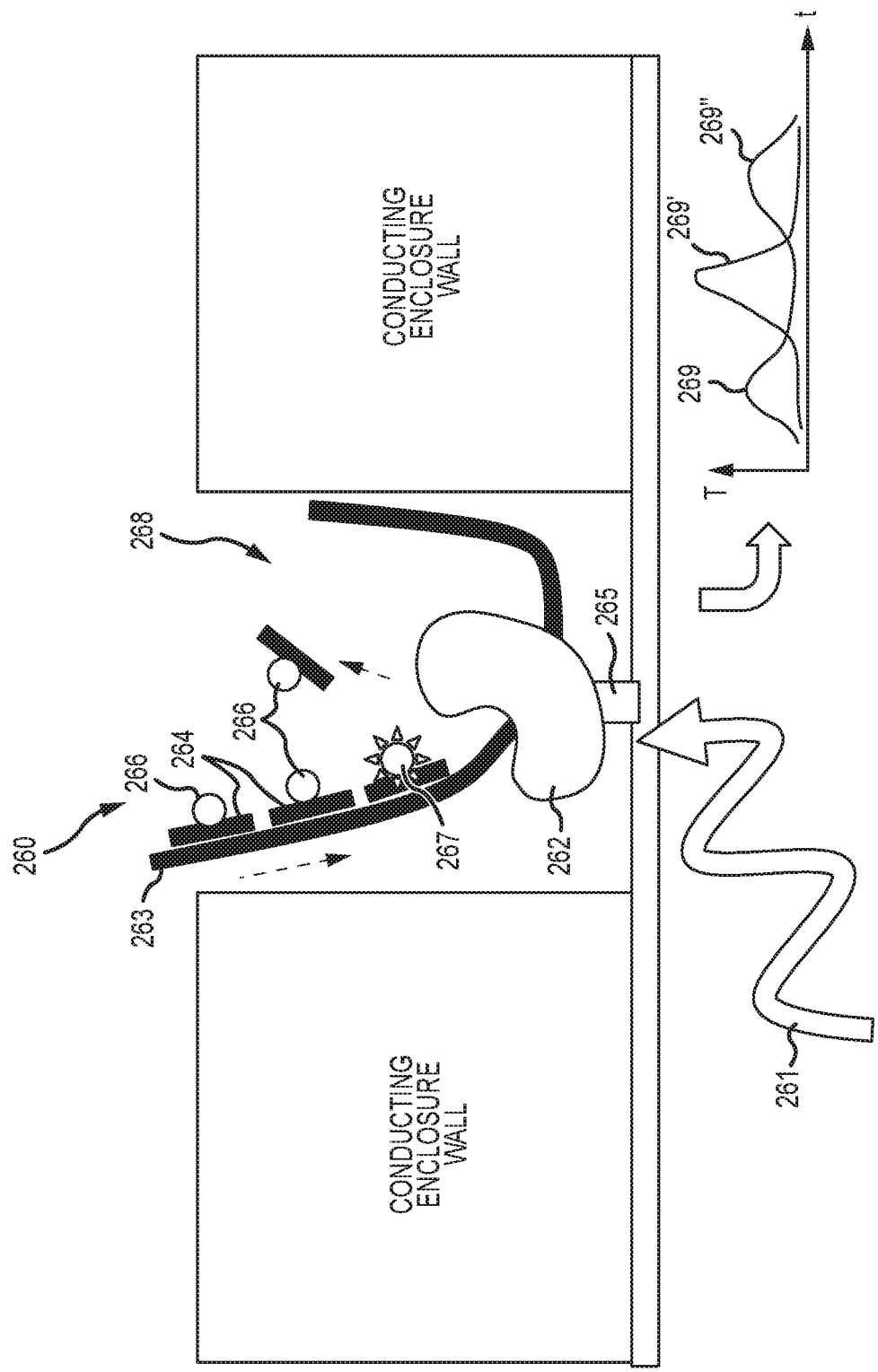
FIG. 26 shows an embodiment of a Zero Mode Waveguide sensor complexed with a processive enzyme molecule, shown in cross section, which produces distinguishable optical signals corresponding to DNA features, here due to dye molecules attached to oligonucleotides bound to the template DNA.

In various embodiments, a processive enzyme molecular sensor provides optical signals via an internal Zero Mode Waveguide sensor, as shown in FIG. 26. Such a sensor 260 comprises a single processive enzyme 262 conjugated at conjugation site 265 to the bottom of a metallic well 268, in the evanescent zone of the excitation field applied to the thin substrate, in a Total Internal Reflection mode. The processive enzyme 262 is provided with an encoded DNA template having a primary strand 263 with dye labels 266 on the bound oligonucleotides 264 on the template. When such a dye label 266 is translocated to the enzyme 262, the dye label 266 is held in the evanescent field, and is stimulated by the excitation beam 261 to emit photons 267 of the corresponding dye energy spectrum or color. The result is that, under appropriate conditions, such a sensor produces distinguishable optical signals 269, 269', 269" and so forth, as indicated in a percent (%) transmission (T) versus time (t) plot, which can be used to encode digital information into DNA molecules. The distinguishable signals here may be photon emissions of a different energy distribution, or color, or emissions with different distinguishable spectra, or different duration or intensity or shape of the spectra versus time, or any combination of such elements that result in distinguishable features. For the Zero Mode Waveguide sensor embodiments indicated in FIG. 26, all the aspects of the invention put forth above in the context of FIG. 1-B also apply in this instance, to provide a Zero Mode Waveguide-based sensor for reading digital data stored in DNA molecules, and the related beneficial aspects, encoding schemes, chip formats (in this case, optical sensor chips, such as image sensor chips), systems and cloud based DNA digital data storage systems may apply to such a sensor.

Figure 27:
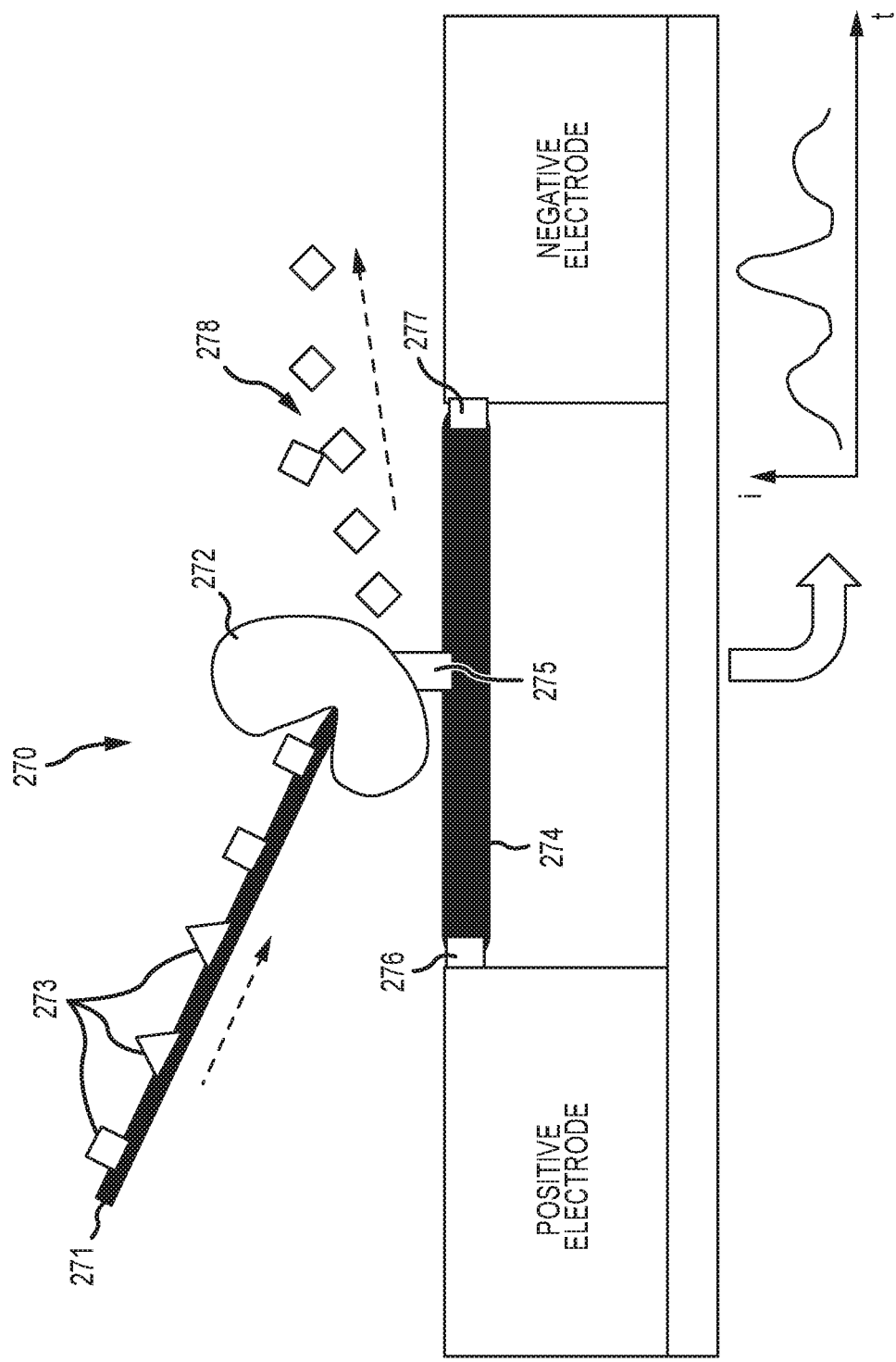
FIG. 27 shows embodiments of a processive enzyme molecular electronic sensor, capable of reading information stored in a polymer other than DNA, comprising a lysozyme enzyme that produces distinguishable signals from signaling groups attached to a peptidoglycan polymer that is digested by the enzyme.

In other embodiments, a molecular sensor used for reading encoded information may comprise an enzyme molecule capable of processing a non-DNA polymer template, as long as such a polymer allowed for bound, displaceable groups, or for permanently bound signaling features, as discussed above in the context of DNA molecules with oligonucleotides or perturbation groups bonded to a primary strand. Various embodiments of non-DNA data reading sensors is shown in FIG. 27, wherein a lysozyme enzyme 272 is attached to a molecular bridge 274 at specific conjugation point 275. The bridge molecule comprises first and second ends for bonding to each electrode in a pair of spaced apart electrodes at contact points 276 and 277. In these sensors 270, the lysozyme 272 sequentially digests a peptidoglycan polymer 271 having amino acid side chains into digestion products 278 comprising various saccharides. Digital data may be encoded into the peptidoglycan 217, by bound groups 273, which are read in a fashion similar to the sensor of FIG. 11. Thus, polymers other than DNA can be used to store digital data, with readers as outlined herein, and with a cognate processive enzyme that translocates along such a polymer as all or part of its enzyme activity.

FURTHER EMBODIMENTS

In various embodiments, a DNA data reading sensor, usable in a DNA data storage system, is disclosed. The molecular sensor comprises: (a) a pair of spaced-apart nano-electrodes; (b) a single processive enzyme complexed between the nano-electrodes to form a molecular electronic circuit; (c) a measurable electronic parameter of the circuit, modulated by the enzyme activity; (d) a measurement buffer and reagent solution and electrical operating parameters for making such measurements of the parameter of (c); and a feature of a DNA template molecule to be processed by the enzyme, with at least two possible states, that, when processed by enzyme of (b), said states produce distinguishable electrical signals in the measurable parameter of (c), when performed in the conditions provided by buffer and settings of (d).

The DNA data reading sensor may further comprise a gate electrode.

The processive enzyme of the DNA data reading sensor may be conjugated in place using a bridge molecule, or any number of arm or linker molecules to assist bonding the enzyme into the sensor circuit, such as shown in the drawing figures, and in particular where such bridge or arm molecules comprise a double stranded DNA, a protein alpha helix, a graphene nanoribbon, a carbon nanotube, an antibody, or Fab arm of an antibody.

The processive enzyme of the DNA data reading sensor may comprise a native or genetically engineered form of one of: a polymerase, a reverse transcriptase, a helicase, an exonuclease, and a molecular motor for packaging of viral DNA.

The measurable electronic parameter of the DNA data reading sensor is the source-drain current between the electrodes.

The signaling features may comprise oligonucleotides bound to a DNA template, which are displaced by the processive enzyme as the enzyme translocates along the DNA. The signaling features can also comprise chemical groups strongly bound to the DNA template such that they are not displaced from the DNA template strand as the enzyme translocates along the DNA.

The signaling features can also comprise oligonucleotides bound to the DNA template, wherein the oligonucleotides each have an additional chemical group attached, and wherein the oligonucleotides are displaced by the processive enzyme as it translocates along the DNA.

The DNA segments that produce distinguishable electrical signals may comprise any combination of binding sites for oligonucleotides and chemical groups conjugated to the DNA.

In various embodiments, a CMOS sensor array chip is disclosed. The CMOS sensor array chip may comprise an array of the DNA data reading sensor described along with supporting pixel circuitry that performs measurement of the measurable electrical parameter.

In various embodiments, a method of reading data encoded in a DNA molecule is disclosed. The method comprises: obtaining a DNA molecule that uses distinguishable signals of the DNA data reading sensor described to encode digital data; applying the molecule to the sensor within the buffer and reagent solution described; measuring the measurable electronic parameter; recording or extracting or capturing the distinguishable signals; and converting the measured distinguishable signals into the encoded data format.

In various embodiments, a method of reading data encoded in DNA with enhanced accuracy is disclosed. The method comprises: obtaining a DNA molecule that uses the distinguishable signals of the DNA data reading sensor described above to encode digital data; applying the molecule to the sensor of claim within the buffer and reagent solution described; measuring the measurable electronic parameter as described; repeating these steps multiple times for the same data payload of the DNA, through any combination of the following: distinct sensors capturing and processing distinct DNA molecules containing the same data payload; the same sensor processing the same DNA molecule multiple times, by using such molecules with a circular or hairpin or tandem repeat architecture that enables multiple processing; and the same sensor capturing and processing distinct DNA molecules that contain the same data payload; recording or extracting or capturing the distinguishable signals from all such reads of the same data payload; and converting the measured distinguishable signals from the multiple reads for the data payload into the encoded data format, by algorithmically aggregating the multiple readings to produce a most accurate, inferred encoded data format of the data payload.

A method of encoding data into a DNA molecule uses the distinguishable signal features of DNA from a DNA data reading sensor.

A method of encoding data into a DNA molecule uses a series of hybridized oligonucleotides, wherein such oligonucleotides may be with or without added chemical groups.

A method of encoding data into a DNA molecule uses encoding schemes in accordance with those described in FIG. 16 and related text, wherein said features produce distinguishable signal features in a DNA data reading sensor as described, and wherein such encoding comprises use of a bound oligonucleotide and/or use of a conjugated chemical group.

A method of encoding data into a DNA molecule using distinguishable signal features of a DNA data reading sensor comprises: treating distinguishable features as information states or symbols of an alphabet; using a lossless or lossy data encoding scheme that translates data encoded as a string in a binary or other digital alphabet, to a string in this feature symbol representation; and defining the encoded DNA sequence in accordance with the resulting string of features, by directly transforming it into the corresponding sequence, or possibly with standard other sequence elements placed between such features, such as spacers, or elements related to the method of DNA synthesis, or other forms of punctuation sequence between distinguishable signal feature sequences.

A method for reading data encoded in DNA in parallel comprises: applying a multiplicity of DNA molecules that use the distinguishable signal DNA features of a DNA data reading sensor as described to encode digital data; applying said molecules to a sensor array chip as described within a buffer and reagent solution; measuring the measurable electronic parameter of for each sensor within the array using the pixel circuitry mentioned; recording or extracting or capturing the distinguishable signals from each pixel for each DNA molecule; and converting the measured distinguishable signals from each pixel into the encoded data format for each DNA molecule.

A method for reading data stored in DNA at very high throughput comprises: supplying one or more chips to a motherboard that controls and transfers data from said chips; introducing DNA molecules encoding information utilizing the distinguishable signal features of the chip, and the related measurement buffer, to the sequencing chips; and capturing the resulting distinguishable signal features for the molecules of (b) and converting them back to the digital data encoded format.

A DNA data reading system comprises one or more such reading sensor array chips as described; an electronic hardware system for controlling and managing the electrical inputs and data outputs of such chips; a fluidic system for introducing the data encoding DNA molecules and measurement buffer to the chips; and a signal processing and data recording system for capturing the measured distinguishable signals, and converting these distinguishable signal feature measurements back to the digital data encoded format.

The chips may be single use, and replacement chips can be loaded to provide reading capacity over time.

The chips can be reconditioned or reset in situ, for repeated or continuous use to provide reading capacity over time.

In various embodiments, a cloud based DNA data storage system is disclosed. The system comprises: a data reader server cloud, which in turn comprises a DNA data reading system as described.

In various embodiments, a molecular electronics DNA data reading sensor is disclosed. The sensor comprises: a nanopore ion current sensor; a single processive enzyme complexed with the nanopore as part of a molecular complex; a measurement buffer and reagent solution and electrical operating parameters for making such measurements of the ion current through the pore; and a feature of the DNA template molecule, with at least two possible states, that, when processed by enzyme of (b), said states produced distinguishable electrical signals in the nanopore ion current sensor of (a), when performed in the conditions provided by buffer and settings of (c).

The signaling features may comprise oligonucleotides with attached groups that alter power ion current by directly engaging with the pore.

These sensors described can be used to read data encoded in DNA, in accordance with the methods disclosed.

In various embodiments, a molecular electronics DNA data reading sensor is disclosed. The sensor comprises: a pair of nano-electrodes; a carbon nanotube spanning the electrodes and in electrical contact; a single processive enzyme conjugated to the carbon nanotube; and a measurement buffer and reagent solution and electrical operating parameters for making measurements of the current passing through the nanotube between the electrodes.

In various embodiments, a DNA data reading sensor comprises: (a) a Zero Mode Waveguide; (b) a single processive enzyme conjugated to the bottom of the zero mode waveguide; (c) a measurement buffer and reagent solution and optical excitation operating parameters for making a measurements of optical emissions form the Zero Mode Waveguide; and (d) a feature of the DNA template molecule, with at least two possible states, that, when processed by enzyme of (b), said states produced distinguishable optical signals when performed in the conditions provided by buffer and settings of (c).

The above sensor may be used to read data encoded in DNA, in accordance with the methods described.

In various embodiments, a molecular electronics sensor for reading digital data encoded in a polymer is disclosed. The sensor comprises: a pair of nano-electrodes; a non-DNA polymer; a single processive enzyme complexed between the nano-electrodes as part of a molecular electronic circuit, where said enzyme acts processively on the polymer; a measurable electronic parameter of the circuit, modulated by the enzyme activity; a measurement buffer and reagent solution and electrical operating parameters for making such measurements of the measurable electronic parameter; and a feature of the polymer molecule, with at least two possible states, that, when processed by processive enzyme, said states produced distinguishable electrical signals in the measurable electronic parameter when performed in the conditions provided by the buffer and settings.

This sensor may be used to read data encoded in the polymer in accordance with the methods described, wherein DNA in the prior embodiments is replaced by the polymer.

DNA data reading processive enzyme molecular sensors and methods of making and using same are provided. References to "various embodiments", "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Benefits, other advantages, and solutions to problems have been described with regard to specific embodiments. However, the benefits, advantages, solutions to problems, and any elements that may cause any benefit, advantage, or solution to occur or become more pronounced are not to be construed as critical, required, or essential features or elements of the disclosure. The scope of the disclosure is accordingly to be limited by nothing other than the appended claims, in which reference to an element in the singular is not intended to mean "one and only one" unless explicitly so stated, but rather "one or more." Moreover, where a phrase similar to 'at least one of A, B, and C' or 'at least one of A, B, or C' is used in the claims or specification, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C.

All structural, chemical, and functional equivalents to the elements of the above-described various embodiments that are known to those of ordinary skill in the art are expressly incorporated herein by reference and are intended to be encompassed by the present claims. Moreover, it is not necessary for a device or method to address each and every problem sought to be solved by the present disclosure, for it to be encompassed by the present claims. Furthermore, no element, component, or method step in the present disclosure is intended to be dedicated to the public regardless of whether the element, component, or method step is explicitly recited in the claims. No claim element is intended to invoke 35 U.S.C. 112(f) unless the element is expressly recited using the phrase "means for." As used herein, the terms "comprises", "comprising", or any other variation thereof, are intended to cover a non-exclusive inclusion, such that a molecule, composition, process, method, or device that comprises a list of elements does not include only those elements but may include other elements not expressly listed or inherent to such molecules, compositions, processes, methods, or devices.

What is claimed is:

1. A sensor comprising:
a first electrode;
a second electrode spaced apart from the first electrode by an electrode gap;
a gate electrode capacitively coupled to the electrode gap;
a DNA bridge molecule spanning the electrode gap and having a first end and a second end, the first end conjugated to the first electrode and the second end conjugated to the second electrode;
a processive enzyme conjugated to the first electrode and the second electrode via the DNA bridge molecule, the processive enzyme comprising a native or genetically engineered polymerase, a reverse transcriptase, a helicase, an exonuclease, or a molecular motor for packaging of viral DNA; and
a trans-impedance amplifier electrically connected to the gate electrode and at least one of the first electrode and the second electrode, the trans-impedance amplifier providing a biasable voltage to the gate electrode and an output comprising a measurable electrical parameter.

2. The sensor of claim 1, wherein the biasable voltage is across from the first electrode to the second electrodes, and wherein the measurable electrical parameter comprises a current output.

3. The sensor of claim 1, wherein the processive enzyme is directly wired between the first electrode and the second electrode to provide a conductive pathway between the first electrode and the second electrode, through the processive enzyme.

4. The sensor of claim 1, wherein the first electrode and the second electrode are a source electrode and a drain electrode respectively, and wherein the trans-impedance amplifier provides the biasable voltage to the source electrode, the drain electrode and the gate electrodes.

5. The sensor of claim 1, wherein the output comprising the measurable electrical parameter is a current output and comprises perturbations.

6. The sensor of claim 1, wherein the first electrode and the second electrode area source electrode and a drain electrode respectively, and wherein the measurable electrical parameter is a source-drain current between the source electrode and the drain electrode.

7. The sensor of claim 1, wherein the DNA bridge molecule comprises a double stranded DNA.

8. A sensor comprising:
a first electrode;
a second electrode spaced apart from the first electrode by an electrode gap;
a gate electrode capacitively coupled to the electrode gap;
at least two arm molecules electrically connected a processive enzyme to the first electrode and the second electrode, wherein one of the at least two arm molecules is selected from a double stranded DNA and a protein alpha helix, and the processive enzyme comprises a native or genetically engineered polymerase, a reverse transcriptase, a helicase, an exonuclease, or a molecular motor for packaging of viral DNA; and
a trans-impedance amplifier electrically connected to the gate electrode and at least one of the first electrode and the second electrode, the trans-impedance amplifier providing a biasable voltage to the gate electrode and an output comprising a measurable electrical parameter.

9. The sensor of claim 8, wherein the one of the at least two arm molecules is the protein alpha helix.

10. The sensor of claim 8, wherein the one of the at least two arm molecules is the a double stranded DNA.

* * * * *